US007667055B2

(12) United States Patent
Vu et al.

(10) Patent No.: US 7,667,055 B2
(45) Date of Patent: *Feb. 23, 2010

(54) PROCESSES FOR THE PRODUCTION OF POLYCYCLIC FUSED RING COMPOUNDS

(75) Inventors: Phong Vu, Little Falls, NJ (US); Robert A. Holton, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 415 days.

This patent is subject to a terminal disclaimer.

(21) Appl. No.: 11/449,535

(22) Filed: Jun. 8, 2006

(65) Prior Publication Data

US 2006/0281934 A1 Dec. 14, 2006

Related U.S. Application Data

(60) Provisional application No. 60/788,943, filed on Apr. 4, 2006, provisional application No. 60/724,527, filed on Oct. 7, 2005, provisional application No. 60/689,425, filed on Jun. 10, 2005.

(51) Int. Cl.
C07D 407/00 (2006.01)
(52) U.S. Cl. ..................... 549/510; 549/511
(58) Field of Classification Search ................. 549/510, 549/511
See application file for complete search history.

(56) References Cited

U.S. PATENT DOCUMENTS

| 4,924,011 | A | 5/1990 | Denis et al. |
|---|---|---|---|
| 5,015,744 | A | 5/1991 | Holton |
| 5,175,315 | A | 12/1992 | Holton |
| 5,399,726 | A | 3/1995 | Holton et al. |
| 5,430,160 | A | 7/1995 | Holton |
| 5,466,834 | A | 11/1995 | Holton |
| 5,539,103 | A | 7/1996 | Holton |
| 5,668,270 | A | 9/1997 | Bauman et al. |
| 5,723,634 | A | 3/1998 | Holton |
| 5,760,251 | A | 6/1998 | Gao et al. |
| 5,763,477 | A | 6/1998 | Duvvuri et al. |
| 6,191,287 | B1 | 2/2001 | Holton et al. |
| 6,225,463 | B1 | 5/2001 | de Vos et al. |
| 6,265,587 | B1 | 7/2001 | Chanteloup et al. |
| 6,562,962 | B2 | 5/2003 | Holton |
| 6,825,365 | B2 | 11/2004 | Chanteloup et al. |

FOREIGN PATENT DOCUMENTS

| EP | 0 400 971 A2 | 5/1990 |
|---|---|---|
| EP | 0 617 034 A1 | 9/1994 |
| WO | 97/07110 A1 | 2/1997 |
| WO | 97/15562 A1 | 5/1997 |
| WO | 02/085878 A1 | 10/2002 |
| WO | 2004/013096 A2 | 2/2004 |
| WO | 2006/004898 A2 | 1/2006 |
| WO | 2006/089207 A2 | 8/2006 |
| WO | 94/18164 A1 | 1/2007 |

OTHER PUBLICATIONS

Office Action dated Oct. 10, 2007, U.S. Appl. No. 11/449,075, 4 pages.
Office Action dated Oct. 17, 2007, U.S. Appl. No. 11/449,048, 6 pages.
Tarrant, J.G. et al., "Synthesis and Biological Activity of Macrocyclic Taxane Analogues," Bioorganic & Medicinal Chemistry Letters, 2004, pp. 2555-2558, vol. 14.
Corriu, R.J.P., "Hypervalent Species of Silicon: Structure and Reactivity," Journal of Organometallic Chemistry, 1990, pp. 81-106, vol. 400.
Denis, J.-N., et al., "A Highly Efficient, Practical Approach to Natural Taxol," J. Am. Chem. Soc., 1988, pp. 5917-5919, vol. 110, No. 17.
Grobe, J. et al., "Atrane Analogous Compounds of Type Me2Si-Y-M'Me2(OCH2CH2)NME (-O-CH3-CH2-) (I)," Z. Naturforsch., B. Anorg. Chem., Org. Chem., 1983, pp. 269-279, vol. 38B, No. 3.
Gueritte-Voegelein, F., et al., "Chemical Studies of 10-Deacetyl Baccatin III. Hemisynthesis of Taxol Derivatives," Tetrahedron, 1986, pp. 4451-4460, vol. 42, No. 16.
Holton, R.A., et al., "Selective Protection of the C(7) and C(10) Hydroxyl Groups in 10-Deacetyl Baccatin III," Tetrahedron Letters, 1998, pp. 2883-2886, vol. 39.
Office Action dated Feb. 16, 2007, U.S. Appl. No. 11/449,075, 13 pages.
Office Action dated Apr. 26, 2007, U.S. Appl. No. 11/449,048, 9 pages.
Office Action dated Jun. 21, 2007, U.S. Appl. No. 11/449,075, 16 pages.
Uhlig, W., et al., "Synthesis and Reactivity of Triflate Substituted Siloxane Derivatives," Z. Anorg. Allg. Chem., 1994, pp. 939-943, vol. 620.
Jagtap, P. G., et al., "A Facile N-Debenzoylation of Paclitaxel: Conversion of Paclitaxel to Docetaxel," Tetrahedron Letters, 1999, pp. 189-192, vol. 40.
International Search Report, PCT/US2006/022213, dated Dec. 14, 2006, 5 Pages.
Farina et al., "A Simple Chiral Synthesis of the Taxol Side Chain" Synlett, 9:761 (1992).
Commercon, A., et al., "Improved Protection and Esterification of a Precursor of the Taxotere® and Taxol Side Chains", Tetrahedron Letters, 1992, pp. 5185-5188, vol. 33, No. 36.
Denis, J-N., et al., "A Highly Efficient, Practical Approach to Natural Taxol", J. Am. Chem. Soc., 1988, pp. 5917-5919, vol. 110, No. 17.
Hart, D. J., et al., "The Ester Enolate-Imine Condensation Route to β-Lactams", Chem. Rev., 1989, pp. 1447-1465, vol. 89, No. 7.
Mangatal, L., et al., "Application of the Vicinal Oxyamination Reaction with Asymmetric Induction to the Hemisynthesis of Taxol and Analogues", Tetrahedron, 1989, pp. 4177-4190, vol. 45, No. 13.
Senilh, V., et al., "Analyse Structurale et etude Biochimique de produits isoles de I'lf: Taxus baccata L. (Taxacees)", C.R. Acad. Sci. Paris, IT, 1981, pp. 501-503, vol. 293, No. 7.
van Tilburg, E. W., et al., "Radiosynthesis of [11C]docetaxel", Journal of Labelled Compounds and Radiopharmaceuticals, 2004, pp. 763-777, vol. 47.

*Primary Examiner*—Janet L. Andres
*Assistant Examiner*—Raymond Covington
(74) *Attorney, Agent, or Firm*—Bryan Cave LLP

(57) ABSTRACT

The present invention provides processes for the production of polycyclic fused ring compounds. The polycyclic fused ring compounds are produced by protecting a polycyclic fused ring polyol with a bridging silicon-based protecting group and attaching a suitable side chain. Polycyclic fused ring compounds and intermediate compounds are also described.

50 Claims, No Drawings

PROCESSES FOR THE PRODUCTION OF POLYCYCLIC FUSED RING COMPOUNDS

REFERENCE TO RELATED APPLICATIONS

This application claims priority from U.S. provisional application Ser. No. 60/689,425, filed on Jun. 10, 2005; U.S. provisional application Ser. No. 60/724,527, filed on Oct. 7, 2005; and U.S. provisional application Ser. No. 60/788,943, filed on Apr. 4, 2006.

BACKGROUND OF THE INVENTION

The present invention generally relates to processes for producing polycyclic fused ring compounds. More specifically, the present invention relates to processes for the production of polycyclic fused ring compounds including the simultaneous protection of the C(7) and C(10) hydroxy groups of a polycyclic fused ring polyol having the taxane tetracyclic nucleus.

10-DAB (I), which is extracted from the needles of the English yew (*taxus baccata* L.) is a key starting material in the production of taxol (also known as paclitaxel) and docetaxel (Taxotere®), both of which are potent anticancer agents.

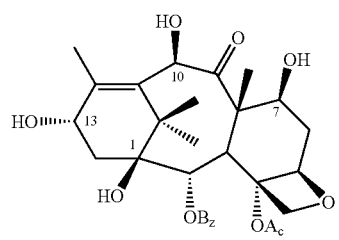

Conversion of 10-DAB to a cytotoxically active taxane requires selective derivatization of the C(13) hydroxy group to form a C(13) ester side chain. Because 10-DAB is a polyol and because each of these hydroxy groups is not equally reactive under a defined set of conditions, preparation of taxol or docetaxel from 10-DAB typically requires selective protection and/or derivatization of the C(7) and C(10) hydroxy groups before the C(13) side chain is attached.

Early strategies for the preparation of taxol, docetaxel and other taxanes from 10-DAB were based on the observation of Senilh et al. (*C.R. Acad. Sci. Paris, IT,* 1981, 293, 501) that the relative reactivity of the four hydroxy groups of 10-DAB toward acetic anhydride in pyridine is C(7)—OH>C(10)—OH>C(13)—OH>C(1)—OH. Denis et al. reported (*J. Am. Chem. Soc.,* 1988, 110, 5917) selective silylation of the C(7) hydroxy group of 10-DAB with triethylsilyl chloride in pyridine to give 7-triethylsilyl-10-deacetyl baccatin (III) in 85% yield.

More recently, Holton et al. disclosed in U.S. Pat. No. 6,191,287 that the relative reactivity toward acetic anhydride as between C(7) and C(10) is different in the presence of a Lewis acid than it is in the presence of base. Holton et al. described processes for the selective derivatization of the C(7) or the C(10) hydroxy group of 10-DAB and other taxanes, wherein the C(10) hydroxy group may be protected or derivatized prior to the C(7) hydroxy group. Specifically, Holton et al. described a process for acylating or silylating the C(10) hydroxy group prior to acylating, silylating, or ketalizing the C(7) hydroxy group.

In U.S. Pat. No. 5,763,477, Duvvuri et al. disclose the preparation of various taxanes using, as a starting material, 14-β-hydroxy-10-DAB (II).

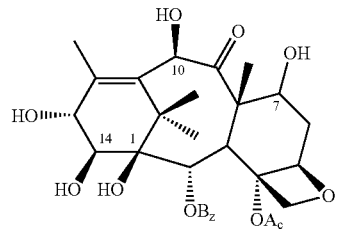

Before derivatizing the C(13) hydroxy group, a necessary step for the preparation of a cytotoxically active taxane, Duvvuri et al. protect the C(1), C(7), C(10), and C(14) hydroxy groups using a dimethyl acetal of an appropriate aldehyde or ketone or an enol-ether to form fused rings at C(14) and C(1) and at C(7) and C(10):

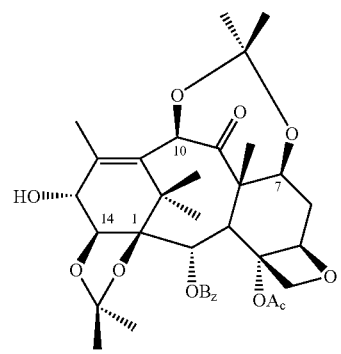

See, for example, Duvvuri et al., U.S. Pat. No. 5,763,477 at column 7, lines 23-52. After protecting the C(1), C(7), C(10), and C(14) hydroxy groups to form compound (III), Duvvuri et al. derivatize the C(13) hydroxy group to attach a side chain and then deprotect the C(1) and C(14) hydroxy groups and optionally the C(7) and C(10) hydroxy groups. Disadvantageously, however, Duvvuri et al. report relatively low conversion rates for the protection and deprotection steps (see, e.g., Duvvuri et al.'s Examples 1, and 11-14).

In U.S. Pat. No. 6,825,365, Chanteloup et al. disclose protecting the C(7) and the C(10) hydroxy groups of a baccatin III using a disiloxane substituted with sterically hindered isopropyl groups to form a fused ring at C(7) and C(10):

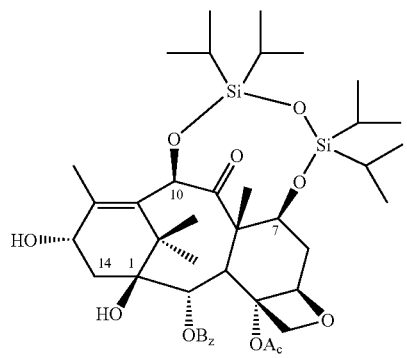

See, for example, Chanteloup et al., U.S. Pat. No. 6,825,365 at column 9, line 1 to column 10, line 44 and Example 22.

After protecting the C(7) and C(10) hydroxy groups to form compound (IV), Chanteloup et al. treat the protected compound with an isoserine or oxazoline side chain precursor to derivatize the C(13) hydroxy group. When oxazoline side chain precursors are utilized, the oxazoline ring may be optionally opened by hydrolysis after the attachment of the side chain at the C(13) position of the protected baccatin III. See, e.g., Chanteloup et al., U.S. Pat. No. 6,825,365 at columns 10-14. Disadvantageously, Chanteloup et al. report relatively low conversion rates for the protection steps, fail to disclose any non-sterically hindered bifunctional protecting groups, and report no method for removal of the bifunctional protecting group (see, e.g., Chanteloup et al.'s Examples 14-22 and 29).

SUMMARY OF THE INVENTION

Among the various aspects of the present invention is the provision of a process for producing a polycyclic fused ring compound by selectively protecting at least two hydroxy groups of a polycyclic fused ring polyol, wherein the protection and subsequent deprotection steps proceed in relatively high yield.

Briefly, therefore, the present invention is directed to a process for the production of a polycyclic fused ring compound corresponding to Formula (10):

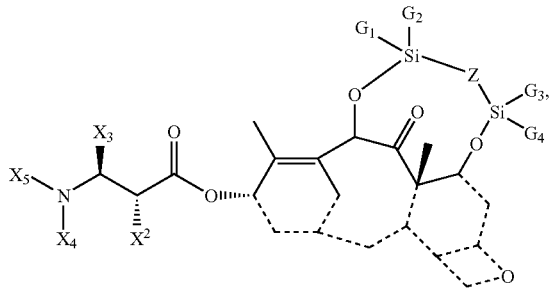

(10)

the process comprising treating a polycyclic fused ring polyol with a bridging silicon-based protecting group and a side chain precursor, wherein the polycyclic fused ring polyol corresponds to Formula (3):

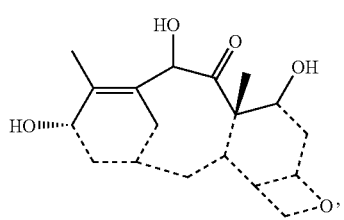

(3)

the bridging silicon-based protecting group corresponds to Formula (4):

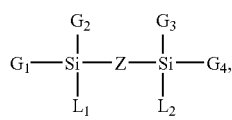

(4)

the side chain precursor corresponds to Formula (6)

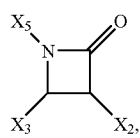

(6)

$X_2$ is alkyl, alkenyl, alkynyl, aryl, heterocyclo, —$OX_6$, —$SX_7$, or —$NX_8X_9$;

$X_3$ is substituted or unsubstituted alkyl, alkenyl, alkynyl, phenyl, or heterocyclo;

$X_5$ is —$COX_{10}$, —$COOX_{10}$, or —$CONHX_{10}$;

$X_6$ is acyl, alkyl, alkenyl, alkynyl, aryl, heteroaryl, hydrogen, or hydroxy protecting group;

$X_7$ is alkyl, alkenyl, alkynyl, aryl, heteroaryl, or sulfhydryl protecting group;

$X_8$ is hydrogen, hydrocarbyl, substituted hydrocarbyl, or heterocyclo;

$X_9$ is an amino protecting group;

$X_{10}$ is hydrocarbyl, substituted hydrocarbyl, or heterocyclo;

$G_1$, $G_2$, $G_3$, and $G_4$ are independently hydrocarbyl, substituted hydrocarbyl, alkoxy, or heterocyclo;

$L_1$, and $L_2$ are independently amine, halide, or sulfonate leaving groups;

Z is hydrocarbyl, substituted hydrocarbyl, heterocyclo, —[O—Si($Z_{10}$)($Z_{11}$)—]$_n$O—, or —O—;

$Z_{10}$ and $Z_{11}$ are hydrocarbyl;

n is 1 or 2; and the dashed lines denote the skeletal structure of the polycyclic fused ring polyol.

The present invention is also directed to a process for the production of a polycyclic fused ring compound corresponding to Formula (12):

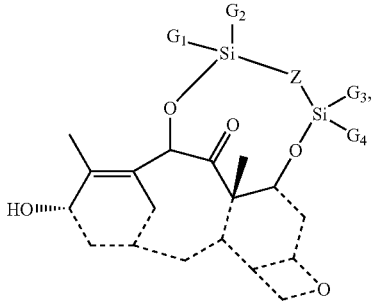

(12)

the process comprising treating a polycyclic fused ring polyol with a bridging silicon-based protecting group, wherein the polycyclic fused ring polyol corresponds to Formula (3):

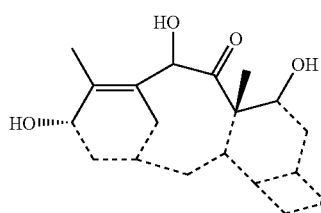

(3)

and the bridging silicon-based protecting group corresponds to Formula (4):

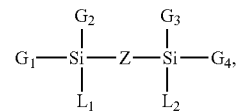

(4)

wherein $G_1$, $G_2$, $G_3$, $G_4$, $L_1$, $L_2$, and Z are as defined in connection with Formula (4) and the dashed lines denote the skeletal structure of the polycyclic fused ring polyol, provided, however, that $G_1$, $G_2$, $G_3$, and $G_4$ are not branched alkyl when Z is —O—.

The present invention is also directed to a process for the production of a polycyclic fused ring compound corresponding to Formula ($20_R$):

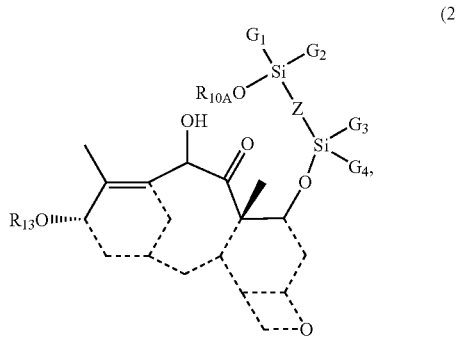

(${20_R}$)

the process comprising treating a polycyclic fused ring compound corresponding to Formula ($9_R$):

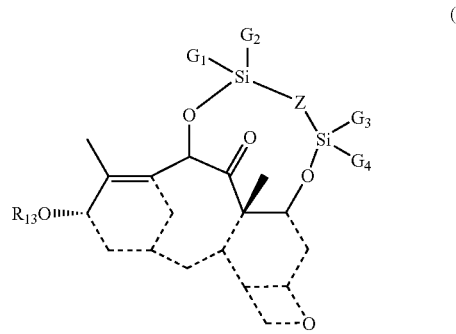

($9_R$)

with an alcohol and a base, wherein
the alcohol has the formula $R_{10A}OH$;
$R_{10A}$ is hydrocarbyl;
$R_{13}$ is hydrogen or has the structure

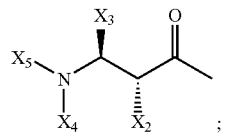

$G_1$, $G_2$, $G_3$, $G_4$, and Z are as defined in connection with Formula (4), $X_2$, $X_3$, $X_4$, and $X_5$ are as defined in connection with Formula (6), and the dashed lines denote the skeletal structure of the polycyclic fused ring compound.

The present invention is also directed to a polycyclic fused ring compound corresponding to Formula ($9_{R13}$):

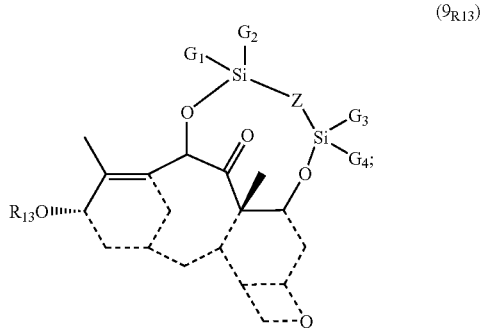

($9_{R13}$)

wherein $G_1$, $G_2$, $G_3$, $G_4$, and Z are as defined in connection with Formula (4), $R_{13}$ is hydrogen, hydroxy protecting group, a metal, comprises ammonium, or has the structure

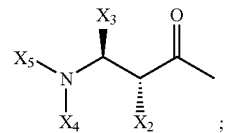

and the dashed lines denote the skeletal structure of the polycyclic fused ring compound, provided, however, $G_1$, $G_2$, $G_3$, and $G_4$ are not branched alkyl when Z is —O—.

The present invention is also directed to a polycyclic fused ring compound corresponding to Formula ($20_{R10}$):

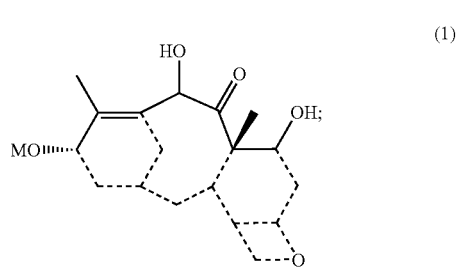

(${20_{R10}}$)

wherein $G_1$, $G_2$, $G_3$, $G_4$, and Z are as defined in connection with Formula (4), $R_{10}$ is hydrogen or acyl; $R_{10A}$ is hydrocarbyl; $R_{13}$ is as defined in connection with Formulae ($9_R$) and (${20_R}$); and the dashed lines denote the skeletal structure of the polycyclic fused ring compound.

Other objects and features will be in part apparent and in part pointed out hereinafter.

DETAILED DESCRIPTION OF THE INVENTION

Among other things, the present invention enables the simultaneous and selective protection of at least two hydroxy groups of a polycyclic fused ring polyol with a bridging silicon-based protecting group. The present invention offers particular advantages in the protection of polycyclic fused ring polyols generally corresponding to Formula (1):

(1)

wherein M is hydrogen, metal, or ammonium and the dashed lines denote the skeletal structure of the polycyclic fused ring polyol. Stated another way, the polycyclic fused ring polyol possesses the A, B, C and D rings of the fused, tetracyclic taxane structure of Formula (2):

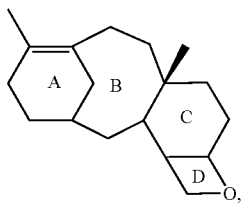
(2)

without regard to the substitution pattern on the fused ring system provided, however, the polyol possesses hydroxy groups at the C(7) and C(10) positions, a keto (=O) at C(9), and MO— at C(13) wherein M is hydrogen, metal, or ammonium. Thus, for example, at the C(1), C(2), C(4), C(6), and C(14) positions, the polyol may be substituted as found in naturally occurring compounds (that is, C(1) is hydroxy substituted, C(2) is benzoyloxy substituted, C(4) is acetoxy substituted, and C(14) is optionally hydroxy substituted). Alternatively, any of these positions may be derivatized to provide non-naturally occurring substituents or non-naturally occurring combinations of substituents as described, for example, in Holton et al., U.S. Pat. No. 5,399,726 (hydroxy or alternative esters at C(2) and/or C(4)) or in Duvvuri et al., U.S. Pat. No. 5,763,477 (C(14) hydroxy, C(14)/C(1) acetal, ketal or carbonate).

In one embodiment, the polycyclic fused ring polyol corresponds to Formula (3):

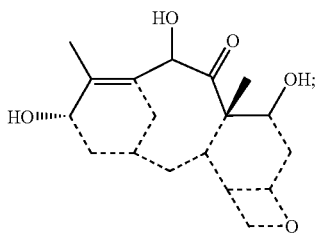
(3)

wherein the dashed lines denote the skeletal structure of the polycyclic fused ring polyol.

In another embodiment, the polycyclic fused ring polyol corresponds to Formula (13):

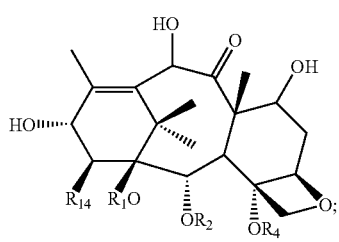
(13)

wherein $R_1$, $R_2$ and $R_4$ are independently hydrogen or acyl, and $R_{14}$ is hydrogen, hydroxy, or acyl. Exemplary acyl groups for each of $R_1$, $R_2$, $R_4$ and $R_{14}$ include esters, carbonates, and carbamates. In addition, proximate substituents may combine to form ring structures such as carbonates, acetals and ketals. For example, $-OR_1$, and $-OR_2$, in combination, may be $-OC(O)O-$ wherein the two oxygen atoms are bonded to the C(1) and C(2) carbon atoms, respectively, to form a C(1)/C(2) carbonate as described in Holton et al., U.S. Pat. No. 5,399,726. Similarly, $R_{14}$ and $-OR_1$, in combination, may be (i) $-OC(R^a)(R^b)O-$ wherein the two oxygen atoms are bonded to the C(1) and C(14) carbon atoms, respectively, to form a C(1)/C(14) ketal or acetal and $R^a$ and $R^b$ are hydrogen, lower alkyl, phenyl, substituted phenyl, lower alkoxy, amino, substituted amino, keto (=O) or thiocarbonyl (=S) as described in Duvvuri et al., U.S. Pat. No. 5,763,477. By way of further example, $R_{14}$ and $-OR_1$, in combination, may be $-OC(O)O-$ wherein the two oxygen atoms are bonded to the C(1) and C(14) carbon atoms, respectively, to form a C(1)/C(14) carbonate as described in Duvvuri et al., U.S. Pat. No. 5,763,477. When the polycyclic fused ring polyol corresponds to Formula (13), $R_1$, is hydrogen, $R_2$ is benzoyl, $R_4$ is acetyl and $R_{14}$ is hydrogen, the fused ring polyol is 10-DAB. When the polycyclic fused ring polyol corresponds to Formula (13), $R_1$ is hydrogen, $R_2$ is benzoyl, $R_4$ is acetyl and $R_{14}$ is hydroxy, the fused ring polyol is 14-β-hydroxy-10-DAB.

In one preferred embodiment, the polycyclic fused ring polyol is 10-DAB and corresponds to Formula (23):

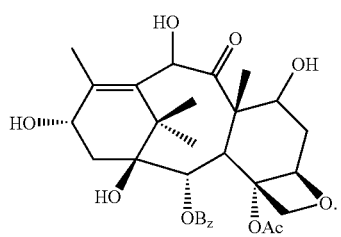
(23)

In accordance with the process of the present invention, it has been discovered that at least two hydroxy groups of a polycyclic fused ring polyol may be selectively and simultaneously protected (relative to other hydroxy groups) by treating the polycyclic fused ring polyol with a bridging silicon-based protecting group. When the polyol corresponds to Formula (13), for example, the C(7) and C(10) hydroxy substituents may be simultaneously protected using a bridging silicon-based protecting group. This enables the protected polycyclic fused ring polyol to be utilized as a synthetic intermediate for subsequent protection or derivatization of other positions on the polycyclic fused ring compound such as by the attachment of a suitable side chain, described in further detail below.

When the polyol corresponds to Formula (13) and depending upon the composition of the remainder of the substituents, that is, $R_1$, $R_2$, $R_4$, and $R_{14}$, the bridging silicon-based protecting group may also derivatize other positions. For example, treatment of 14-β-hydroxy-10-DAB with the bridging silicon-based protecting group may also lead to the protection (derivatization) of the C(1) and/or C(14) hydroxy groups.

Bridging Silicon-Based Protecting Group

Generally speaking, the bridging silicon-based protecting group comprises a backbone comprising two silyl atoms proximate each of two ends. The various substituent groups that may be attached to the silyl atoms typically correspond to any substituent group that does not hinder the ability of the bridging silicon-based protecting group to effectively function as a protecting group. Particularly, the various substituent groups attached to the silyl atoms correspond to substituent groups that do not hinder the ability of the bridging silicon-based protecting group to effectively simultaneously protect a polycyclic fused ring polyol.

At least one of the substituent groups attached to the silyl atoms at each end of the backbone is a leaving group. Generally speaking, the leaving groups are cleaved during the treatment of the polycyclic fused ring polyol with the bridging silicon-based protecting group, resulting in two functionally reactive sites on the bridging silicon-based protecting group backbone. These functionally reactive sites allow the bridging silicon-based protecting group to attach to and protect two hydroxy groups on the polycyclic fused ring polyol. Typically, the leaving groups correspond to any atom or group of atoms that may be easily displaced as a stable species, taking with it the bonding electrons, and that is relatively weakly bonded to the silyl atoms at each end of the bridging silicon-based protecting group backbone.

In a preferred embodiment, the bridging silicon-based protecting groups generally correspond to Formula (4):

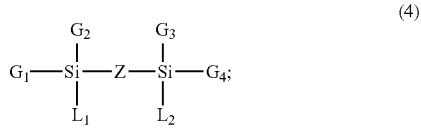

(4)

wherein $G_1$, $G_2$, $G_3$, and $G_4$ are independently hydrocarbyl, substituted hydrocarbyl, alkoxy, or heterocyclo;

$L_1$, and $L_2$ are independently amine, halide, or sulfonate leaving groups;

Z is hydrocarbyl, substituted hydrocarbyl, heterocyclo, —[O—Si($Z_{10}$)($Z_{11}$)—]$_n$O—, or —O—;

each $Z_{10}$ and $Z_{11}$ is independently hydrocarbyl; and n is 1 or 2.

In one embodiment in which the bridging silicon-based protecting group corresponds to Formula (4), Z is hydrocarbyl. In one such embodiment, Z is —(CH$_2$)$_y$— wherein y is a positive integer from 1 to about 8. More preferably in this embodiment, y is 1 to about 4.

In another embodiment in which the bridging silicon-based protecting group corresponds to Formula (4), Z is substituted hydrocarbyl. In one particular embodiment, Z is -[($Z_{12}$)-(Z13)]$_k$-[($Z_{14}$)]$_m$-, wherein $Z_{12}$, $Z_{13}$, and $Z_{14}$ are each independently —(CH$_2$)$_y$—, —O—, —S—, or —N—, provided that at least one of $Z_{12}$ and $Z_{13}$ is —O—, —S—, or —N—, k is a positive integer from 1 to about 4, m is 0 or 1, and y is a positive integer from 1 to about 4.

In another embodiment in which the bridging silicon-based protecting group corresponds to Formula (4), Z is —O—. In yet another embodiment in which the bridging silicon-based protecting group corresponds to Formula (4), Z is —[O—Si($Z_{10}$)($Z_{11}$)-]$_n$O—, wherein n is 1 or 2. That is, when n is 1, Z is —O—Si($Z_{10}$)($Z_{11}$)-O—; and when n is 2, Z is —O—Si($Z_{10}$)($Z_{11}$)—O—Si($Z_{10}$)($Z_{11}$)—O—. When n is either 1 or 2, each $Z_{10}$ and each $Z_{11}$ is independently hydrocarbyl (that is, the two $Z_{10}$ substituents need not be the same hydrocarbyl moiety and the two $Z_{11}$ substituents need not be the same hydrocarbyl moiety). In some embodiments, $Z_{10}$ and $Z_{11}$, are alkyl. In other embodiments, $Z_{10}$ and $Z_{11}$ are lower alkyl having from about 1 to about 4 carbon atoms. In still other embodiments, $Z_{10}$ and $Z_{11}$, are methyl.

In any one of the various embodiments described above (i.e., when Z is —(CH$_2$)$_y$—, -[($Z_{12}$)-($Z_{13}$)]$_k$-[($Z_{14}$)]$_m$-, —[O—Si($Z_{10}$)($Z_{11}$)-]$_n$O—, or —O—), $G_1$, $G_2$, $G_3$, and $G_4$ are independently hydrocarbyl, substituted hydrocarbyl, alkoxy, or heterocyclo. In some embodiments, $G_1$, $G_2$, $G_3$, and $G_4$ are independently substituted or unsubstituted alkyl, alkenyl, alkynyl, aryl, heteroaryl, or cycloalkyl. In other embodiments, $G_1$, $G_2$, $G_3$, and $G_4$ are independently linear or branched alkyl or alkenyl having from about 1 to about 4 carbon atoms, cycloalkyl having from about 1 to about 6 carbon atoms, or phenyl. In still other embodiments, $G_1$, $G_2$, $G_3$, and $G_4$ are independently methyl, ethyl, ethenyl, isopropyl, phenyl, or cyclopentyl. In various embodiments, $G_1$, $G_2$, $G_3$, and $G_4$ are not branched alkyl when Z is —O—. When any one or more of $G_1$, $G_2$, $G_3$, and $G_4$ is alkoxy, it is preferably $C_1$-$C_6$ alkoxy.

In any one or more of the embodiments described above, $L_1$, and $L_2$ are each independently amine, halide, or sulfonate leaving groups. In one embodiment, $L_1$, and $L_2$ are halide leaving groups. For example, $L_1$ and $L_2$ may be independently chloro, fluoro, bromo, or iodo. Alternatively, $L_1$ and $L_2$ may be amine leaving groups. For example, $L_1$ and $L_2$ may be independently cyclic amines or dialkyl amines such as imidazole, diethylamine, diisopropylamine, and the like. In another alternative example, $L_1$ and $L_2$ may be sulfonate leaving groups. For example, $L_1$, and $L_2$ may be independently tosylate, triflate, mesylate, and the like.

In one specific embodiment, therefore, $L_1$, and $L_2$ are halide leaving groups; $G_1$, $G_2$, $G_3$, and $G_4$ are independently substituted or unsubstituted alkyl, alkenyl, alkynyl, aryl, heteroaryl, or cycloalkyl; Z is —(CH$_2$)$_y$—; and y is a positive integer from 1 to about 8.

In another specific embodiment, $L_1$ and $L_2$ are chloro leaving groups; $G_1$, $G_2$, $G_3$, and $G_4$ are independently linear or branched alkyl or alkenyl having from about 1 to about 4 carbon atoms, cycloalkyl having from about 1 to about 6 carbon atoms, or phenyl; Z is —(CH$_2$)$_y$—; and y is a positive integer from 1 to about 4.

In a third specific embodiment, $L_1$, and $L_2$ are halide leaving groups; $G_1$, $G_2$, $G_3$, and $G_4$ are independently substituted or unsubstituted alkyl, alkenyl, alkynyl, aryl, heteroaryl, or cycloalkyl; Z is —[O—Si($Z_{10}$)($Z_{11}$)-]$_n$O— or —O—; n is 1 or 2; and $Z_{10}$, and $Z_{11}$ are alkyl.

In a fourth specific embodiment, $L_1$, and $L_2$ are chloro leaving groups; $G_1$, $G_2$, $G_3$, and $G_4$ are independently linear or branched alkyl or alkenyl having from about 1 to about 4 carbon atoms, cycloalkyl having from about 1 to about 6 carbon atoms, or phenyl; and Z is —O—.

In any one of the four preceding specific embodiments $L_1$, and $L_2$ may be, instead of a halide (or, more specifically, chloro), any other suitable functionally reactive leaving group. For example, $L_1$, may be chloro while $L_2$ could be a different leaving group such as a different halide, amine, or sulfonate leaving group. Alternatively, each of $L_1$ and $L_2$ could be, independently, any other combination of amine, halide, or sulfonate leaving groups.

Certain particularly preferred bridging silicon-based protecting groups are identified in Table 1 (each of which and other suitable bridging silicon-based protecting groups for use in the process of the present invention being commercially available from Gelest, Inc., Morrisville, Pa.):

TABLE 1

| Formula Name | Structure |
|---|---|
| 1,3-dichlorotetramethyldisiloxane | |
| 1,5-dichlorohexamethyltrisiloxane | |
| 1,7-dichlorooctamethyltetrasiloxane | |
| 1,3-dichloro-1,3-diphenyl-1,3-dimethyldisiloxane | |
| 1,3-dichlorotetraphenyldisiloxane | |
| 1,3-divinyl-1,3-dimethyl-1,3-dichlorodisiloxane | |
| 1,1,3,3-tetracyclopenyldichlorodisiloxane | |
| 1,1,3,3-tetraisopropyl-1,3-dichlorodisiloxane | |
| 1,2-bis(chlorodimethylsilyl)ethane | |
| 1,3-bis(chlorodimethylsilyl)propane | |
| 1,6-bis(chlorodimethylsilyl)hexane | |

TABLE 1-continued

| Formula Name | Structure |
|---|---|
| 1,8-bis(chlorodimethylsilyl)octane | |

It will be understood by one of ordinary skill in the art that each of the bridging silicon-based protecting groups identified in Table 1 could have, instead of chloro, other suitable functionally reactive leaving groups attached. to the silyl atom at each end of the bridging silicon-based protecting group. For example, the leaving group at one end could be chloro while the leaving group at the other end could be a different leaving group such as a different halide, amine, or sulfonate leaving group. Alternatively, each of the two leaving groups could be, independently, any other combination of amine, halide, or sulfonate leaving groups.

Upon attachment of an appropriately substituted side chain to the polycyclic fused ring compound and/or other derivatization, described in further detail below, the various protecting groups may then be deprotected by hydrolysis under mild conditions so as not to disturb the ester linkage of the side chain (if present) and/or the other various substituents on the polycyclic fused ring and/or the side chain (if present).

Protection Reaction Mixture And Process Conditions

In general, the reaction mixture comprises the polycyclic fused ring polyol, the bridging silicon-based protecting group compound, solvent, and a base. Suitable solvents include, for example, polar aprotic solvents or ethereal solvents. Suitable polar aprotic solvents include, for example, dimethylformamide; dimethylaniline; dimethyl-2-imidazolidinone; N-methylpyrrolidinone; acetonitrile; 2,2,2-trifluoroethanol; dimethylsulfoxide; dioxane; acetone; ethyl acetate; hexamethylphosphoramide; and the like, and mixtures thereof. One particularly preferred polar aprotic solvent is dimethylformamide. Suitable ethereal solvents include, for example, diethyl ether, dimethoxyethane, methyl-tert-butyl ether, tetrahydrofuran, and the like, and mixtures thereof. One particularly preferred ethereal solvent is tetrahydrofuran.

The temperature at which the process of the present invention is carried out is not narrowly critical. In general, however, it is preferably carried out at room temperature or higher in order for the bridging protection reaction to proceed at a sufficiently high rate.

In general, the base included in the reaction mixture may be an organic (e.g., an amine base) or inorganic base. Preferably, the base is an amine base. Suitable amine bases include, for example, triethylamine; tributylamine; triethylenediamine; N,N-dicyclohexylmethylamine; diisopropylamine; N,N-diisopropylmethylamine; N,N-diisopropylethylamine; N,N-diisopropyl-2-ethylbutylamine; N,N-diisopropyl-3-pentylamine; N,N,N',N'-tetramethyl-1,8-naphthalenediamine; tris(trimethylsilyl)amine; N,N-diethylaniline; N,N-dimethylaniline; 1,1,3,3-tetramethylguanidine; 2-tert-butyl-1,1,3,3-tetramethyl-guanidine; imidazole and imidazole derivatives; 2,6-lutidine; 1,2,2,6,6-pentamethylpiperidine (PMP); 2,2,6,6-tetramethylpiperidine (TMP); pyridine; N,N-4-dimethylaminopyridine (DMAP); 2,4,6-trimethylpyridine; 2,6-di-tert-butyl-4-methylpyridine; 2,4,6-tri-tert-butylpyridine; 1,8-diazabicyclo[5.4.0]undec-7-ene (DBU); 1,5-diazabicyclo[4.3.0]non-5-ene (DBN); 1,4-diazabicyclo(2.2.2)octane (TED); 7-methyl-1,5,7-triazabicyclo(4.4.0)dec-5-ene (MTBD); 3,3,6,9,9-pentamethyl-2,10-diazabicyclo-(4.4.0) dec-1-ene (PMDBD); 1,5,7-triazabicylco(4.4.0) dec-5-ene; quinuclidine; and the like, and mixtures thereof. One particularly preferred amine base is N,N-4-dimethylaminopyridine (DMAP).

In some applications, however, an inorganic base may be desirable. Such bases include, for example, ammonium or alkali or alkaline earth metal hydroxides, carbonates, bicarbonates, and the like, and combinations thereof. Suitable inorganic bases include, for example, sodium hydroxide, potassium hydroxide, ammonium hydroxide, sodium carbonate, potassium carbonate, cesium carbonate, and the like, and mixtures thereof.

As previously noted, the processes described herein may be used with a wide range of polycyclic fused ring polyols, whether obtained from natural or synthetic sources, to prepare a wide variety of protected polycyclic fused ring compounds and intermediate compounds which may then be further derivatized. For example, the processes of the present invention may be effectively used to protect the C(7) and the C(10) hydroxy functional groups of a taxane prior to the coupling reaction between a C(13) side chain precursor and a taxane to introduce a C(13) side chain onto the taxane.

Deprotection

Deprotection of the protected polycyclic fused ring compound generally comprises treating the protected polycyclic fused ring compound with a hydrolyzing agent. Preferably, the hydrolyzing agent is any mild hydrolyzing agent that will not disturb the ester linkage of the side chain (if present) and/or the other various substituents on the polycyclic fused ring compound and/or the side chain. Suitable hydrolyzing agents include organic and inorganic acids, bases, and alcohols.

Exemplary organic acids include, for example, organic acids selected from aliphatic, cycloaliphatic, aromatic, araliphatic, heterocyclic, carboxylic and sulfonic classes of organic acids such as, for example, acetic, adipic, algenic, aminobenzoic, anthranilic, ascorbic, aspartic, benzenesulfonic, benzoic, boric, butyric, citric, cyclohexylaminosulfonic, embonic (pamoic), ethanesulfonic, formic, fumaric, galactaric, galacturonic, gluconic, glucuronic, glutamic, glutaric, glycolic, hydroxyacetic, hydroxybutyric, 4-hydroxybenzoic, 2-hydroxyethanesulfonic, hydroxypropionic, lactic, levulinic, maleic, malic, malonic, mandelic, mesylic, methanesulfonic, methylbenzoic, nitrobenzoic, naphthalenesulfonic, pantothenic, phenylacetic, phosphonic, phytic, propionic, pyruvic, salicylic, sorbic, stearic, succinic, sulfamic, sulfanilic, tartaric, toluenesulfonic, trichloroacetic, trifluoroacetic acids, and the like, and mixtures thereof.

Exemplary inorganic acids include, for example, hydrogen halides (such as hydrochloric acid, hydrobromic acid, hydrofluoric acid, hydroiodic acid, and tetrafluoroboric acid), carbonic acid, nitric acid, perchloric acid, phosphoric acid, sulfuric acid, and the like, and mixtures thereof.

In one embodiment, the protected polycyclic fused ring compound may be treated with the hydrolyzing agent in the presence of a polar aprotic solvent. Suitable polar aprotic solvents include, for example, dimethylformamide; dimethylaniline; dimethyl-2-imidazolidinone; N-methylpyrrolidinone; acetonitrile; 2,2,2-trifluoroethanol; dimethylsulfoxide; dioxane; acetone; ethyl acetate; hexamethylphosphoramide; and the like, and mixtures thereof. Particularly preferred polar aprotic solvents include dimethylformamide and acetonitrile.

In another embodiment, the protected polycyclic fused ring compound may be treated with the hydrolyzing agent in the presence of an ethereal solvent. Suitable ethereal solvents include, for example, diethyl ether, dimethoxyethane, methyl-tert-butyl ether, tetrahydrofuran, and the like, and mixtures thereof. One particularly preferred ethereal solvent is tetrahydrofuran.

The bridging silicon-based protecting group may be completely removed (i.e., deprotected) from the two hydroxy groups on the polycyclic fused ring compound the bridging silicon-based protecting group is protecting. Alternatively, the protected polycyclic fused ring compound may be selectively deprotected at only one of the two hydroxy groups the bridging silicon-based protecting group is protecting. For example, a 7,10-protected polycyclic fused ring compound may be selectively deprotected only at C(10), while C(7) remains protected with the silicon-based protecting group, and vice versa. The unprotected hydroxy group may then undergo further derivatization, described in further detail below.

To selectively deprotect the bridging silicon-based protecting group, the protected polycyclic fused ring compound is preferably treated with an alcohol or a mixture of alcohols in the presence of a base. Preferably, the alcohol corresponds to the formula $R_{104}OH$, wherein $R_{104}$ is hydrocarbyl. More preferably, $R_{104}$ is alkyl. Still more preferably, the alcohol is methanol. Suitable bases include triethyl amine, sodium carbonate, or sodium bicarbonate. Particularly preferred bases include triethyl amine and sodium bicarbonate. The solvent for the selective deprotection can be an alcohol, acetonitrile, tetrahydrofuran, methylene chloride, or combinations thereof; preferably, the solvent is methanol.

The temperature at which the process for the deprotection of the protected polycyclic fused ring compound is carried out is not narrowly critical. In general, however, it is preferably carried out at room temperature or higher in order for the deprotection reaction to proceed at a sufficiently high rate.

Further Derivatization

The attachment of a C(13) side chain precursor to a protected polycyclic fused ring compound may be carried out using a variety of known techniques. For example, a side chain precursor such as an appropriately substituted β-lactam, oxazinone, oxazoline, oxazoline carboxylic acid, oxazoline carboxylic acid anhydride, or isoserine derivative may be reacted with a protected polycyclic fused ring compound having a C(13) hydroxy, metallic oxide, or ammonium oxide substituent to form compounds having, for example, a β-amido ester substituent at C(13).

Exemplary side chain precursors which may be attached at C(13) of the protected polycyclic fused ring compounds include those corresponding to any of Formulae (5), (6), (7A), (7B), (7C), and (8):

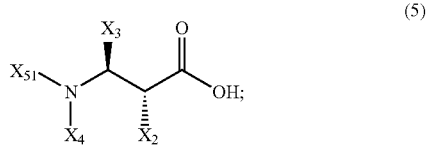

(5)

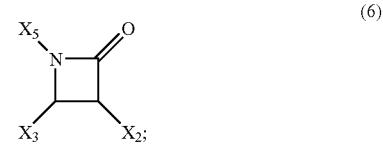

(6)

-continued

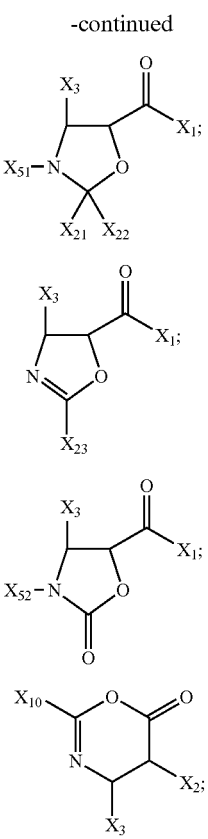

(7A)

(7B)

(7C)

(8)

wherein $X_1$, is hydroxy, thio, or $SX_{10}$;

$X_2$ is alkyl, alkenyl, alkynyl, aryl, heterocyclo, —$OX_6$, —$SX_7$, or —$NX_8X_9$;

$X_3$ is substituted or unsubstituted alkyl, alkenyl, alkynyl, phenyl, or heterocyclo;

$X_4$ is hydrogen or an amino protecting group;

$X_5$ is —$COX_{10}$, —$COOX_{10}$, or —$CONHX_{10}$;

$X_6$ is acyl, alkyl, alkenyl, alkynyl, aryl, heteroaryl, hydrogen, or hydroxy protecting group;

$X_7$ is alkyl, alkenyl, alkynyl, aryl, heteroaryl, or sulfhydryl protecting group;

$X_8$ is hydrogen, hydrocarbyl, substituted hydrocarbyl, or heterocyclo;

$X_9$ is an amino protecting group;

X10 is hydrocarbyl, substituted hydrocarbyl, or heterocyclo;

$X_{11}$ is unsubstituted or substituted aryl;

$X_{21}$ and $X_{22}$ are hydrocarbyl;

$X_{23}$ is aryl;

$X_{51}$ is amino protecting group; and $X_{52}$ is hydrogen, —$COX_{10}$, —$COOX_{10}$, or —$CONHX_{10}$.

One example of the attachment of a suitable side chain precursor to a polycyclic fused ring compound is illustrated by Denis et al., U.S. Pat. No. 4,924,011 (incorporated herein by reference). There, an isoserine side chain precursor generally corresponding to Formula (5) is attached to the C(13) hydroxy group of protected baccatin III in the presence of a condensing agent, such as dicyclohexylcarbodiimide (DCC), and an activating agent, such as N,N-4-dimethylaminopyridine (DMAP), working in an aromatic solvent. See, for example, Denis et al., U.S. Pat. No. 4,924,011 at column 2, lines 5-68.

Another example of the attachment of a suitable side chain precursor to a polycyclic fused ring compound is illustrated by Holton et al., U.S. Pat. No. 5,466,834 (incorporated herein by reference). There, protected baccatin III, or 10-DAB, or other 10-DAB derivative is reacted with a C(13) deprotonating agent such as an organometallic compound (e.g., n-butyllithium or n-hexyllithium) or a disilazide (e.g., NaHMDS or LHMDS) in the presence of a solvent such as tetrahydrofuran (THF) to form a metal alkoxide (e.g., 13-O-lithium-7-O-triethylsilyl baccatin III), followed by the reaction with a β-lactam side chain precursor generally corresponding to Formula (6) in the presence of THF. See, for example, Holton et al., U.S. Pat. No. 5,466,834 at columns 12-14.

Another example of the attachment of a suitable side chain precursor to a polycyclic fused ring compound is illustrated by Holton, U.S. Pat. No. 5,430,160 (incorporated herein by reference). There, protected baccatin III, or 10-DAB, or other 10-DAB derivative is reacted with an ammonium-containing compound (e.g., a tetraalkylammonium halide) in the presence of a solvent such as tetrahydrofuran (THF) to form an ammonium alkoxide, followed by the reaction with a β-lactam side chain precursor generally corresponding to Formula (6) in the presence of THF. See, for example, Holton, U.S. Pat. No. 5,430,160 at columns 11-14.

Alternatively, a suitable side chain may be attached without the use of an organometallic compound, a disilazide, or an ammonium-containing compound, such as by the method described by Holton et al., U.S. Pat. No. 5,175,315 (incorporated herein by reference). There, protected baccatin III, or 10-DAB, or 10-DAB derivative is reacted with a β-lactam side chain precursor generally corresponding to Formula (6) in the presence of an activating agent, preferably a tertiary amine such as triethyl amine, diisopropyl amine, pyridine, N-methyl imidazole, and N,N-4-dimethylaminopyridine (DMAP). See, for example, Holton et al., U.S. Pat. No. 5,175, 315 at columns 10-11.

Another example of the attachment of a suitable side chain precursor to a polycyclic fused ring compound is illustrated by Commercon et al. (Tetrahedron Letters, 1992, 33, 36, 5185-5188). There, protected baccatin III, or 10-DAB, or 10-DAB derivative is esterified with an oxazoline side chain precursor generally corresponding to Formula (7A) in the presence of N,N-4-dimethylaminopyridine (DMAP), dicyclohexylcarbodiimide (DCC), and toluene. See, for example, Tetrahedron Letters, 1992, 33, 36, 5187.

Yet another example of the attachment of a suitable side chain precursor is illustrated by Chanteloup et al., U.S. Pat. No. 6,825,365 (incorporated herein by reference). There, protected baccatin III, or 10-DAB, or 10-DAB derivative is esterified with an oxazoline side chain precursor generally corresponding to Formulae (7B) or (7C) in the presence of N,N-4-dimethylaminopyridine (DMAP), dicyclohexylcarbodiimide (DCC), and toluene. The oxazoline side chain precursors corresponding to Formulae (7B) and (7C) attach at the C(13) position without the opening of the oxazoline ring. After attachment, the oxazoline ring may be opened by hydrolysis in acidic or basic medium. See, for example, Chanteloup et al., U.S. Pat. No. 6,825,365 at columns 10-16.

Yet another example of the attachment of a suitable side chain precursor is illustrated by Holton, U.S. Pat. No. 5,015, 744 (incorporated herein by reference). There, protected baccatin III, or 10-DAB, or 10-DAB derivative is reacted with an oxazinone side chain precursor generally corresponding to Formula (8) in the presence of N,N-4-dimethylaminopyridine (DMAP) and pyridine. See, for example, Holton, U.S. Pat. No. 5,015,744 at columns 10-11.

Once a suitable side chain is attached, the bridging silicon-based protecting group may be removed according to the processes described herein, and the various substituent groups on the polycyclic fused ring may be further protected and/or derivatized. For example, the processes described herein may be utilized to simultaneously protect the C(7) and C(10) hydroxy groups of a taxane, attach a suitable side chain at the C(13) position of the taxane, remove the bridging silicon-based protecting group from the hydroxy substituents on the polycyclic fused ring polyol, and further prepare taxanes having alternative substituents at various locations on the taxane nucleus, such as the C(1), C(2), C(4), C(6), C(7), C(9), C(10), or C(14) positions, or at various locations on the C(13) side chain, such as the 1', 2', 3', 4', or 5' positions, discussed in further detail below.

Alternatively, one of the hydroxy substituents protected by the bridging silicon-based protecting group may be selectively deprotected prior to or after the attachment of a suitable side chain at the C(13) position of the taxane, followed by the further derivatization of various substituents on the taxane nucleus and/or the side chain, discussed in further detail below.

Reaction Scheme 1 illustrates the simultaneous protection of a polycyclic fused ring polyol with a bridging silicon-based protecting group, followed by the attachment of a side chain. Once a side chain has been attached to the protected polycyclic fused ring compound, the bridging silicon-based protecting group may be partially or completely removed and the polycyclic fused ring compound and/or side chain may be further protected and/or derivatized.

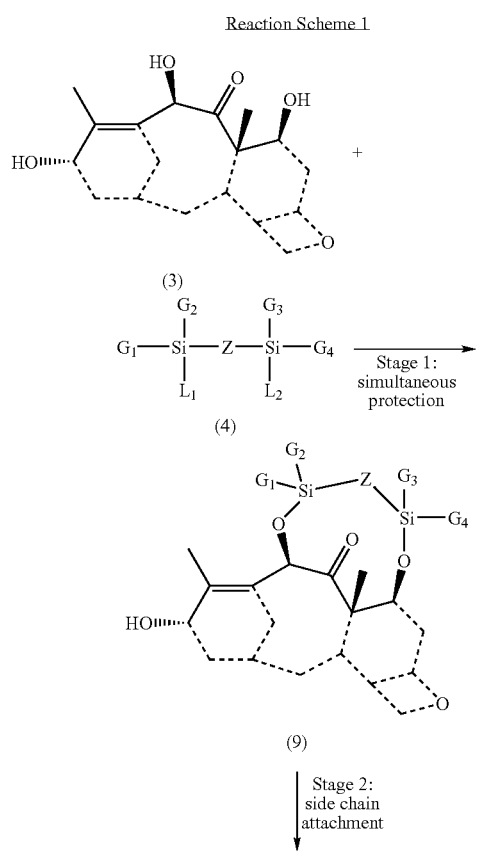

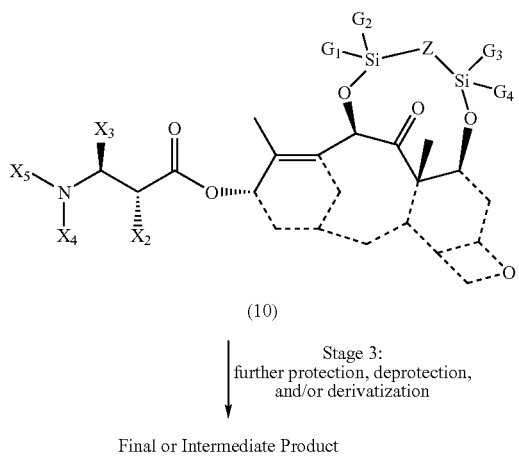

Stage 3: further protection, deprotection, and/or derivatization

Final or Intermediate Product

Stage 1 of Reaction Scheme 1 illustrates the simultaneous protection of polycyclic fused ring polyol (3) with a bridging silicon-based protecting group (4). The dashed lines in polycyclic fused ring polyol (3) denote the skeletal structure of the polycyclic fused ring polyol. Any polycyclic fused ring polyol described herein may be utilized in Stage 1. For example, in one embodiment the polycyclic fused ring polyol corresponds to Formula (13):

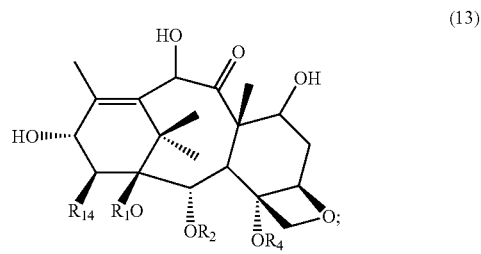

wherein $R_1$ is hydrogen, acyl, or together with $R_2$ or $R_{14}$ forms carbonate, acetal, or ketal;

$R_2$ is hydrogen, acyl, or together with $R_1$ or $R_{14}$ forms carbonate, acetal, or ketal;

$R_4$ is hydrogen, acyl, or together with $R_2$ forms carbonate, acetal, or ketal; and $R_{14}$ is hydrogen, hydroxy, or together with $R_1$ or $R_2$ forms carbonate, acetal, or ketal.

In one preferred embodiment, the polycyclic fused ring polyol (3) of Reaction Scheme 1 is 10-DAB, that is, the polycyclic fused ring polyol corresponds to Formula (13), wherein $R_1$ is hydrogen, $R_2$ is benzoyl, $R_4$ is acetyl, and $R_{14}$ is hydrogen. In another preferred embodiment, the polycyclic fused ring polyol (3) of Reaction Scheme 1 is 14-β-hydroxy-10-DAB, that is, the polycyclic fused ring polyol corresponds to Formula (13), wherein $R_1$ is hydrogen, $R_2$ is benzoyl, $R_4$ is acetyl, and $R_{14}$ is hydroxy.

In a particularly preferred embodiment, the polycyclic fused ring polyol is 10-DAB and corresponds to Formula (23):

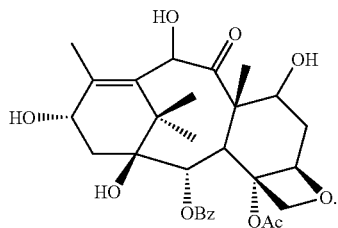

(23)

Any bridging silicon-based protecting group described herein may be utilized in Stage 1 of Reaction Scheme 1. For example, in one embodiment $G_1$, $G_2$, $G_3$, and $G_4$ are independently substituted or unsubstituted alkyl, alkenyl, alkynyl, aryl, heteroaryl, or cycloalkyl; Z is —$(CH_2)y$—; and y is a positive integer from about 1 to about 8. In another embodiment, $G_1$, $G_2$, $G_3$, and $G_4$ are independently substituted or unsubstituted alkyl, alkenyl, alkynyl, aryl, heteroaryl, or cycloalkyl; Z is —[O—Si($Z_{10}$)($Z_{11}$)-]$_n$O— or —O—; n is 1 or 2; and $Z_{10}$ and $Z_{11}$ are alkyl. In either of these two embodiments, $L_1$ and $L_2$ are independently amine, halide, or sulfonate leaving groups.

Stage 1 of Reaction Scheme 1 is preferably carried out in the presence of a base and a solvent. Suitable bases include, for example, an amine base, such as N,N-4-dimethylaminopyridine (DMAP), and suitable solvents include, for example, polar aprotic solvents, such as dimethylformamide (DMF). Alternatively, however, in other embodiments other bases and solvents, such as inorganic bases and/or ethereal solvents, for example, may be preferred.

Stage 2 of Reaction Scheme 1 illustrates the attachment of a side chain at the C(13) position of the 7,10-protected polycyclic fused ring compound (9). In general, a range of side chain precursors may be utilized in Stage 2.

In one embodiment, the side chain precursor is a β-lactam (e.g., Formula (6)) or an oxazinone (e.g., Formula (8)). In this embodiment, it is generally preferred that the C(13) position of 7,10-protected polycyclic fused ring compound (9) be substituted by MO— wherein M is a metal or ammonium (i.e., the polycyclic fused ring compound is reacted with a deprotonating agent (such as an organometallic compound (e.g., n-butyllithium or n-hexyllithium) or a disilazide (e.g., NaHMDS or LHMDS) or an amine or ammonium-containing compound (such as a tetraalkylammonium halide or an alkali metal dialkyl amine), as described in detail herein). Alternatively, however, the C(13) position of 7,10-protected polycyclic fused ring compound (9) may be hydroxy (i.e., M is hydrogen) and compound (9) may be reacted with the β-lactam in the presence of a tertiary amine such as triethyl amine, diisopropyl amine, pyridine, N-methyl imidazole, and N,N-4-dimethylaminopyridine (DMAP).

In another embodiment, the side chain precursor is an isoserine derivative (e.g., Formula (5)) or an oxazoline, oxazoline carboxylic acid, or oxazoline carboxylic acid anhydride (e.g., Formulae (7A), (7B), or (7C)). In this embodiment, it is generally preferred that the C(13) position of 7,10-protected polycyclic fused ring compound (9) be hydroxy (i.e., M is hydrogen) and prior to reaction with the isoserine derivative or the oxazoline, oxazoline carboxylic acid, or oxazoline carboxylic acid anhydride, the polycyclic fused ring compound (9) is treated with an activating agent such as di(2-pyridyl) carbonate or dicyclohexylcarbodiimide (DCC) in the presence of an amine base catalyst such as N,N-4-dimethylaminopyridine (DMAP) or pyridine. Alternatively, however, the C(13) position of 7,10-protected polycyclic fused ring compound (9) may be substituted by MO— wherein M is a metal or ammonium (i.e., the polycyclic fused ring compound is reacted with a deprotonating agent (such as an organometallic compound (e.g., n-butyllithium or n-hexyllithium) or a disilazide (e.g., NaHMDS or LHMDS) or an amine or ammonium-containing compound (such as a tetraalkylammonium halide or an alkali metal dialkyl amine), as described in detail herein).

In either of the two embodiments described above (i.e., when the side chain precursor is a β-lactam (e.g., Formula (6)), an oxazinone (e.g., Formula (8)), an isoserine derivative (e.g., Formula (5)), or an oxazoline, oxazoline carboxylic acid, or oxazoline carboxylic acid anhydride (e.g., Formulae (7A), (7B), or (7C)), when the C(13) position of 7,10-protected polycyclic fused ring compound (9) is substituted by MO—, the polycyclic fused ring compound corresponds to Formula ($9_M$):

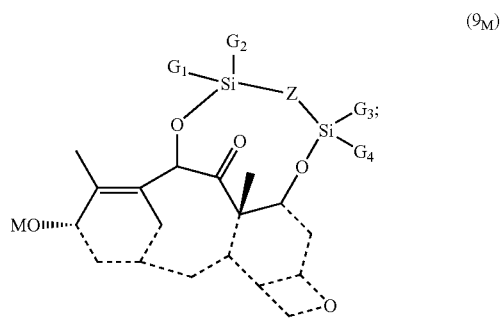

($9_M$)

wherein M is metal, ammonium, or hydrogen; $G_1$, $G_2$, $G_3$, $G_4$, and Z are as defined in connection with Formula (4); and the dashed lines denote the skeletal structure of the polycyclic fused ring compound.

In various embodiments, the 7,10-protected derivative corresponding to Formula ($9^R$) can be prepared

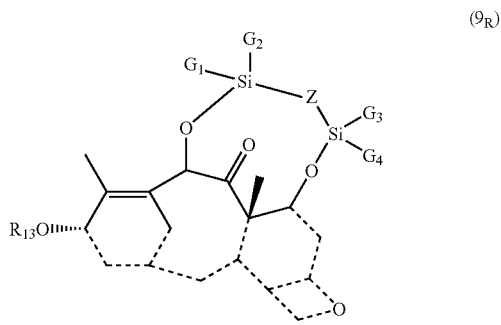

($9_R$)

wherein $R_{13}$ is hydrogen or has the structure

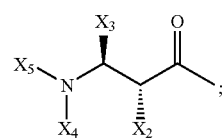

$G_1$, $G_2$, $G_3$, $G_4$, and Z are as defined in connection with Formula (4); $X_2$, $X_3$, $X_4$, and $X_5$ are as defined in connection with Formulae (5), (6), (7A), (7B), (7C), and (8); and the dashed lines denote the skeletal structure of the polycyclic fused ring compound. Formula $9^R$ can be further derivatized at the C(13) position to produce compounds corresponding to Formula $9_{R13}$ wherein $R_{13}$ is hydrogen, hydroxy protecting group, a metal, comprises ammonium, or has the structure

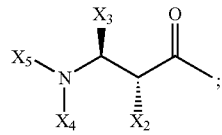

wherein $X_2$, $X_3$, $X_4$, and $X_5$ are as defined in connection with Formulae (5), (6), (7A), (7B), (7C), and (8).

In Stage 3 of Reaction Scheme 1, 7,10-protected polycyclic fused ring compound (10) is deprotected to yield a final product or derivatized further and then deprotected to yield a final product. For example, the 7,10-protecting group may be removed by hydrolysis under relatively mild conditions so as not to disturb the C(13) ester linkage and/or other hydrolyzable substituents on the polycyclic fused ring and/or the side chain. A range of hydrolyzing agents may be used for this purpose, including organic and inorganic acids, bases, and alcohols. In one embodiment, for example, hydrofluoric acid (HF) or hydrochloric acid (HCl) may be used to remove all of the hydroxy protecting groups without disturbing the C(13), C(2), or C(4) ester linkages. Alternatively, it may be desirable to selectively remove certain protecting groups (such as deprotecting or selectively deprotecting the bridging silicon-based protecting group at C(7) and/or C(10)) while leaving other protecting groups (such as those on the C(13) side chain), in order to further protect and/or derivatize C(7), C(10), or any other position on the polycyclic fused ring compound and/or the side chain.

Depending upon the nature of the substituents carried by the polycyclic fused ring compound (9) and the nature of the substituents carried by the side chain precursor (e.g., one of Formulae (5), (6), (7A), (7B), (7C) and (8)), various taxane derivatives may be formed upon deprotection and/or selective deprotection and derivatization in Stage 3. For example, when $R_1$ is hydrogen, $R_2$ is benzoyl, $R_4$ is acetyl, $R_{14}$ is hydrogen, $X_2$ is —$OX_6$, $X_3$ is phenyl,)$X_4$ is hydrogen, $X_5$ is tert-butoxycarbonyl, and $X_6$ is a hydroxy protecting group (e.g., 2-methoxy-2-propyl), upon deprotection of the C(2') hydroxy group and the bridging silicon-based protecting group at C(7) and C(10) in Stage 3 of Reaction Scheme 1, docetaxel is formed from polycyclic fused ring compound (10). By way of further example, when $R_1$ is hydrogen, $R_2$ is benzoyl, R4 is acetyl, $R_{14}$ is hydrogen, $X_2$ is —$OX_6$, $X_3$ is phenyl, $X_4$ is hydrogen, $X_5$ is benzoyl, and $X_6$ is a hydroxy protecting group, upon deprotection of the C(2') hydroxy group and the bridging silicon-based protecting group at C(7) and C(10) in Stage 3 of Reaction Scheme 1, 10-deacetyl taxol (10-deacetyl paclitaxel) is formed from polycyclic fused ring compound (10).

One preferred embodiment of the present invention is illustrated in Reaction Scheme 1A wherein $G_1$, $G_2$, $G_3$, $G_4$, $L_1$, $L_2$, and Z are as defined in connection with Formula (4); $R_1$, $R_2$, $R_4$, and $R_{14}$ are as defined in connection with Formula (13); and $X_2$ $X_3$, $X_4$, and $X_5$ are as defined in connection with the side chain precursor of Formula (6).

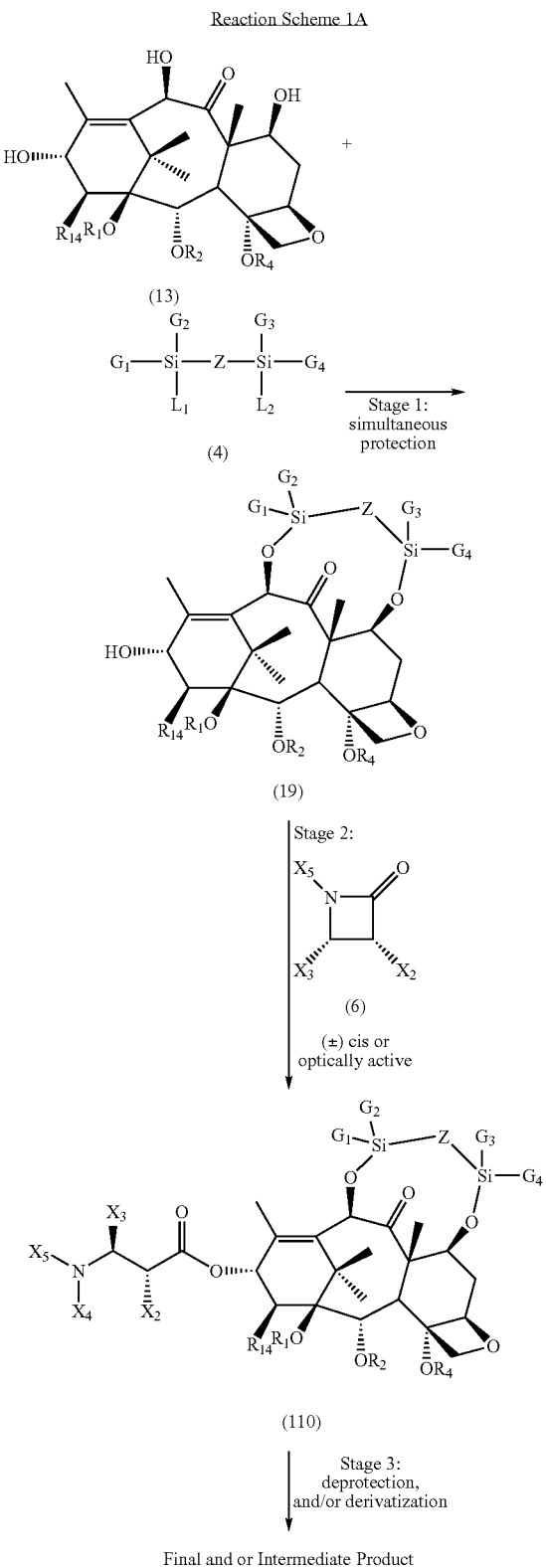

In Reaction Scheme 1A, polycyclic fused ring polyol (13) is treated with a bridging silicon-based protecting group (4) to yield 7,10-protected fused ring compound (19). As illustrated, a side chain is attached to the C(13) position of compound (19) using a β-lactam (6) as described herein; alternatively, however, other side chain precursors such as an oxazinone, oxazoline, oxazoline carboxylic acid, oxazoline carboxylic acid anhydride, or isoserine derivative may be used instead. As described herein, the C(13) position of polycyclic fused ring compound (19) is preferably substituted with MO— in the side chain attachment stage, thus the polycyclic fused ring compound corresponds to Formula ($19_M$):

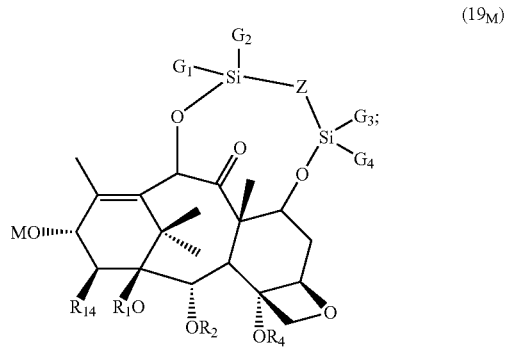

wherein M is metal, ammonium, or hydrogen; $G_1$, $G_2$, $G_3$, $G_4$, and Z are as defined in connection with Formula (4); and $R_1$, $R_2$, $R_4$, and $R_{14}$ are as defined in connection with Formula (13).

In Stage 3 of Reaction Scheme 1A, 7,10-protected polycyclic fused ring compound (110) is deprotected to yield a final product or derivatized further and then deprotected to yield a final product. For example, the 7,10-protecting group may be removed by hydrolysis under relatively mild conditions so as not to disturb the C(13) ester linkage and/or other hydrolyzable substituents on the polycyclic fused ring compound. Alternatively, it may be desirable to selectively remove certain protecting groups (such as deprotecting or selectively deprotecting the bridging silicon-based protecting group at C(7) and/or C(10)) while leaving other protecting groups (such as those on the C(13) side chain), in order to further protect and/or derivatize C(7), C(10), or any other position on the polycyclic fused ring compound and/or the side chain.

Rather than removing all of the hydroxy protecting groups simultaneously in Stage 3 of Reaction Schemes 1 and 1A, it may be desirable to selectively deprotect certain hydroxy protecting groups while leaving other hydroxy protecting groups attached to the polycyclic fused ring compound. The unprotected hydroxy protecting group may then undergo further derivatization using various techniques known in the art. For example, it may be desirable to selectively deprotect and derivatize the C(10) position after the C(13) side chain has been attached. Alternatively, it may be desirable to selectively deprotect and derivatize the C(10) position before the C(13) side chain is attached. This strategy is generically illustrated in Reaction Scheme 2 wherein $G_1$, $G_2$, $G_3$, $G_4$, $L_1$, $L_2$, and Z are as defined in connection with Formula (4); $X_2$, $X_3$, X4, $X_5$, and $X_{51}$ are as defined in connection with the side chain precursor selected from Formulae (5), (6), (7A), (7B), (7C), and (8); and the dashed lines in polycyclic fused ring polyol (3) denote the skeletal structure of the polycyclic fused ring polyol.

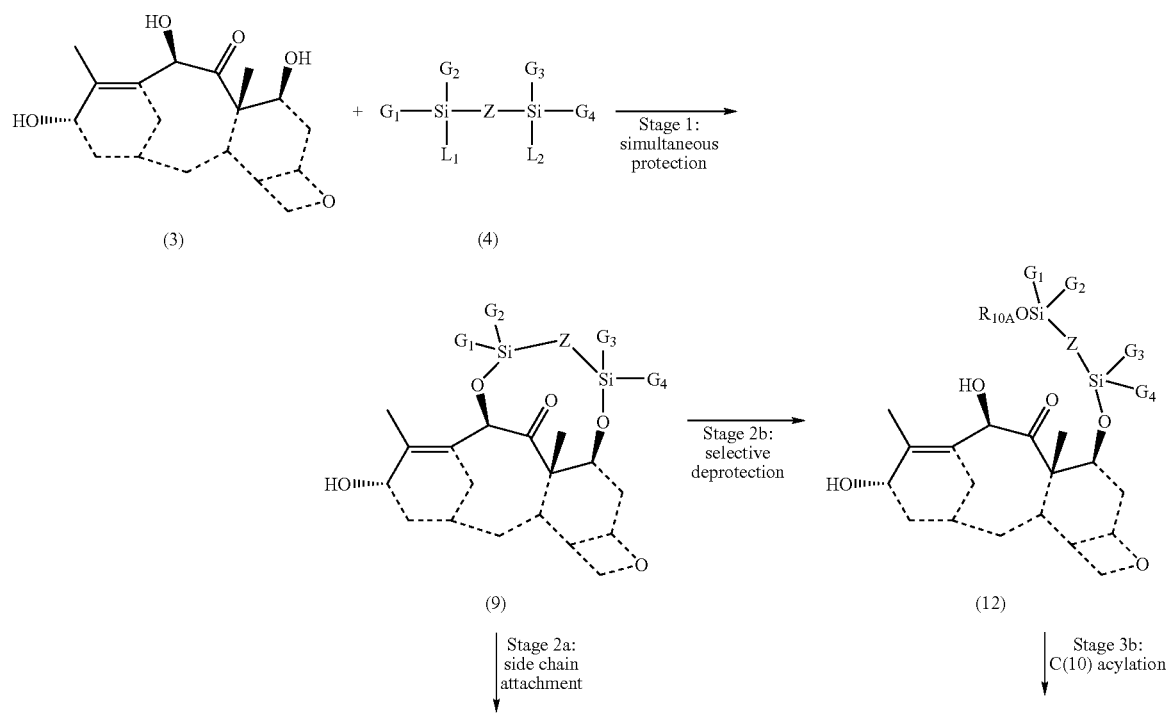

Reaction Scheme 2

-continued

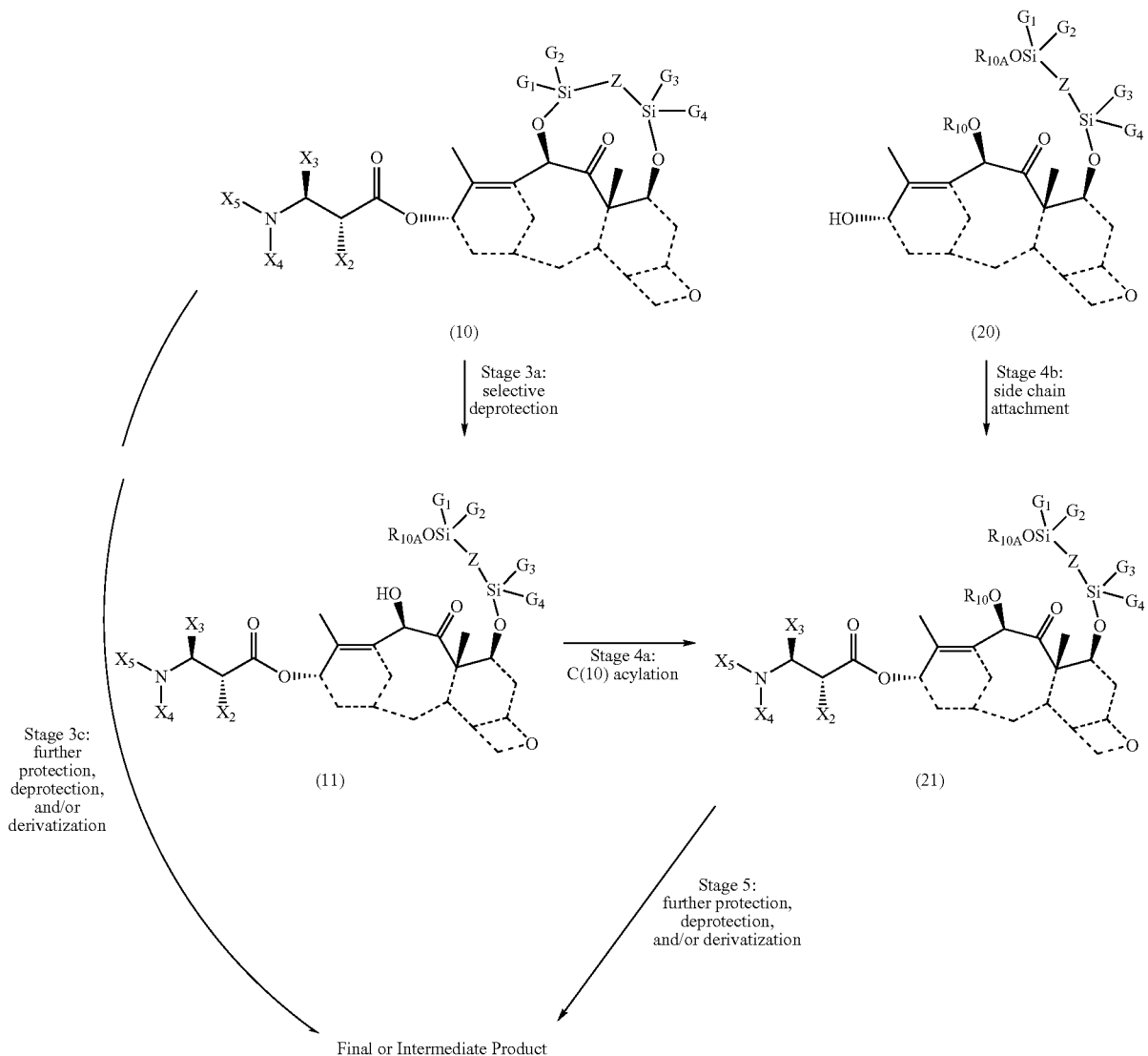

Final or Intermediate Product

Stage 1 of Reaction Scheme 2 illustrates the simultaneous protection of polycyclic fused ring polyol (3) with a bridging silicon-based protecting group (4). Any polycyclic fused ring polyol described herein may be utilized as a starting material in Stage 1 of Reaction Scheme 2 including, for example, those corresponding to Formulae (13) or (23). Similarly, any bridging silicon-based protecting group described herein may be utilized, and the reagents and conditions for the attachment of the bridging silicon-based protecting group to the polycyclic fused ring polyol are the same as those described in connection with Stage 1 of Reaction Schemes 1 and 1A. Following the protection of C(7) and C(10) with the bridging silicon-based protecting group (4), the 7,10-protected compound (9) may be derivatized according to several synthetic pathways.

In Stage 2a of Reaction Scheme 2, a side chain is attached to the C(13) position of 7,10-protected compound (9) using a side chain precursor selected from one of Formulae (5), (6), (7A), (7B), (7C), and (8) to form compound (10). As described herein, the C(13) position of compound (9) is preferably substituted with MO— in the side chain attachment stage, thus compound (9) corresponds to Formula $(9_M)$. In Stage 3a, compound (10) can be selectively deprotected at C(10) using an alcohol (e.g., $R_{10A}OH$ wherein $R_{10A}$ is hydrocarbyl; preferably alkyl) or a mixture of alcohols in the presence of a base to form 7-protected derivative (11). Preferably, the alcohol used in the C(10) deprotection is methanol. Suitable bases for the C(10) deprotection are triethyl amine, sodium carbonate, or sodium bicarbonate; preferably, the base is triethyl amine or sodium bicarbonate. The solvent for C(10) deprotection can be an alcohol, acetonitrile, tetrahydrofuran, methylene chloride, or combinations thereof; preferably, the solvent is methanol. The C(10) deprotection is followed by acylation at C(10) in Stage 4a to form 10-acyl-7-protected derivative (21) (i.e., $R_{10}$ is acyl). By way of an alternative pathway, compound (10) may be deprotected to yield a final product or derivatized further and then deprotected to yield a final product without selectively deprotecting C(10), as generally described in Reaction Schemes 1 and 1A and as illustrated in Stage 3c of Reaction Scheme 2.

In Stage 2b of Reaction Scheme 2, compound (9) is selectively deprotected at C(10) to form 7-protected derivative (12) prior to the attachment of the side chain at C(13). The reagents and conditions for selective deprotection are the same as described in connection with Stage 3a above. The C(10) deprotection is followed by C(10) acylation in Stage 3b to form 10-acyl-7-protected derivative (20) (i.e., $R_{10}$ is acyl). A side chain is then attached to the C(13) position of derivative (20) in Stage 4b using a side chain precursor selected from one of Formulae (5), (6), (7A), (7B), (7C), and (8) to form 10-acyl-7-protected derivative (21). As described herein, the C(13) position of compound (13) is preferably substituted with MO— in the side chain attachment stage, thus compound (20) corresponds to Formula $(20_M)$:

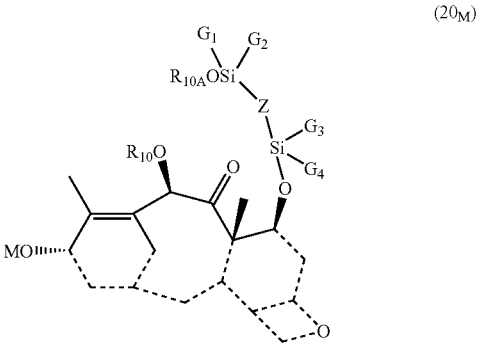

(20$_M$)

wherein M is metal, ammonium, or hydrogen; $G_1$, $G_2$, $G_3$, $G_4$, and Z are as defined in connection with Formula (4); and the dashed lines denote the skeletal structure of the polycyclic fused ring compound.

The above process can be used to prepare the 10-hydroxy-7-protected compound corresponding to Formula $(20_R)$:

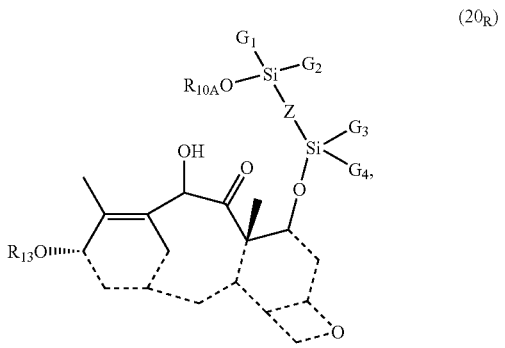

(20$_R$)

and, in turn, compound $(20_R)$ can be acylated at the C(10) position to form the 10-acyl-7-protected compound corresponding to Formula $(20_{R10})$:

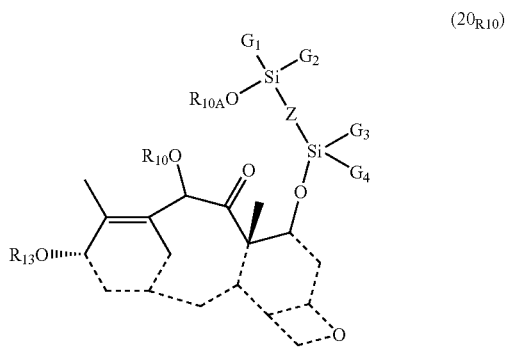

(20$_{R10}$)

wherein $R_{10}$ is acyl, $R_{10A}$ is hydrocarbyl; $R_{13}$ is hydrogen or has the structure

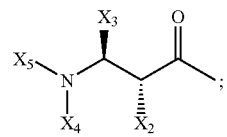

;

$G_1$, $G_2$, $G_3$, $G_4$, and Z are as defined in connection with Formula (4); $X_2$, $X_3$, $X_4$, and $X_5$ are as defined in connection with Formulae (5), (6), (7A), (7B), (7C), and (8) and the dashed lines denote the skeletal structure of the polycyclic fused ring compound. In preferred embodiments, compounds corresponding to Formula $(30_R)$ have the structure of $(20_R)$ at the C(7), C(9), C(10), and C(13), and a structure similar to structure (13) wherein the dashed lines denoting the skeletal structure of the polycyclic fused ring are substituted by $R_1$, $R_2$, $R_4$, and $R_{14}$. Further, more preferably, compounds corresponding to Formula $(40_R)$ have the structure of Formula $(30_R)$ wherein $R_1$, $R_2$, $R_4$, and $R_{14}$ conform to the substituents of 10-DAB.

In Stage 5 of Reaction Scheme 2, derivative (21) (produced from either derivative (11) in Stage 4a or derivative (20) in Stage 4b) is deprotected to yield a final product or derivatized further and then deprotected to yield a final product. For example, the various protecting groups may be removed by hydrolysis under relatively mild conditions so as not to disturb the C(13) ester linkage and/or other hydrolyzable substituents on the polycyclic fused ring compound and/or the side chain.

One preferred embodiment of the present invention is illustrated in Reaction Scheme 2A wherein $G_1$, $G_2$, $G_3$, $G_4$, $L_1$, $L_2$, and Z are as defined in connection with Formula (4); $R_1$, $R_2$, $R_4$, and $R_{14}$ are as defined in connection with Formula (13); and $X_2$, $X_3$, $X_4$, and $X_5$ are as defined in connection with the side chain precursor of Formula (6).

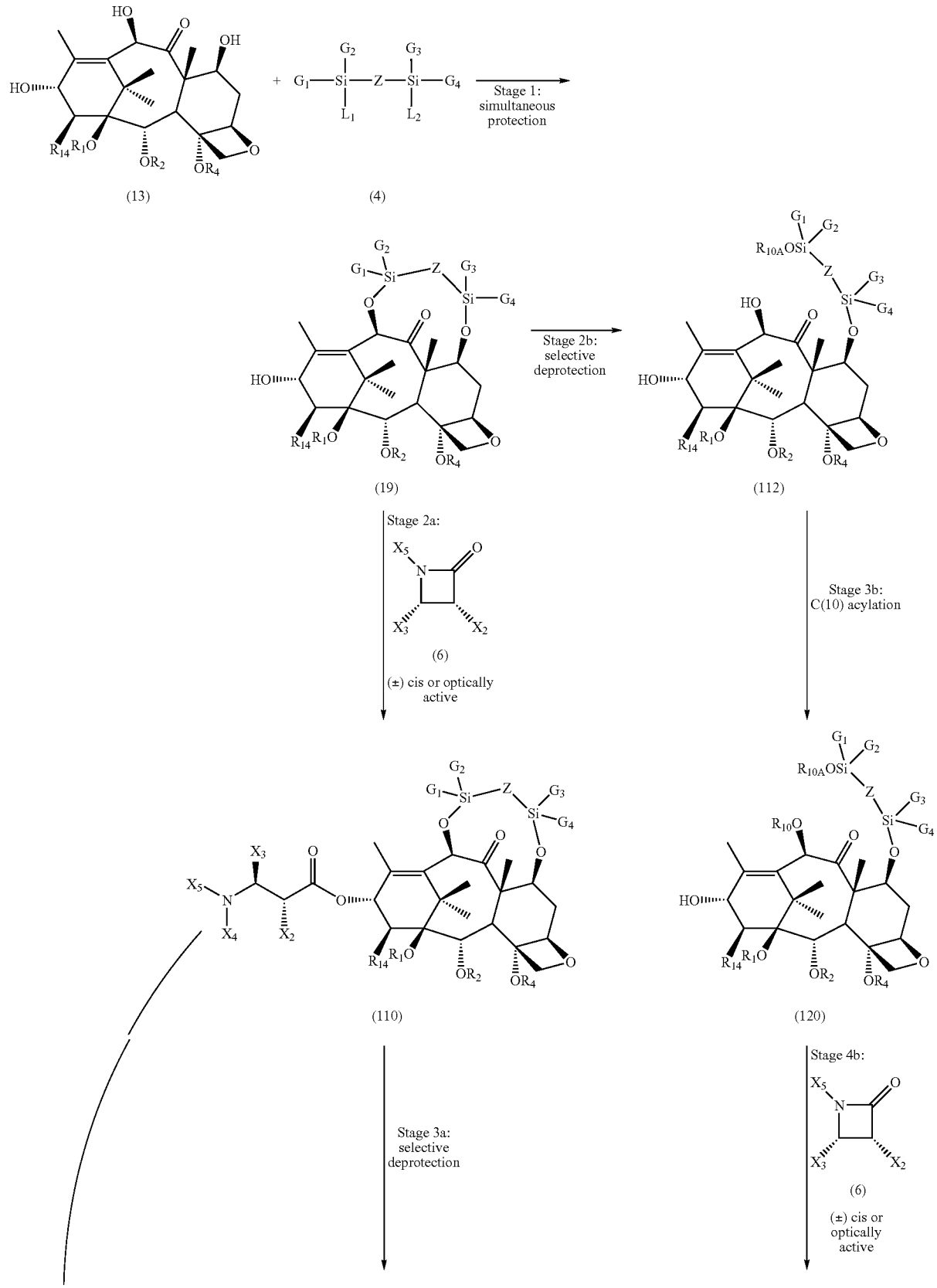

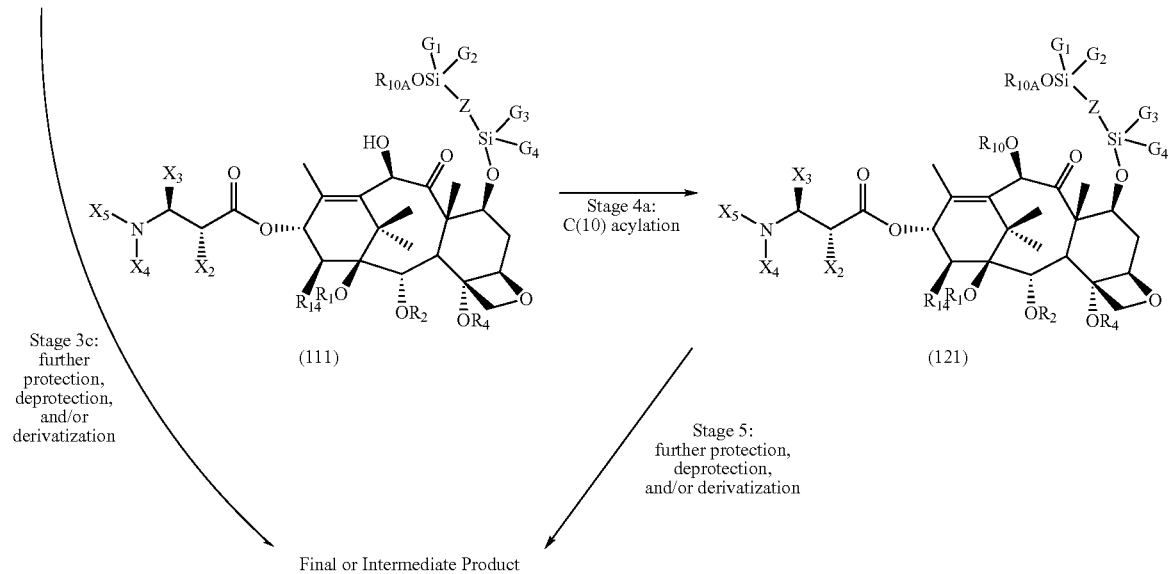

In Reaction Scheme 2A, polycyclic fused ring polyol (13) is treated with bridging silicon-based protecting group (4) according to the processes described herein to yield 7,10-protected compound (19). Following the protection of C(7) and C(10) with the bridging silicon-based protecting group (4), the 7,10-protected compound (19) may be derivatized according to several synthetic pathways.

In Stage 2a of Reaction Scheme 2A, a side chain is attached to the C(13) position of compound (19) using a β-lactam as described herein; alternatively, however, other side chain precursors such as an oxazinone, oxazoline, oxazoline carboxylic acid, oxazoline carboxylic acid anhydride, or isoserine derivative may be used instead. As described herein, the C(13) position of compound (19) is preferably substituted with MO— in the side chain attachment stage, thus compound (19) corresponds to Formula ($19_M$). In Stage 3a, compound (110) can be selectively deprotected at C(10) using an alcohol (e.g., $R_{10A}OH$ wherein $R_{10A}$ is alkyl) or a mixture of alcohols in the presence of a base to form 7-protected derivative (111). The reagents and conditions for selective deprotection are the same as described in connection with Stage 3a in Reaction Scheme 2. The C(10) deprotection is followed by acylation at C(10) to form 10-acyl-7-protected derivative (121) (i.e., $R_{10}$ is acyl). By way of an alternative pathway, compound (110) may be deprotected to yield a final product or derivatized further and then deprotected to yield a final product without selectively deprotecting C(10), as generally described in Reaction Schemes 1 and 1A and as illustrated in Stage 3c of Reaction Scheme 2A.

In Stage 2b of Reaction Scheme 2A, compound (19) is selectively deprotected at C(10) to form 7-protected derivative (112) prior to the attachment of the side chain at C(13). The reagents and conditions for selective deprotection are the same as described in connection with Stage 3a above. The C(10) deprotection is followed by C(10) acylation in Stage 3b to form 10-acyl-7-protected derivative (120) (i.e., $R_{10}$ is acyl). A side chain is then attached to the C(13) position of derivative (120) using a β-lactam (6) as described herein; alternatively, however, other side chain precursors such as an oxazinone, oxazoline, oxazoline carboxylic acid, oxazoline carboxylic acid anhydride, or isoserine derivative may be used instead. As described herein, the C(13) position of compound (120) is preferably substituted with MO— in the side chain attachment stage, thus compound (120) corresponds to Formula ($120_M$):

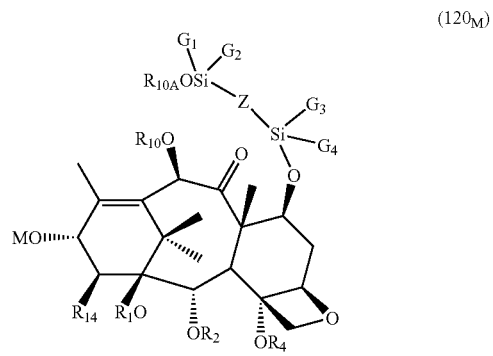

($120_M$)

wherein M is metal, ammonium, or hydrogen; $G_1$, $G_2$, $G_3$, $G_4$, and Z are as defined in connection with Formula (4); and $R_1$, $R_2$, $R_4$, and $R_{14}$ are as defined in connection with Formula (13).

In Stage 5 of Reaction Scheme 2A, derivative (121) (produced from either derivative (111) in Stage 4a or derivative (120) in Stage 4b) is deprotected to yield a final product or derivatized further and then deprotected to yield a final product. For example, the various protecting groups may be removed by hydrolysis under relatively mild conditions so as not to disturb the C(13) ester linkage and/or other hydrolyzable substituents on the polycyclic fused ring compound and/or the side chain.

Advantageously, using the bridging silicon-based protecting group to form the various intermediate compounds illustrated in Reaction Schemes 1, 1A, 2, and 2A, (e.g., Formulae (9), (19), (10), (110), (11), (111), (12), (112), (20), (120), (21), and (121)) various taxane compounds may be prepared. For example, depending on the nature of the substituents carried by the polycyclic fused ring polyol (e.g., Formulae (3) or (13)) and/or the side chain precursor (e.g., Formulae (5), (6), (7A), (7B), (7C), or (8)), and also depending on the derivatization of certain positions on the polycyclic fused ring polyol and/or the side chain, taxane compounds such as paclitaxel and docetaxel may be formed.

One preferred embodiment of the present invention is illustrated in Reaction Scheme 2B (which describes the production of paclitaxel) wherein $G_1$, $G_2$, $G_3$, $G_4$, $L_1$, $L_2$, and Z are as defined in connection with Formula (4) and $P_2$ is a hydroxy protecting group. For example, $P_2$ may be an acetal such as tetrahydropyranyl (THP), methoxymethyl (MOM), 1-ethoxyethyl (EE), 2-methoxy-2-propyl (MOP), 2,2,2-trichloroethoxymethyl, 2-methoxyethoxymethyl (MEM), 2-trimethylsilylethoxymethyl (SEM), and methylthiomethyl (MTM). Alternatively, $P_2$ may be a silyl protecting group having bulky alkyl groups such as trimethylsilyl, triethylsilyl, tributylsilyl, triisopropylsilyl, dimethylisopropylsilyl, diphenylmethylsilyl, dimethylphenylsilyl, and the like.

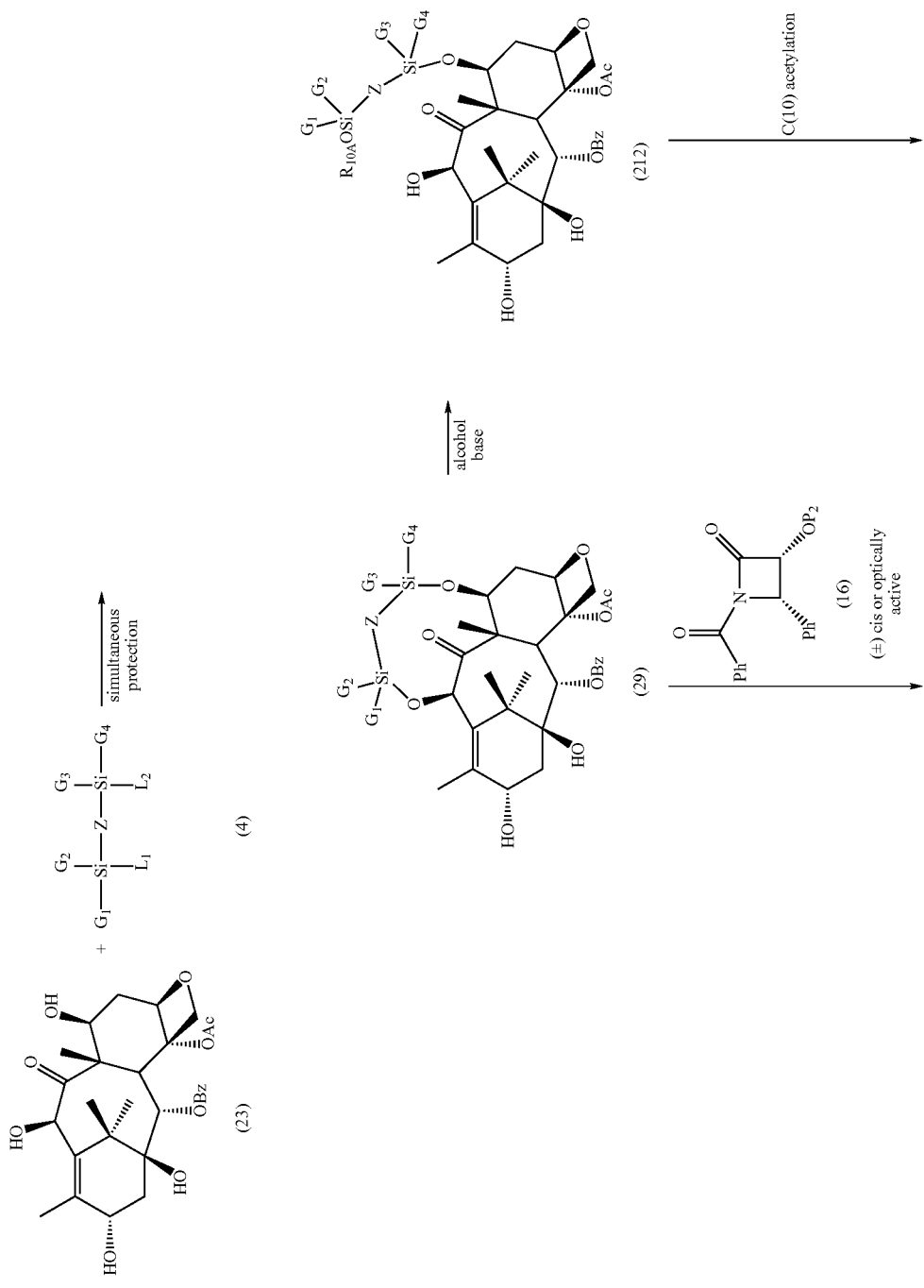

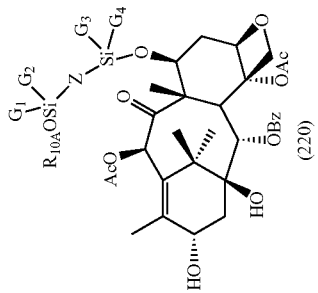 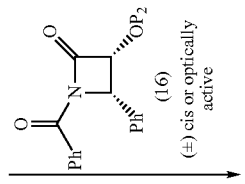 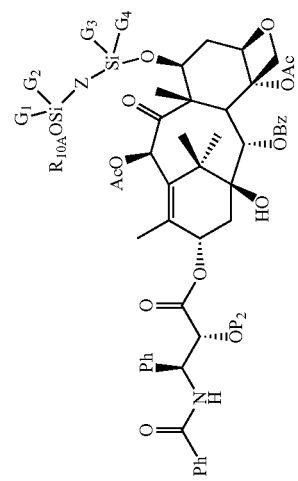
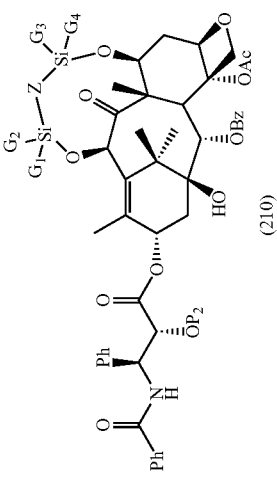 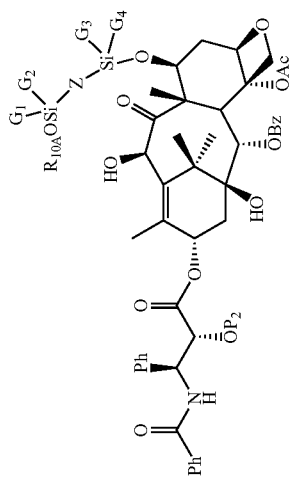 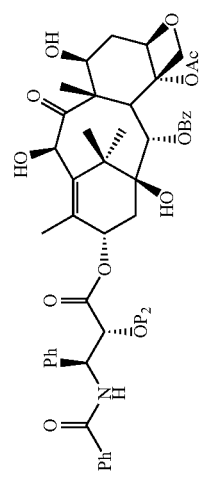

In Reaction Scheme 2B, 10-DAB (23) is first reacted with a bridging silicon-based protecting group (4) according to the processes described herein to yield 7,10-protected 10-DAB (29). Any bridging silicon-based protecting group described herein may be utilized in this stage, and the simultaneous protection is typically carried out in the presence of a base and a solvent. Appropriate bases and solvents that may be utilized in this stage are described in detail above. Following the protection of C(7) and C(10) with the bridging silicon-based protecting group (4), 7,10-protected 10-DAB (29) may be derivatized according to several synthetic pathways to form paclitaxel.

In one pathway, a side chain is attached to the C(13) position of 7,10-protected 10-DAB (29) using an appropriately substituted β-lactam (16) (i.e., N-benzoyl-4-phenyl-3-protected hydroxy-azetidin-2-one) as described herein; alternatively, however, other appropriately substituted side chain precursors such as an oxazinone, oxazoline, oxazoline carboxylic acid, oxazoline carboxylic acid anhydride, or isoserine derivative may be used instead. As described herein, the C(13) position of 7,10-protected 10-DAB (29) is preferably substituted with MO— in the side chain attachment stage, thus 7,10-protected 10-DAB (29) corresponds to Formula ($29_M$):

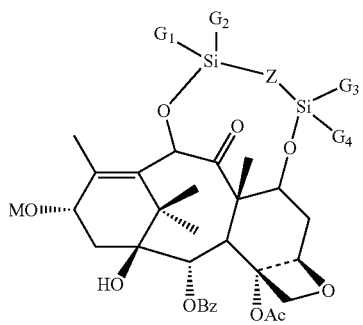

(29$_M$)

wherein M is metal, ammonium, or hydrogen; and $G_1$, $G_2$, $G_3$, $G_4$, and Z are as defined in connection with Formula (4).

After the attachment of the side chain to produce compound (210), compound (210) may be treated with an alcohol (e.g., $R_{10A}OH$ wherein $R_{10A}$ is alkyl) or a mixture of alcohols in the presence of a base to selectively open the bridging silicon-based protecting group at the C(10) position to form 7-protected derivative (211). The reagents and conditions for selective deprotection are the same as described in connection with Stage 3a in Reaction Scheme 2. The C(10) deprotection is followed by treatment with an acetylating agent (e.g., acetyl chloride) to acetylate the C(10) position, forming 10-acetoxy-7-protected derivative (221).

In an alternative pathway, derivative (221) can be produced by first treating 7,10-protected 10-DAB (29) with an alcohol or mixture of alcohols in the presence of a base to selectively open the bridging silicon-based protecting group at the C(10) position to form 7-protected derivative (212) using the same reagents and conditions as described in connection with other selective deprotection stages in this and other reaction schemes. Derivative (212) is acetylated at C(10) using an acetylating agent (e.g., acetyl chloride) to form 10-acetoxy-7-protected derivative (220). A side chain is then attached to derivative (220) using an appropriately substituted β-lactam (16) (i.e., N-benzoyl-4-phenyl-3-protected hydroxy-azetidin-2-one) as described herein; alternatively, however, other appropriately substituted side chain precursors such as an oxazinone, oxazoline, oxazoline carboxylic acid, oxazoline carboxylic acid anhydride, or isoserine derivative may be used instead. As described herein, the C(13) position of derivative (220) is preferably substituted with MO— in the side chain attachment stage, thus derivative (220) corresponds to Formula ($220_M$):

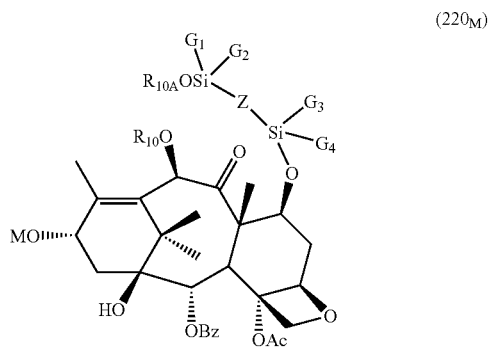

($220_M$)

Following the formation of derivative (221) according to either of these two pathways (i.e., (29)→(210)→(211)→(221) or (29)→(212)→(220)→(221)), derivative (221) is treated with a hydrolyzing agent to deprotect the C(7) and C(2') hydroxy groups, thus forming paclitaxel.

In another pathway illustrated in Reaction Scheme 2B, paclitaxel is produced by treating derivative (210) with a base (e.g., sodium carbonate ($Na_2CO_3$)) to completely remove the bridging silicon-based protecting group and form derivative (222). According to this pathway, the C(2') hydroxy protecting group (e.g., $P_2$) is selected to stay attached to the C(2') oxygen under the conditions of the reaction with an acetylating agent. Derivative (222) can then be treated with the acetylating agent (e.g., acetic anhydride) in the presence of a Lewis acid (e.g., $CeCl_3$) to selectively acetylate the C(10) hydroxy group, followed by deprotection of the C(2') hydroxy protecting group (e.g., removal of $P_2$) by treatment with a hydrolyzing agent to form paclitaxel.

Another preferred embodiment of the present invention is illustrated in Reaction Scheme 2C (which describes the production of paclitaxel) wherein $G_1$, $G_2$, $G_3$, $G_4$, $L_1$, $L_2$, and Z are as defined in connection with Formula (4).

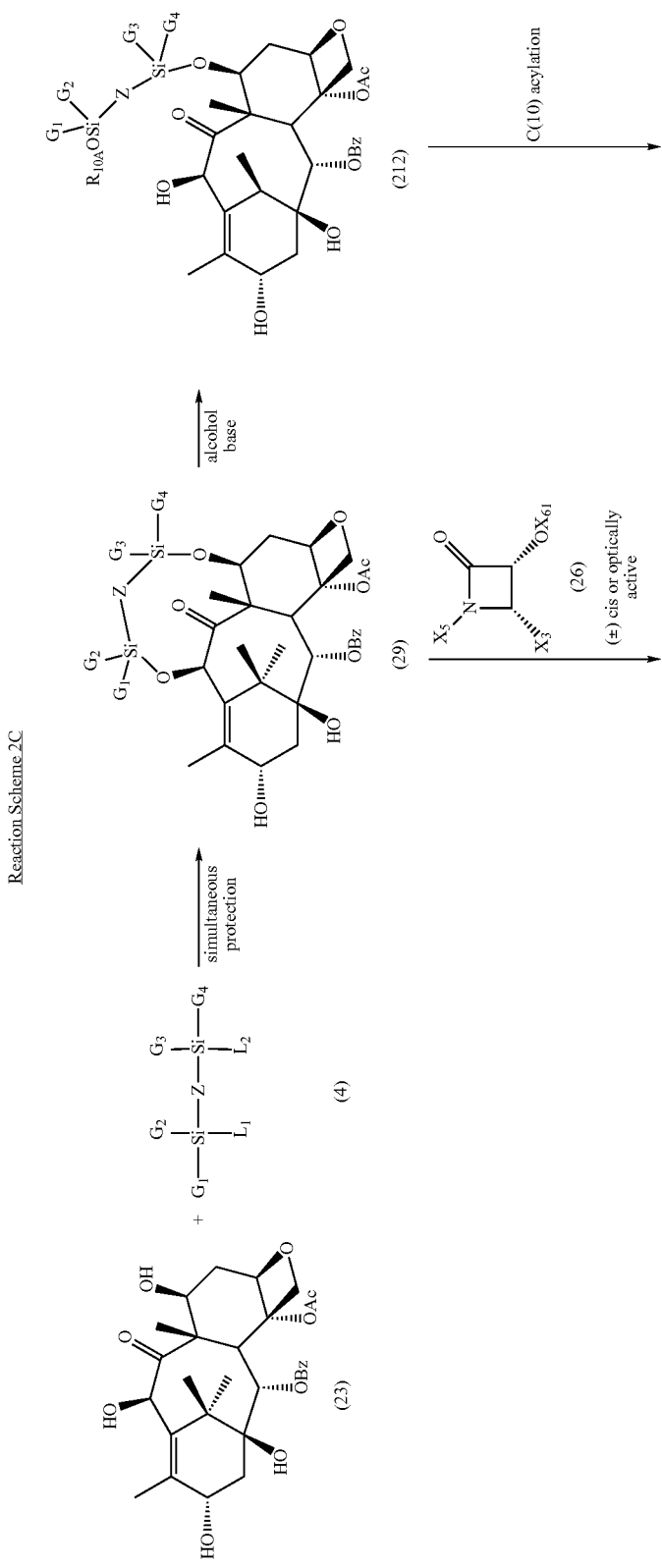

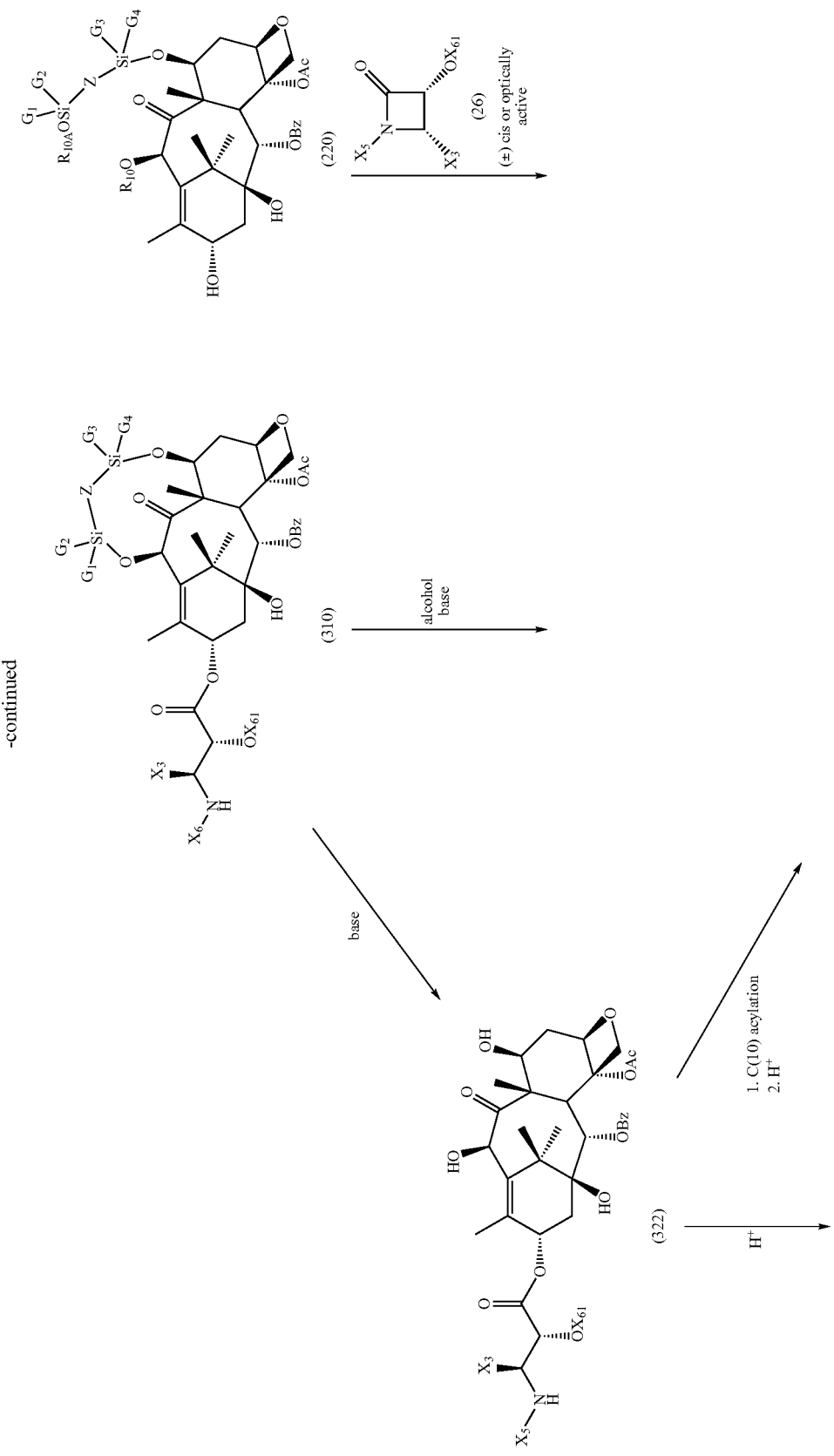

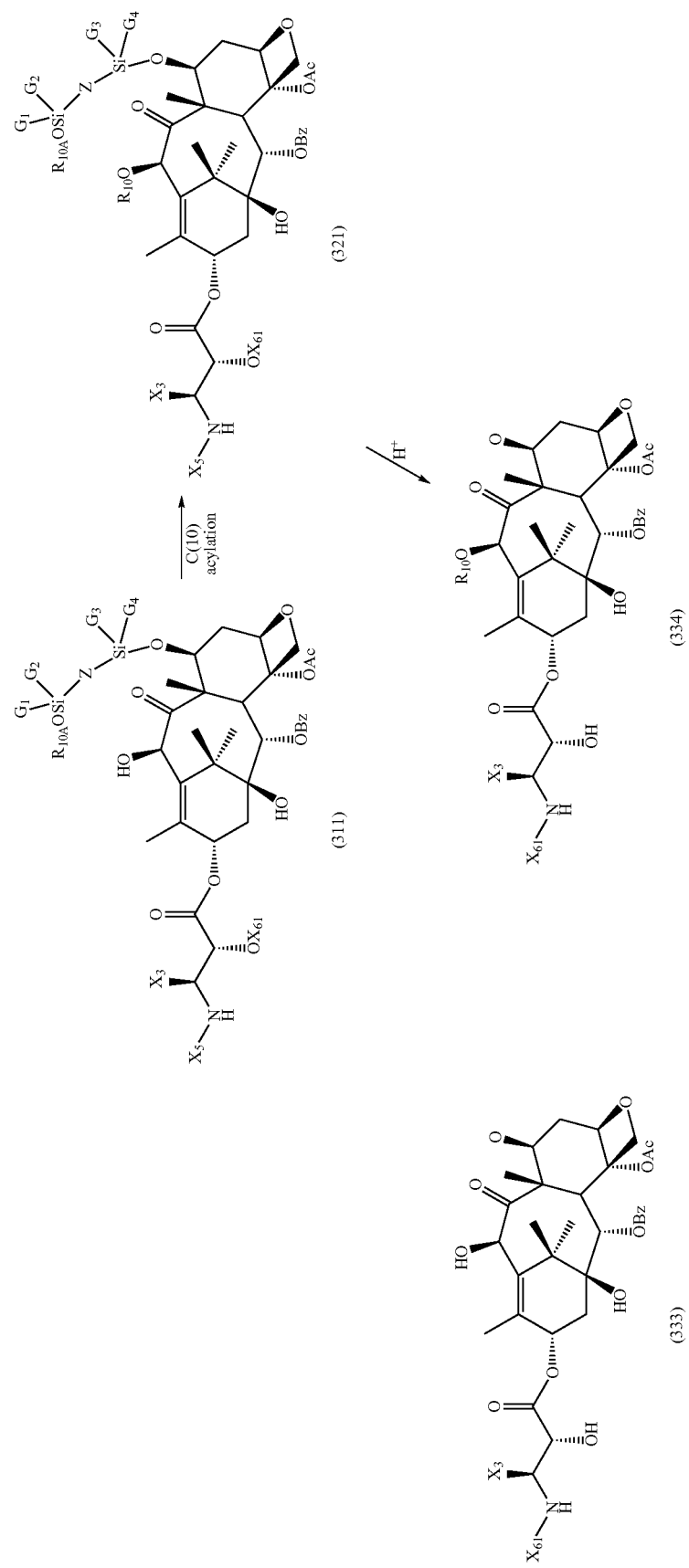

In Reaction Scheme 2C, 10-DAB (23) is first reacted with a bridging silicon-based protecting group (4) according to the processes described herein to yield 7,10-protected 10-DAB (29). Any bridging silicon-based protecting group described herein may be utilized in this stage, and the simultaneous protection is typically carried out in the presence of a base and a solvent. Appropriate bases and solvents that may be utilized in this stage are described in detail above. Then, in one pathway, a side chain is attached to the C(13) position of 7,10-protected 10-DAB (29) as described herein using β-lactam side chain precursor (26), wherein $X_3$ and $X_5$ are defined as above and $X_{61}$, is acyl. In one preferred embodiment, $X_6$, is tert-butoxycarbonyl or benzoyl. Alternatively, other similarly substituted side chain precursors such as an oxazinone, oxazoline, oxazoline carboxylic acid, oxazoline carboxylic acid anhydride, or isoserine derivative may be used instead. As described herein, the C(13) position of 7,10-protected 10-DAB (29) is preferably substituted with MO— in the side chain attachment stage, thus compound (29) corresponds to Formula ($29_M$).

After the attachment of the side chain to produce compound (310), compound (310) may be treated with an alcohol (e.g., $R_{10A}OH$ wherein $R_{10A}$ is alkyl) or a mixture of alcohols in the presence of a base to selectively open the bridging silicon-based protecting group at the C(10) position to form 7-protected derivative (311). The reagents and conditions for selective deprotection are the same as described in connection with Stage 3a in Reaction Scheme 2. The C(10) deprotection is followed by treatment with an acylating agent (e.g., acetyl chloride) to acylate the C(10) position, forming 10-acyloxy-7-protected derivative (321) (i.e., $R_{10}$ is acyl).

In an alternative pathway, derivative (321) can be produced by first treating 7,10-protected 10-DAB (29) with an alcohol or mixture of alcohols in the presence of a base to selectively open the bridging silicon-based protecting group at the C(10) position to form 7-protected derivative (212) using the same reagents and conditions as described in connection with other selective deprotection stages in this and other reaction schemes. Derivative (212) is acylated at C(10) using an acylating agent (e.g., acetyl chloride) to form 10-acyloxy-7-protected derivative (220). A side chain is then attached to derivative (220) as described herein using β-lactam side chain precursor (26), wherein $X_3$ and $X_5$ are defined as above and $X_{61}$, is acyl. In one preferred embodiment, $X_{61}$ is tert-butoxycarbonyl or benzoyl. Alternatively, other appropriately substituted side chain precursors such as an oxazinone, oxazoline, oxazoline carboxylic acid, oxazoline carboxylic acid anhydride, or isoserine derivative may be used instead. As described herein, the C(13) position of derivative (220) is preferably substituted with MO— in the side chain attachment stage, thus derivative (220) corresponds to Formula ($220_M$).

Following the formation of derivative (321) according to either of these two pathways (i.e., (29)→(310)→(311)→(321) or (29)→(212)→(220)→(321)), derivative (321) is selectively deprotected at $X_5$ and at the C(7) hydroxy group; that is, the $X_5$ group and the bridging silicon-based protecting group still attached to the C(7) hydroxy position are removed under conditions wherein $X_{61}$ is not removed. Once the $X_5$ group is removed from the 3' nitrogen position, the $X_{61}$, acyl group attached to the C(2') oxygen migrates to the 3' nitrogen, thus forming derivative (334). Depending on the substituents carried by the side chain and the acylating agent used to acylate the C(10) position, a variety of 10-DAB derivatives may be formed. For example, when $X_3$ is phenyl, $X_5$ is a protecting group that can be removed under conditions wherein $X_{61}$ is not removed, $X_{61}$ is benzoyl, and $R_{10}$ is acetyl, and the benzoyl group (i.e., $X_{61}$) attached to the C(2') oxygen migrates to the 3' nitrogen position, paclitaxel is formed.

In another pathway illustrated in Reaction Scheme 2C, derivative (310) can be treated with a base (e.g., sodium carbonate ($Na_2CO_3$)) to completely remove the bridging silicon-based protecting group and form derivative (322). Derivative (322) can then be treated with an acylating agent (e.g., acetic anhydride) in the presence of a Lewis acid (e.g., $CeCl_3$) to selectively acylate the C(10) hydroxy group. The $X_5$ group can then be selectively removed from the 3' nitrogen position under conditions wherein $X_{61}$ is not removed. Once the $X_5$ group is removed from the 3' nitrogen position, the $X_{61}$ acyl group attached to the C(2') oxygen migrates to the 3' nitrogen position, thus forming derivative (334). As noted above, depending on the substituents carried by the side chain precursor and the acylating agent used to acylate the C(10) position, a variety of 10-DAB derivatives may be formed. For example, when $X_3$ is phenyl, $X_5$ is a protecting group that can be removed under conditions wherein $X_{61}$ is not removed, $X_{61}$ is benzoyl, and $R_{10}$ is acetyl, and the benzoyl group attached to the C(2') oxygen migrates to the 3' nitrogen position, paclitaxel is formed.

Alternatively, the $X_5$ group of derivative (322) may be selectively removed without selectively acylating the C(10) hydroxy group. Once the $X_5$ group is removed as described above, the $X_{61}$ acyl group attached to the C(2') oxygen migrates to the 3' nitrogen position, forming derivative (333). Depending on the substituents carried by the side chain, a variety of 10-hydroxy derivatives may be formed. For example, when $X_3$ is phenyl, $X_5$ is a protecting group that can be removed under conditions wherein $X_{61}$ is not removed, and $X_{61}$ is tert-butoxycarbonyl, the tert-butoxycarbonyl group attached to the C(2') oxygen can migrate to the 3' nitrogen position to form docetaxel.

Another preferred embodiment of the present invention is illustrated in Reaction Scheme 2D (which describes the production of docetaxel) wherein $G_1$, $G_2$, $G_3$, $G_4$, $L_1$, $L_2$, and Z are as defined in connection with Formula (4) and $P_2$ is a hydroxy protecting group as described herein.

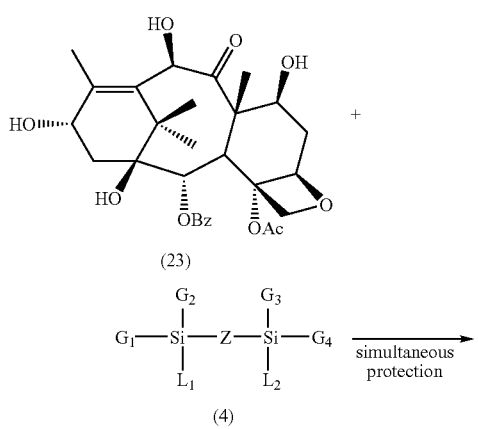

Reaction Scheme 2D

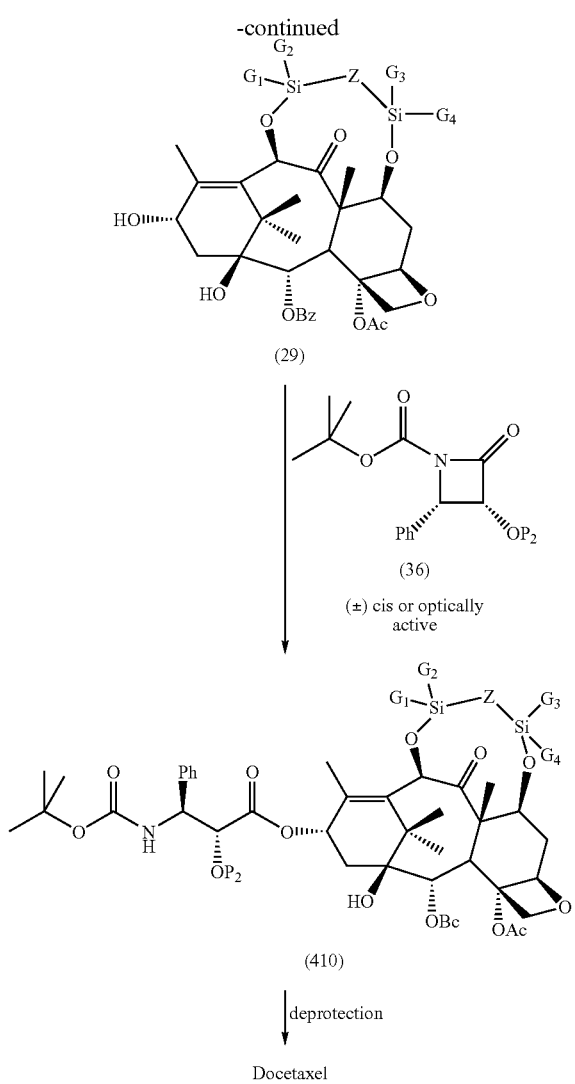

(29)

(36)

(±) cis or optically active (410)

deprotection

Docetaxel

In Reaction Scheme 2D, 10-DAB (23) is first reacted with a bridging silicon-based protecting group (4) according to the processes described herein to yield 7,10-protected 10-DAB (29). Any bridging silicon-based protecting group described herein may be utilized in this stage, and the simultaneous protection is typically carried out in the presence of a base and a solvent. Appropriate bases and solvents that may be utilized in this stage are described in detail above. Then, a side chain is attached to the C(13) position of 7,10-protected 10-DAB (29) using an appropriately substituted β-lactam (36) (i.e., N-t-butoxycarbonyl-4-phenyl-3-protected hydroxy-azetidin-2-one) as described herein; alternatively, however, other appropriately substituted side chain precursors such as an oxazinone, oxazoline, oxazoline carboxylic acid, oxazoline carboxylic acid anhydride, or isoserine derivative may be used instead. As described herein, the C(13) position of 7,10-protected 10-DAB (29) is preferably substituted with MO— in the side chain attachment stage, thus compound (29) corresponds to Formula ($29_M$).

After the attachment of the side chain to produce compound (410), compound (410) is deprotected according to the processes described herein to form docetaxel. For example, the C(7), C(10), and C(2') protecting groups may be completely removed by a hydrolyzing agent such as (hydrofluoric acid (HF) or hydrochloric acid (HCl) without disturbing the C(13), C(2), or C(4) ester linkages. Alternatively, the C(10) position may be selectively deprotected using an alcohol or a mixture of alcohols in the presence of a base as described herein, followed by the removal of the remaining protecting groups using a hydrolyzing agent to form docetaxel.

As described in Reaction Schemes 1, 1A, 2, and 2A, the treatment of polycyclic fused ring compound (3) or (13) with the bridging silicon-based protecting group (4) produces the intermediate compounds (9) and (19), which are useful in the production of various products and intermediates. Similarly, in Reaction Schemes 2A, 2B, 2C, and 2D, the treatment of 10-DAB (23) with the bridging silicon-based protecting group (4) produces the common intermediate 7,10-protected 10-DAB (29), which is useful in the production of taxane compounds such as paclitaxel and docetaxel.

Compound (410), produced in Reaction Scheme 2D and utilized in the production of docetaxel may also be utilized as a common intermediate in the production of paclitaxel as well; that is, the present invention enables the production of common intermediates useful in the production of both paclitaxel and docetaxel by simultaneously protecting 10-DAB with a bridging silicon-based protecting group to produce a first intermediate compound (7,10-protected 10-DAB (29)), attaching an appropriately substituted side chain to produce a second intermediate compound (compound (410)), and subjecting the second intermediate compound to various deprotection, selective deprotection, and/or derivatization reactions to form docetaxel or paclitaxel. This strategy is illustrated in Reaction Scheme 2E wherein $G_1$, $G_2$, $G_3$, $G_4$, $L_1$, $L_2$, and Z are as defined in connection with Formula (4) and $P_2$ is a hydroxy protecting group as defined herein.

Reaction Scheme 2E

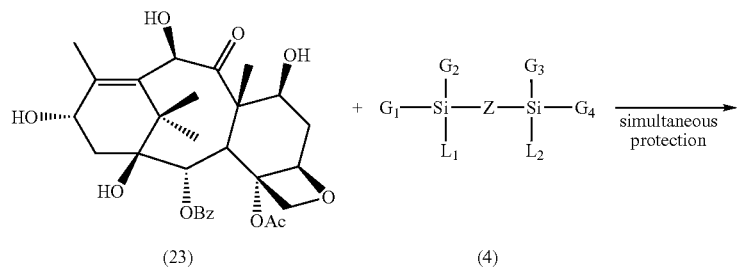

simultaneous protection

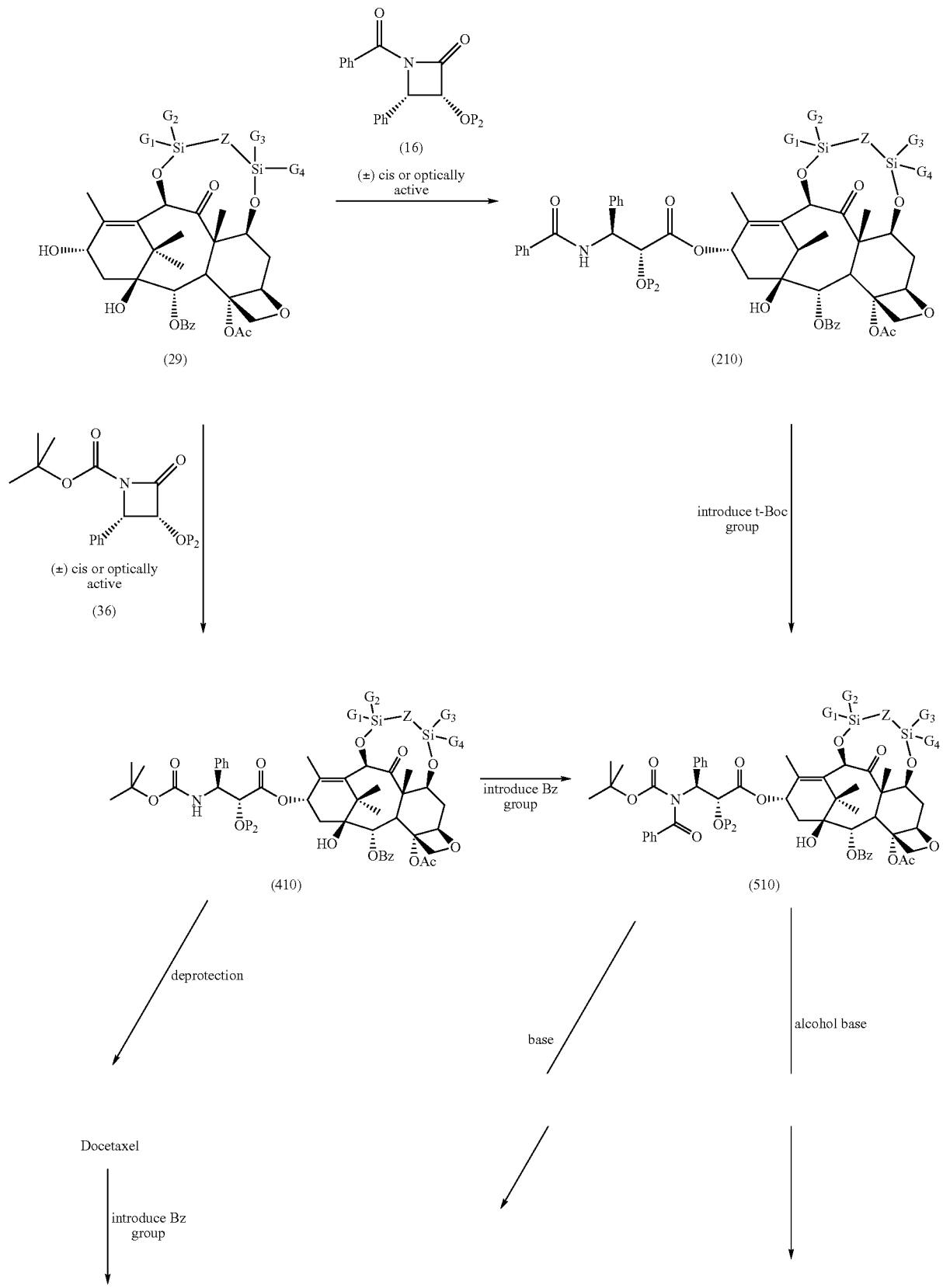

-continued

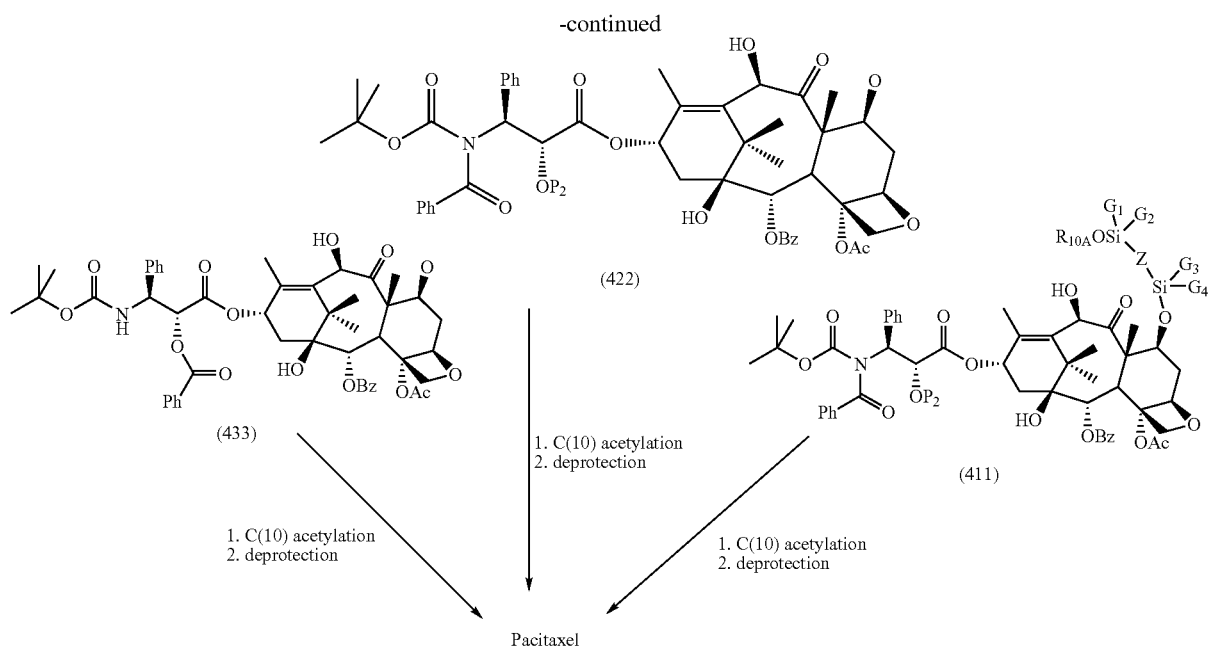

Pacitaxel

As illustrated in Reaction Scheme 2E, the common intermediate 7,10-protected 10-DAB (29) is produced by reacting 10-DAB (23) with a bridging silicon-based protecting group (4) according to the processes described herein. Any bridging silicon-based protecting group described herein may be utilized in this stage, and the simultaneous protection is typically carried out in the presence of a base and a solvent. Appropriate bases and solvents that may be utilized in this stage are described in detail above. Then, the second common intermediate in the production of both paclitaxel and docetaxel is produced by attaching a side chain to the C(13) position of 7,10-protected 10-DAB (29) using an appropriately substituted β-lactam (36) (i.e., N-t-butoxycarbonyl-4-phenyl-3-protected hydroxy-azetidin-2-one) as described herein; alternatively, however, other side chain precursors such as an oxazinone, oxazoline, oxazoline carboxylic acid, oxazoline carboxylic acid anhydride, or isoserine derivative may be used instead. As described herein, the C(13) position of 7,10-protected 10-DAB (29) is preferably substituted with MO— in the side chain attachment stage, thus 7,10-protected 10-DAB (29) corresponds to Formula ($29_M$).

After the attachment of the side chain to produce the common intermediate compound (410), compound (410) may be deprotected according to the process described in Reaction Scheme 2D to produce docetaxel; that is, the C(7), C(10), and C(2') protecting groups may be completely removed by a hydrolyzing agent such as hydrofluoric acid (HF) or hydrochloric acid (HCl) without disturbing the C(13), C(2), or C(4) ester linkages. Alternatively, the C(10) position may be selectively deprotected using an alcohol or a mixture of alcohols in the presence of a base as described herein, followed by the removal of the remaining protecting groups using a hydrolyzing agent to form docetaxel.

To form paclitaxel from compound (410), a benzoyl group is introduced to the 3' nitrogen of the side chain of compound (410), forming derivative (510). In various embodiments, the benzoyl group can be added during the workup of the side chain attachment stage due to the negative charge on the nitrogen during the workup at that point in the synthesis. Derivative (510) can then be transformed to paclitaxel through either of the two pathways described above in Reaction Schemes 2B, 2C, and 2D. For example, in one pathway, derivative (510) is treated with an alcohol or mixture of alcohols in the presence of a base to selectively open the bridging silicon-based protecting group at the C(10) position and form 7-protected derivative (411). The C(10) deprotection is followed by treatment with an acetylating agent (e.g., acetyl chloride) and a hydrolyzing agent to remove the various protecting groups (including the tert-butoxycarbonyl group on the 3' nitrogen) to form paclitaxel.

In a second pathway, derivative (510) is treated with a base (e.g., sodium carbonate ($Na_2CO_3$)) to completely remove the bridging silicon-based protecting group producing derivative (422), followed by selectively acetylating the C(10) position with an acetylating agent (e.g., acetic anhydride) in the presence of a Lewis acid (e.g., $CeCl_3$) and deprotection of the various protecting groups (including the tert-butoxycarbonyl group on the 3' nitrogen) with a hydrolyzing agent to form paclitaxel.

In an alternative pathway for forming paclitaxel without forming compound (410), intermediate compound (510) may be formed by attaching a side chain to the C(13) position of 7,10-protected 10-DAB (29) using an appropriately substituted β-lactam (16) (i.e., N-benzoyl-4-phenyl-3-protected hydroxy-azetidin-2-one) as described herein; alternatively, however, other side chain precursors such as an oxazinone, oxazoline, oxazoline carboxylic acid, oxazoline carboxylic acid anhydride, or isoserine derivative may be used instead. As described herein, the C(13) position of 7,10-protected 10-DAB (29) is preferably substituted with MO— in the side chain attachment stage, thus 7,10-protected 10-DAB (29) corresponds to Formula (29$_M$).

After the attachment of the side chain to produce intermediate compound (210), a tert-butoxycarbonyl group is introduced to the 3' nitrogen on the side chain, by reacting compound (210), e.g., with di-tert-butyldicarbonate (i.e., Boc$_2$O) in the presence of a polar aprotic solvent (e.g., ethyl acetate, tetrahydrofuran (THF), or dimethylformamide (DMF)), forming derivative (510). Derivative (510) can then be transformed to paclitaxel through either of the two pathways described above.

In another alternative pathway, paclitaxel may be produced from docetaxel (formed as described above). After the deprotection of compound (410) to form docetaxel, a benzoyl group may be selectively introduced to the C(2') hydroxy position of docetaxel using benzoyl chloride (or other benzoyl halide) in the presence of a amine (e.g., pyridine) to form derivative (433). The C(10) position of derivative (433) may then be selectively acetylated with an acetylating agent (e.g., acetic anhydride) in the presence of a Lewis acid (e.g., CeCl$_3$), followed by deprotection of the 3' nitrogen tert-butoxycarbonyl group with a hydrolyzing agent. Once the 2' tert-butoxycarbonyl group is removed, the benzoyl group attached to the C(2') oxygen migrates to the 3' nitrogen, thus forming paclitaxel.

Reaction Scheme 3 illustrates the derivatization of various positions on a 7,10-protected polycyclic fused ring compound wherein G$_1$, G$_2$, G$_3$, G$_4$, L$_1$, L$_2$, and Z are as defined in connection with Formula (4) and P$_{13}$ is a hydroxy protecting group as described herein. By way of example, it may be desirable to derivatize the C(1), C(2), and/or the C(4) positions on the polycyclic fused ring compound prior to the attachment of a side chain at the C(13) position. The C(2) and/or C(4) esters of polycyclic fused ring derivatives can be reduced to the corresponding alcohol(s) using reducing agents such as lithium aluminum hydride (LAH) or Red-Al, and new esters can be thereafter substituted using standard acylating agents such as anhydrides and acid chlorides in combination with an amine such as, for example, pyridine, triethylamine, N,N-4-dimethylaminopyridine (DMAP), or diisopropyl ethyl amine. Alternatively, the C(2) and/or C(4) alcohols may be converted to new C(2) and/or C(4) esters through formation of the corresponding alkoxide by treatment of the alcohol(s) with a suitable base such as LDA followed by an acylating agent such as an acid chloride. To simplify the description in Reaction Scheme 3, 10-DAB (23) is utilized as the starting material. It should be understood, however, that other polycyclic fused ring polyols may be utilized as the starting material.

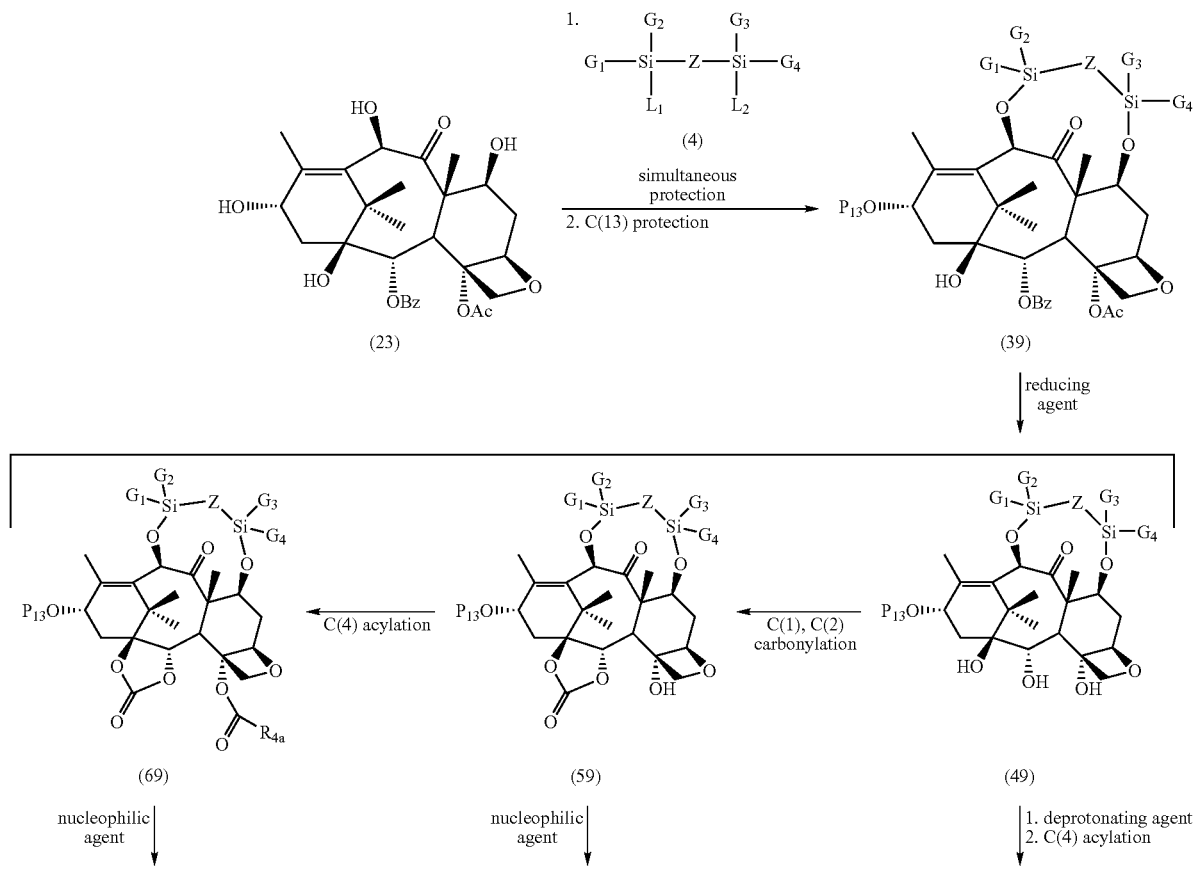

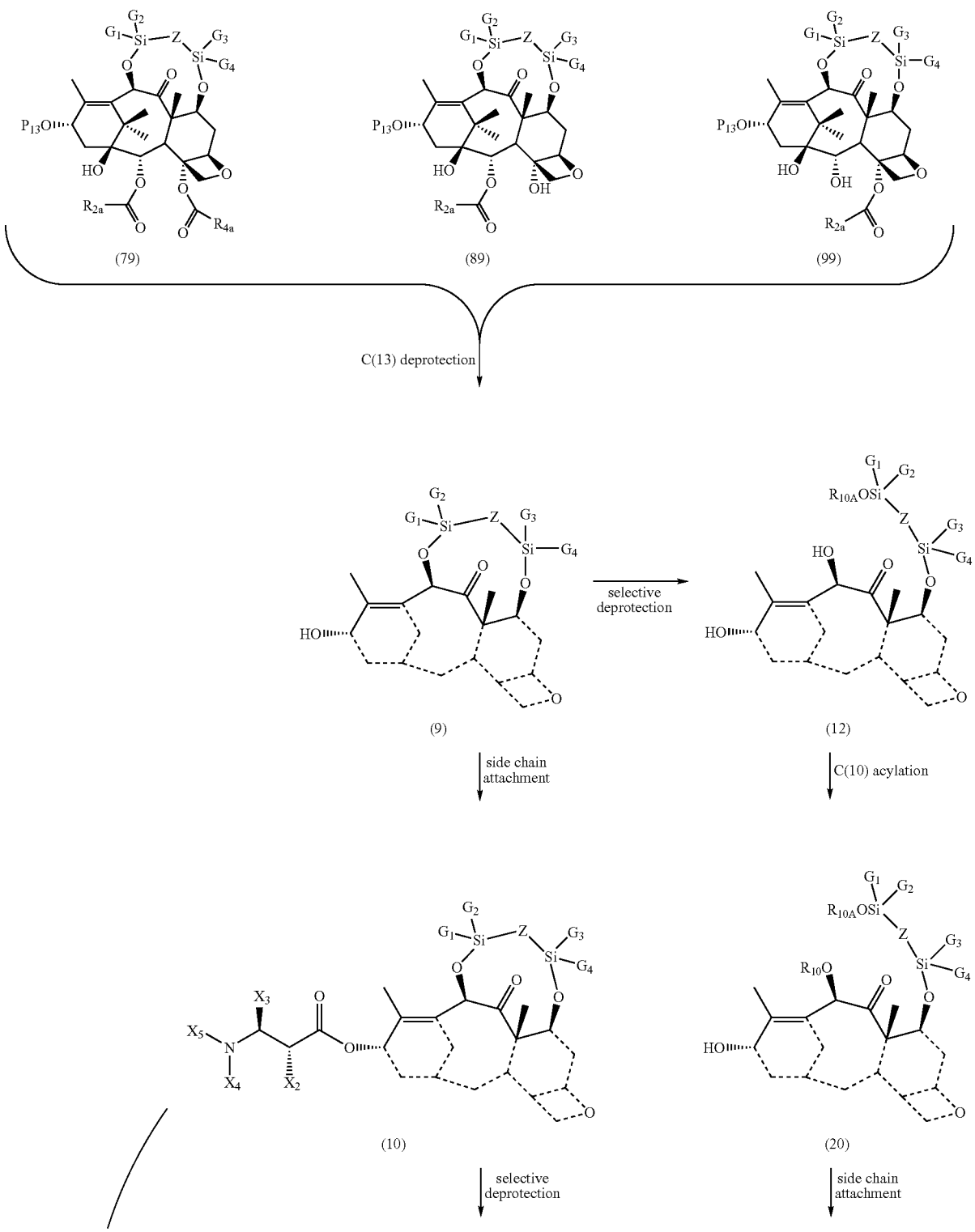

-continued

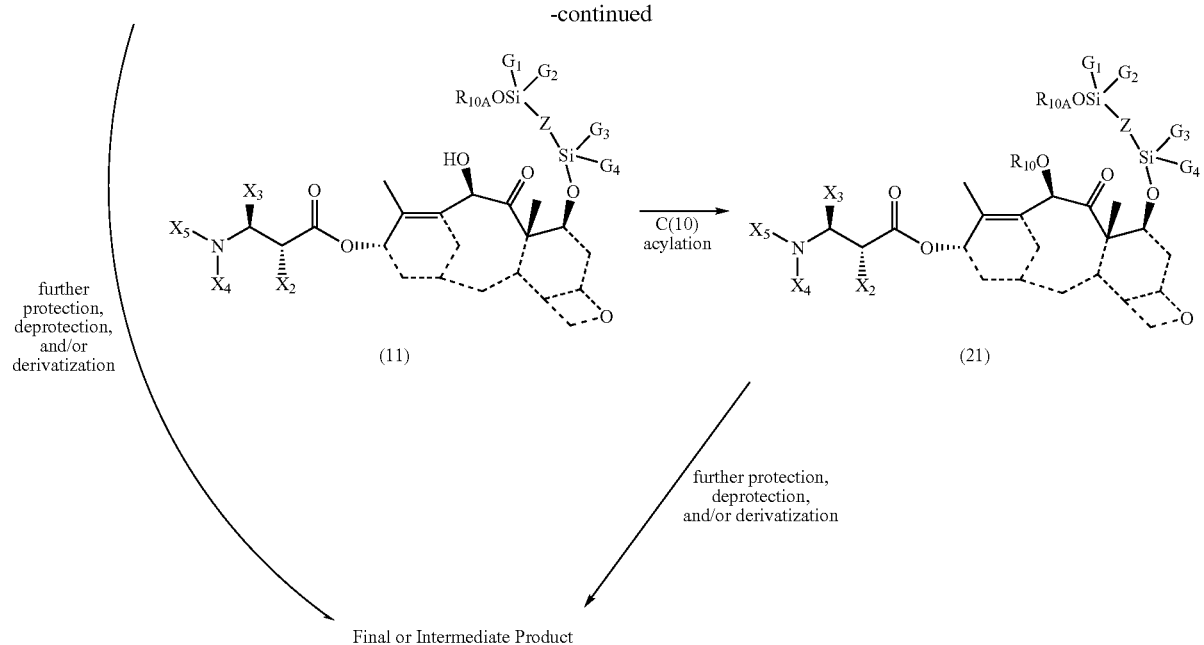

Final or Intermediate Product

As illustrated in Reaction Scheme 3, after the simultaneous protection of the C(7) and C(10) hydroxy groups of 10-DAB (23) with the bridging silicon-based protecting group (4) and after the protection of the C(13) hydroxy group with a suitable protecting group (e.g., trimethylsilyl chloride (TMSCl) in the presence of an amine base such as triethylamine), 7,10,13-protected compound (39) is converted to the triol (49) with a reducing agent (e.g., lithium aluminum hydride (LAH)). Triol (49) is then converted to the 1,2-carbonate derivative (59) using a carbonylating agent such as an acid halide (e.g., $Cl_2CO$) in pyridine). 1,2-carbonate derivative (59) may then be acylated at C(4) under vigorous standard conditions to produce 1,2-carbonate-4-acyl derivative (69). Derivatives (59) and/or (69) may each be treated with a nucleophilic agent such as Grignard reagents (e.g., $R_{2a}MgBr$) or alkyllithium reagents (e.g., $R_{2a}Li$) to form the C(2) esters (79) and/or (89). Alternatively, triol (49) may be deprotonated with a deprotonating agent (e.g., lithium diisopropylamide (LDA)) followed by the introduction of an acylating agent to selectively give the C(4) ester (99).

The brackets surrounding derivatives (49), (59), (69), (79), (89), and (99) indicate that, after their respective formation, each of these derivatives may be deprotected at C(13) using a hydrolyzing agent that will not disturb the C(7) and C(10) bridging silicon-based protecting group (e.g., hydrofluoric acid (HF) in pyridine without proceeding to the next synthetic stage. Upon deprotection at C(13), the derivatized compound may undergo any of the various synthetic routes described in Reaction Schemes 1, 1A, 2, and 2A. In other words, the dashed lines in the starting material of Reaction Schemes 1 and 2 (i.e., polycyclic fused ring polyol (3)) denote the skeletal structure of the polycyclic fused ring compound irrespective of the substituents carried at the positions represented by the dashed lines, substituents which may, for example, correspond to those carried by Formulae (49), (59), (69), (79), (89), and (99). Similarly, the substituents carried at the positions represented as $R_1$, $R_2$, R4, and $R_{14}$ in the starting material of Reaction Schemes 1A and 2A (i.e., polycyclic fused ring polyol (13)) may correspond to the substituents carried by, for example, Formulae (49), (59), (69), (79), (89), and (99). Further, and as illustrated in Reaction Schemes 2B, 2C, 2D, and 2E, the dashed lines may correspond to the substituents carried by 10-DAB.

Abbreviations And Definitions

The following definitions and methods are provided to better define the present invention and to guide those of ordinary skill in the art in the practice of the present invention. Unless otherwise noted, terms are to be understood according to conventional usage by those of ordinary skill in the relevant art.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters, ethers, and thioethers.

The term "heteroatom" shall mean atoms other than carbon and hydrogen.

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halide," "halogen" or "halo" as used herein alone or as part of another group refer to chlorine, bromine, fluorine, and iodine.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "acyl," as used herein alone or as part of another group, denotes the moiety formed by removal of the hydroxy group from the group —COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "acyloxy," as used herein alone or as part of another group, denotes an acyl group as described above bonded through an oxygen linkage (—O—), e.g., RC(O)O— wherein R is as defined in connection with the term "acyl."

Unless otherwise indicated, the alkoxycarbonyloxy moieties described herein comprise lower hydrocarbon or substituted hydrocarbon or substituted hydrocarbon moieties.

Unless otherwise indicated, the carbamoyloxy moieties described herein are derivatives of carbamic acid in which one or both of the amine hydrogens is optionally replaced by a hydrocarbyl, substituted hydrocarbyl or heterocyclo moiety.

The terms "hydroxy protecting group" as used herein denote a group capable of protecting a free hydroxy group ("protected hydroxy") which, subsequent to the reaction for which protection is employed, may be removed without disturbing the remainder of the molecule. Exemplary hydroxy protecting groups include ethers (e.g., allyl, triphenylmethyl (trityl or Tr), benzyl, p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of protecting groups for the hydroxy group and the synthesis thereof may be found in "Protective Groups in Organic Synthesis" by T. W. Greene and P. G. M. Wuts, John Wiley & Sons, 1999.

The terms "amino protecting group" as used herein denote moieties that block reaction at the protected amino group while being easily removed under conditions that are sufficiently mild so as not to disturb other substituents of the various compounds. Exemplary amino protecting groups include benzyl, benzoyl, carbobenzyloxy (Cbz), t-butoxycarbonyl (t-Boc), allyloxycarbonyl and the like. A variety of protecting groups for the amino group and the synthesis thereof may be found in "Protective Groups in Organic Synthesis" by T. W. Greene and P. G. M. Wuts, John Wiley & Sons, 1999.

The terms "sulfhydryl protecting group" as used herein are moieties that block reaction at the protected sulfhydryl group while being easily removed under conditions that are sufficiently mild so as not to disturb other substituents of the various compounds. For example, the sulfhydryl protecting groups may be silyl esters, disulfides and the like. A variety of protecting groups for the sulfhydryl group and the synthesis thereof may be found in "Protective Groups in Organic Synthesis" by T. W. Greene and P. G. M. Wuts, John Wiley & Sons, 1999.

As used herein, "Ac" means acetyl (i.e., $CH_3C(O)$—); "Bz" means benzoyl (i.e., $C_6H_5C(O)$—); "Ph" means phenyl; "TMSCl" means trimethylsilyl chloride; "LAH" means lithium aluminum hydride; "LDA" means lithium diisopropylamide; "10-DAB" means 10-desacetylbaccatin III; "—OP" means protected hydroxy, wherein P is a hydroxy protecting group; "t-Boc" and "Boc" mean tert-butoxycarbonyl; "DMF" means dimethylformamide; "THF" means tetrahydrofuran; "DMAP" means N,N-4-dimethylaminopyridine; "LHMDS" means lithium hexamethyldisilazide; "NaHMDS" means sodium hexamethyldisilazide; "TEA" means triethylamine; and "TsOH" means p-toluenesulfonic acid.

The term "taxane" as used herein, denotes compounds containing the A, B and C rings (with numbering of the ring positions shown herein):

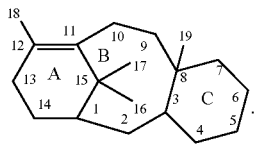
(IV)

The following examples illustrate the invention.

EXAMPLE 1

Preparation of Trimethylsilyl 2-(trimethylsilyloxy)acetate

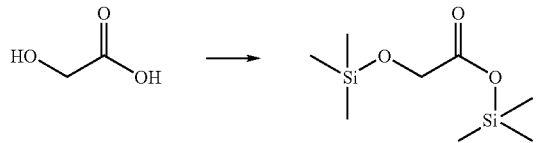

Trimethylsilyl 2-(trimethylsilyloxy)acetate is available from many vendors. However, it can be easily prepared from inexpensive glycolic acid ($75/Kg from Aldrich) and trimethylsilyl chloride ($80/Kg from Aldrich) in the presence of 2 equivalents of pyridine. Typically, glycolic acid (76.05 g, 1 mol) was dissolved in dry pyridine (164 mL, 2 mol) then the mixture was cooled to 0 to 5° C. in an ice-water bath with stirring. Neat trimethylsilyl chloride (108.64 g, 1 mol) was added drop-wise to control the exotherm to less than 40° C. Pyridinium chloride precipitated as a free flowing solid. Heptane (500 mL) was added to aid the agitation. The second equivalent of neat trimethylsilyl chloride was added and the mixture was stirred at ambient 22 to 40° C. for 30 minutes until the reaction was complete. The mixture was further diluted with heptane (1 L) and the salt was allowed to precipitate out. The heptane layer was siphoned into the rotary evaporator through a medium porous inline filter and concentrated to give a clear oil (215 g, 0.98 mol) of the trimethylsilyl 2-(trimethylsilyloxy)acetate. It was distilled in the rotary evaporator at 70 to 75° C. under vacuum of 6 to 8 mmHg.

EXAMPLE 1A

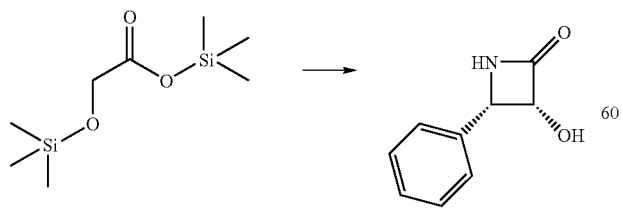

When the reaction of the lithium enolate (made by treating trimethylsilyl-(trimethylsilyloxy)acetate with lithium hex amethyldisilazide) with trimethylsilylbenzaldimine (generated in situ from aldehyde (1a-f below) and lithium hexamethyldisilazide) reported by Hart et al. (*Chem. Rev.* 1989, 89, 1447-1465) was examined, the enolate decomposition occurred faster than its reaction with the imine at 0 to 5° C. A solution to this problem was found by lowering the temperature of the enolate's reaction to −25° C. and using an excess (e.g., 2 eqs) amount of the enolate.

Thus, benzaldehyde (5.3 g, 0.05 mol) was added to the 1.0 M solution of LHMDS in THF (150 mL 0.15 mol) at 0° C. and the mixture was stirred for 30 minutes before cooling to −30 to −25° C. Once the reaction temperature was at −30° C., a 1 M solution of the trimethylsilyl 2-(trimethylsiloxy)acetate ester (22.0 g, 0.1 mol, 2 eq) in THF was added drop-wise to control the exotherm to maintain the reaction temperature to <−25° C. The mixture was stirred at this temperature for 1 h before warming to −5 to 0° C. The mixture was stirred at this temperature for 18 h. The mixture was quenched with a saturated solution of sodium bicarbonate (100 mL) and extracted with 1-butanol (500 mL). The 1-butanol was evaporated under vacuum and the residue was taken up in methanol (75 mL) and sodium carbonate (0.5 g, 0.005 mol) for approximately 1 h at ambient temperature. The reaction mixture then was quenched with acetic acid (0.6 g, 0.010 mol), triethylamine (2 g, 0.02 mol), and diluted with 100 mL of ethyl acetate. The mixture was filtered through a pad of silica gel (50 g) and the filtrate was concentrated on a rotary evaporator at 40° C. until crystal formation occurred. The mixture was cooled in a 0° C. ice bath for 30 min and the crystals were collected via vacuum filtration, washed with cold ethyl acetate, and dried to a constant weight of 4.13 g (50% yield); a white powder resulted.

EXAMPLE 2

Preparation of 3-hydroxy-4-substituted-azetidin-2-ones

A 1 M solution of LHMDS in THF (100 mL, 0.1 mol) was cooled to 0° C. and a 1 M solution of trimethylsilyl 2-(trimethylsilyloxy)acetate (22.0 g, 0.1 mol) in THF that was prepared as in Example 1 was added drop-wise to control the exotherm and maintain the temperature at 0° C. to 5° C. To this solution was added 1 equivalent of trimethylsilyl chloride followed by the addition of 1 equivalent of LHMDS and 1 equivalent of benzaldehyde with stirring at 0 to 15° C. over 14 h. The 3-trimethylsilyloxy β-lactam products were observed (via HNMR of reaction mixture) as a 5:1 cis:trans ratio in quantitative yield. This process is depicted in Scheme 4 below.

Scheme 4

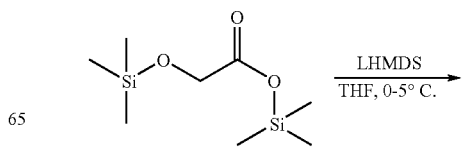

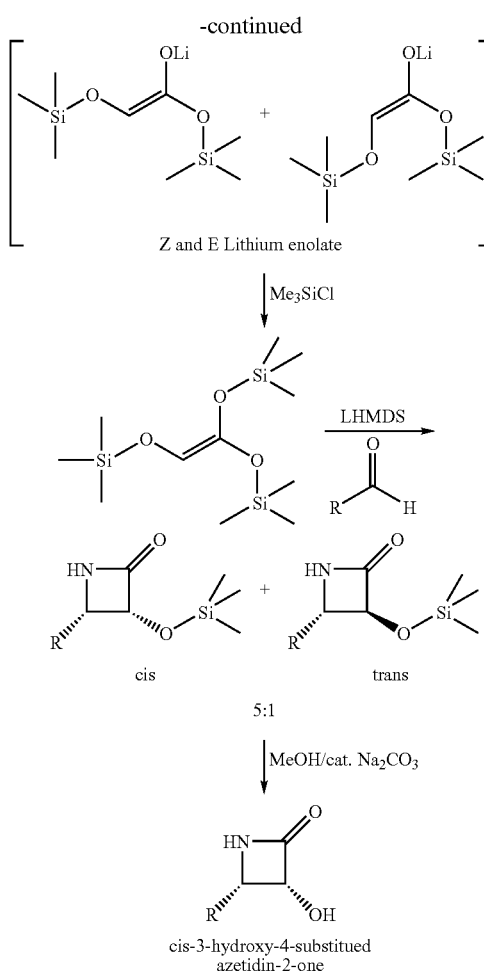

cis-3-hydroxy-4-substitued azetidin-2-one

Methanolysis of the silyl ether was easily accomplished in 15 minutes at ambient temperature with a catalytic amount of sodium carbonate and the desired product cis-hydroxy-4-substituted-β-lactam crystallized out in 48% isolated yield upon concentration from ethyl acetate.

EXAMPLE 3

Preparation of 3-hydroxy-4-thienyl-azetidin-2-one

Typically, a 1.0 M THF solution of lithium hexamethyldisilazide (140 mL, 0.14 mol) under nitrogen was diluted with THF (140 mL) and cooled to 0 to 5° C. with an ice-water bath. The trimethylsilyl 2-(trimethylsilyloxy)acetate (33.4 g, 0.14 mol) was added drop-wise over 20 minutes. To this enolate solution was added trimethylsilylchloride (17.7 mL, 0.14 mol) and after 5 minutes of stirring, a second portion of LHMDS solution in THF (100 mL, 0.10 mol) was added over 10 minutes. To this solution was added 2-thiophenecarboxaldehyde (11.2 g, 0.1 mol) drop-wise over 15 to 20 min to control the exotherm at <5° C. This solution was stirred at 0 to 5° C. over 14 h corresponding to complete disappearance of the imine.

The reaction was neutralized with glacial acetic acid (6 g, 0.10 mol) and diluted with ethyl acetate (400 mL) and transferred to a 2-L separatory funnel. The mixture was washed with water (100 mL) and brine (100 mL). The organic layer was dried over sodium sulfate, filtered through a pad of silica gel and concentrated to give a yellow solid. The solid was taken up in methanol (300 mL) and solid $Na_2CO_3$ (1.0 g) and the mixture was stirred at ambient temperature for 15 min. TLC monitoring eluting with 2:1 ethyl acetate:hexanes showed complete conversion from the non-polar TMS-ether (Rf=0.7) to the polar product (Rf=0.25). The reaction was quenched with glacial acetic acid (0.6 mL) and the mixture was concentrated to a solid. The solid was dissolved in hot ethyl acetate (500 mL) and the insoluble salts were filtered off through a pad of silica gel. The filtrate was concentrated under rotary evaporation at 40° C. to approximately 40 mL of volume to induce crystal formation. The mixture was cooled to ambient temperature and the crystals (8.13 g, 0.048 mol, 48% yield) were collected as a white powder. Furthermore, the process was conveniently carried out in a one-pot operation when the reaction was quenched with sodium bicarbonate and extracted with 1-butanol and ethyl acetate as described in Example 4.

EXAMPLE 4

Preparation of Various azetidin-2-ones

The ketene acetal tris(trimethylsilyloxy)ethene is a commercially available product, and can be used for the synthesis of β-lactams starting from various aldehydes as depicted in Scheme 7 below. Thus, when benzaldehyde was treated with a THF solution of lithium hexamethyldisilazide at 0° C., the N-trimethylsilylbenzaldimine was generated instantaneously along with an equivalent of lithium trimethylsilanolate. Stirring this mixture with the ketene acetal at 10 to 15° C. for 14 h resulted in the formation of the β-lactams similar to the reaction in Scheme 5. This ketene acetal reaction was found to be general across various aromatic and enolizable aliphatics we examined (see Table 2) and produced predominantly cis-β-lactams in all cases.

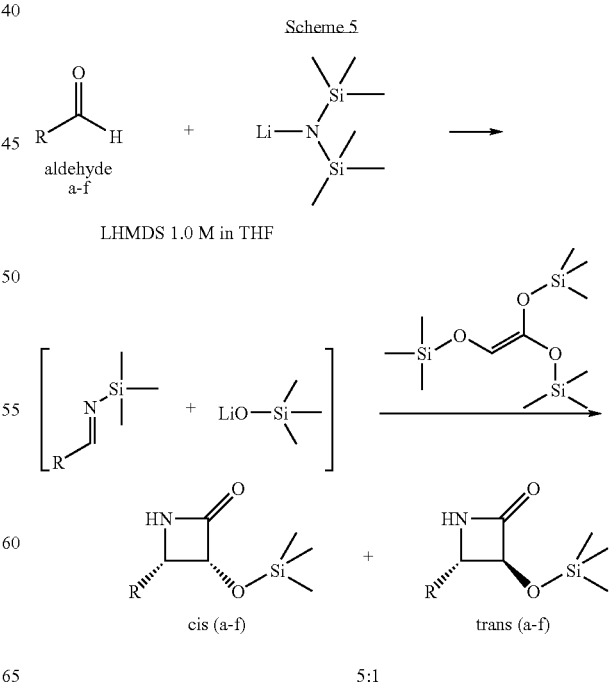

TABLE 2

| | Aldehyde | Cis:trans |
|---|---|---|
| a | benzaldehyde | 5:1 |
| b | cyclopropanecarboxaldehyde | 3:1 |
| c | furan-2-carboxaldehyde | 5:1 |
| d | thiophene-2-carboxaldehyde | 5:1 |
| e | pyridine-2-carboxaldehyde | 4:1 |
| f | cyclopentylacetaldehyde | 3:1 |

To optimize the reaction conditions, 0.8 equivalents of trimethylsilylchloride were added prior to the addition of the ketene acetal. This modification resulted in an increase in isolated yield to 66% of the product β-lactam a (Scheme 6). Thus, in a single operation starting with the readily available benzaldehyde and tris(trimethylsilyloxy)ethene we obtained β-lactam a in high purity which is an important intermediate for the synthesis of taxanes.

Scheme 6

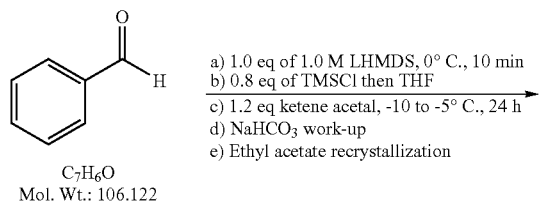

C₇H₆O
Mol. Wt.: 106.122 a) 1.0 eq of 1.0 M LHMDS, 0° C., 10 min
b) 0.8 eq of TMSCl then THF
c) 1.2 eq ketene acetal, -10 to -5° C., 24 h
d) NaHCO₃ work-up
e) Ethyl acetate recrystallization

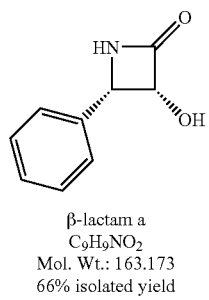

β-lactam a
C₉H₉NO₂
Mol. Wt.: 163.173
66% isolated yield

In one experiment, a 0.5 M solution of LHMDS in THF was cooled to −10 to 0° C. then 1.0 equivalent of benzaldehyde was added over 15 min to control the exothermic imine reaction temperature to <15° C. Once the reaction temperature was −10 to −5° C., neat tris(trimethylsilyl)ethene (1.2 eq) was added. The mixture was stirred at this temperature over 14 h. Reaction completion was monitored by HNMR for the disappearance of the imine. Once complete, trimethylsilyl chloride (1 eq) was added to convert the lithium trimethylsilanolate to the volatile hexamethyldisiloxane. The reaction was washed twice with water at 1/10 the volume of reaction mixture to remove the lithium chloride salt. To the THF solution was added a catalytic amount of 1.0 M HCl and stirred for 2 h for complete desilylation the intermediate (Rf=0.8) as monitored by TLC analysis (EtOAc:Heptane, 3:1) to give the product (Rf=0.2). The hydrochloric acid in the reaction was quenched with triethylamine and the mixture was filtered through a pad of silica gel followed by exchange of the THF with ethyl acetate under rotary evaporation. The crystals were collected as a white solid and washed with cold ethyl acetate. β-lactam a: mp: 140 to 145° C.; $^1$H NMR (400 MHz, CDCl$_3$) (ppm): 2.26 (d, J=9.4 Hz, 1H), 4.96 (d, J=4.96 Hz, 1H, 5.12 (m, 1H), 4.15 (bm, 1H), 7.41 (m, 5H).

In another experiment, benzaldehyde was added to a 1.0 M THF solution of LHMDS (100 mL, 0.1 mol) at 0° C. and the mixture was stirred for 15 minutes followed by the addition of TMSCl (10 mL, 0.08 mol). To this solution was added tris(trimethylsilyloxy)ethylene (40 mL, 0.12 mol) and the mixture was stirred at −10 to −5° C. over 24 h. The mixture was warmed to ambient temperature over 2 h and quenched with saturated sodium bicarbonate (25 mL) and stirred at ambient temperature for 30 min and the layers were separated. The aqueous layer was back extracted with 1-butanol (200 mL) and the organic layers were combined and washed with brine (50 mL), dried over sodium sulfate, filtered through a pad of silica gel and concentrated to give a solid. The solid was taken up in hot ethyl acetate (800 mL) and the insoluble solids were filtered off through a pad of silica gel. The filtrate was concentrated under rotary evaporation at 40° C. to approximately 15 mL in volume to induce crystal formation. The mixture was cooled to ambient temperature and the crystals (10.73 g, 0.025 mol, 66% yield) were collected as a white powder. β-lactam a: mp: 140 to 145° C.; $^1$H NMR (400 MHz, CDCl$_3$) (ppm): 2.26 (d, J=9.4 Hz, 1H), 4.96 (d, J=4.96 Hz, 1H, 5.12 (m, 1H), 4.15 (bm, 1H), 7.41 (m, 5H).

EXAMPLE 5

Trimethylsilyl 2-(trimethylsilyoxy)acetate

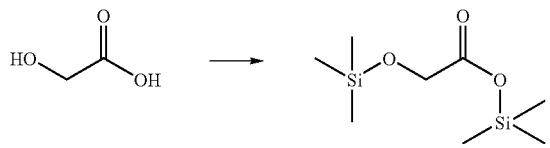

Glycolic acid (91.2 g, 2.4 mol) was dissolved in pyridine (194 g, 2.45 mol) and acetonitrile (600 mL) by mechanical stirring under nitrogen and reflux condensor. Trimethylsilylchloride (TMSCl, 260 g, 2.4 mol) was added via an addition funnel over 30 min. The mixture was stirred for 30 min and the hexanes (250 mL) was added and the phases were separated. To the bottom layer was added a second lot of hexanes (100 mL) and agitated vigorously for 5 minutes. Then the phases were separated and the hexanes layers were combined and concentrated under rotary evaporation at 30° C. to give 240 g (91% yield) of the known acetate.

EXAMPLE 6

Tris(trimethylsiloxy)ethane

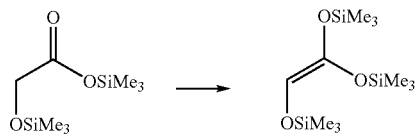

To a 0.5 M THF solution of LHMDS (200 mL, 0.1 mol) at 0° C. was added the trimethylsilyl-2-(trimethylsiloxy)acetate (23.9 mL, 0.1 mol) drop-wise over 15 minute and the mixture was stirred at this temperature for an additional 15 min to generate the lithium enolate. Trimethylsilyl chloride (12.5 mL, 0.1 mol) was added over 15 minutes to trap the enolate as the tris(trimethylsiloxy)ethene product. The mixture was warmed to ambient temperature and the THF solvent was removed by vacuum rotary evaporation at 40° C. to precipitate out the lithium chloride. The mixture was taken up in 300 mL of hexanes and 5 mL of triethylamine and stirred for 5 min; the salt was allowed to settle. The supernatant was filtered through a pad of diatomaceous earth twice to give a clear solution. The solution was concentrated under rotary evaporation to give the lightly yellow colored oil product. The solution was concentrated under rotary evaporation to give the lightly yellow colored oil product identical to the commercial product. Bp=90° C. at 1 mmHg.

EXAMPLE 7

N-trimethylsilyl-3-trimethylsiloxy-4-phenyl-azetidin-2-one

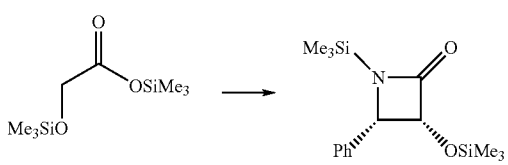

A one-pot procedure for the synthesis of previously unreported N-trimethylsilyl beta-lactam from the trimethylsilyl-2-trimethylsiloxy-acetate has been discovered to be an efficient economical method not requiring cryogenic cooling. To a magnetically stirring solution of hexamethyldisilazane (390 g, 2.42 mol) in dry 1,2-dimethoxyethane (505 mL) under nitrogen with a circulation chiller at 0° C. was added a 2.5 M solution of n-butyllithium (840 mL, 2.1 mol) at a rate so as to control the exothermic reaction temperature to <30° C. (over 45 min) to generate the required LHMDS base in situ. Once the LHMDS solution temperature has reached <10° C., a neat mixture of TMSCl (119.5 g, 1.1 mol) and the trimethylsilyl-2-(trimethylsiloxy)acetate (240 g, 1.1 mol) was added over 15 minutes to give the tris(trimethylsiloxy)ethene in situ. Then neat benzaldehyde (106.12 g, 1.0 mol) was added at a rate so as to control the exothermic reaction temperature to <25° C. to give the N-trimethylsilyl-benzaldimine in situ. The mixture was allowed to react at ambient temperature (22° C.) until $^1$HNMR monitoring indicated that the disappearance of the ketene acetal resonance at 5.4 ppm (CDCl$_3$) occurred at 12 h of reaction time. The reaction mixture was quenched with trimethylchlorosilane (TMSCl, 108.64 g, 1.0 mol), triethylamine (25.3 g, 0.25 mol) followed by acetic acid (6.0 g, 0.1 mol) while keeping the exothermic reaction temperature to <22° C. The mixture was diluted with hexanes (500 mL) and the resulting lithium chloride salt was filtered off through a pad of celite (200 g) followed by filter cake washing with hexanes (250 mL). The filtrate was concentrated under rotary vacuum evaporation to a residue. The residue was taken up in hexanes (500 mL) and allowed to stand at −25° C. to induce crystal formation. The white crystals were collected by vacuum filtration, washed with cold −20° C. hexanes (200 mL), and dried to a constant weight of 152 g. The filtrate was concentrated to a residue, taken up in hexanes (200 mL), and recrystallized as previous to give a second crop of 32 g. The crops were combined (184 g, 60% yield) after HNMR analysis to be pure cis-N-trimethylsilyl-3-trimethylsiloxy-4-phenyl-azetidin-2-one. Mp: 53 to 55° C. $^1$H NMR (400 MHz, CDCl$_3$) δ (ppm): 0.11 (s, 9H), 0.14 (s, 9H), 4.63 (d, J=5.01 Hz, 1H), 5.06 (d, J=5.01 Hz, 1H), 7.31 (m, 5H).

EXAMPLE 8

Cis-3-Trimethylsiloxy-4-phenyl-azetidin-2-one

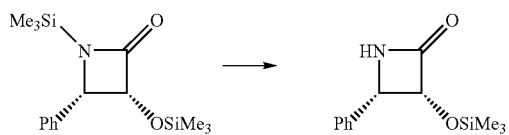

To a solution of N-trimethylsilyl-3-trimethylsiloxy-4-phenyl-azetidin-2-one (140 g, 0.46 mol) in hexanes (600 mL) at ambient temperature was added triethylamine (101 g, 1 mol), methanol (22 g, 0.7 mol) and the mixture was stirred for 15 minutes resulting in crystal formation of the N-desilylated product. The mixture was cooled to 0° C. for 15 min and the white crystals were collected by vacuum filtration, washed with cold hexanes, and dried to a constant weight of 94 g (87% yield). Mp: 118 to 120° C., $^1$H NMR (400 MHz, CDCl$_3$) δ (ppm): −0.08 (s, 9H), 4.79 (d, J=4.4 Hz, 1H), 5.09 (dd, J=4.4, 2.7 Hz, 1H), 6.16 (bm, 1H), 7.3 to 7.4 (m, 5H).

EXAMPLE 9

Cis-3-hydroxy-4-phenyl-azetidin-2-one

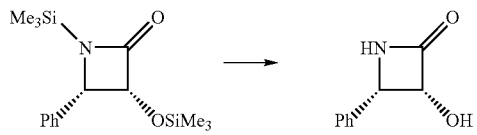

To a heterogeneous solution of N-trimethylsilyl-3-trimethylsiloxy-4-phenyl-azetidin-2-one (150 g, 0.49 mol) in methanol (500 mL) was added a catalytic amount of trimethylchlorosilane (1.08 g, 1 mmol) and the mixture was stirred at ambient temperature to give a clear solution. Thin layer chromatography (TLC) monitoring of the reaction eluting with ethyl acetate and hexanes (3:1) indicated that complete conversion was achieved after 15 minutes. The reaction mixture was quenched with triethylamine (10.1 g, 0.1 mol) and the methanol was removed under rotary evaporation at 40° C. until crystals formed. Ethyl acetate (300 mL) was added and the evaporation was continued to remove the remaining methanol to give a thick slurry before cooling to 0 to 5° C. for 20 minutes. The white crystals were collected via vacuum filtration following by washing with cold 0° C. ethyl acetate (75 mL) and dried to constant weight of 75 g (94% yield) of the desire product described previously.

EXAMPLE 10

1-(triethylsilyloxy)-1,2-bis(trimethylsilyloxy)ethane

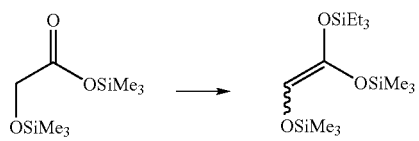

To a solution of diisopropylamine (15.5 mL, 0.11 mol) in THF (100 mL) at −78° C. was added a 1.6 M hexanes solution of n-butyl lithium (70 mL, 0.11 mol) over 15 minutes. After stirring for an additional 15 minutes at this temperature, triethylsilylchloride (16.7 mL, 0.1 mol) was added over 10 minutes followed by the addition of trimethylsilyl-2-(trimethylsiloxy)acetate (24.4 mL, 0.1 mol) over 30 minutes. The reaction was stirred at −78° C. for 30 minutes and warmed to ambient temperature by removing the cryogenic bath. The THF solvent was removed by vacuum rotary evaporation at 40° C. to precipitate out the lithium chloride. The mixture was taken up in 300 mL of hexanes and 5 mL of triethylamine and stirred for 5 min and the salt was allowed to settle. The supernatant was twice filtered through a pad of diatomaceous earth to give clear solution. The solution was concentrated under rotary evaporation to give the lightly yellow colored oil product as a mixture of geometrical isomers (4:1).

EXAMPLE 11

Triethylsilyl-2-(triethylsilyloxy)acetate

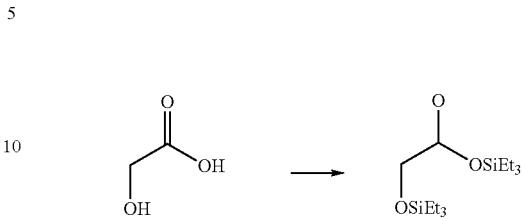

Glycolic acid (76.05g, 1 mol) was dissolved in dry pyridine (164 mL, 2 mol) and the mixture was cooled to with ice-water bath with stirring. Neat triethylsilyl chloride (115 g, 1 mol) was added drop-wise to control the exotherm to less than 40° C. Pyridinium chloride precipitated as a free flowing solid. Heptane (500 mL) was added to aid the agitation. The second equivalent of neat triethylsilylchloride was added and the mixture was stirred as ambient temperature (22 to 40° C.) for 30 minutes until the reaction was complete. The mixture was further diluted with heptane (1 L) and the salt was allowed to precipitate out. The heptane layer was siphoned into the rotary evaporator through a medium porous inline filter and concentrated to give a clear oil (215 g, 0.98 mol) of the triethylsilyl-2-(triethylsilyloxy)acetate ester. The oil was further purified by vacuum distillation. Bp: 128 to 130° C., 1.5 mmHg. $^1$H NMR (400 MHz, CDCl$_3$) δ (ppm): 0.64 (q, J=8.04 Hz, 6H), 0.78 (q, J=8.04, 6H), 0.97 (t, J=8.04, 2×9H), 4.2 (s, 2H).

EXAMPLE 12

Tris(triethylsiloxy)ethane

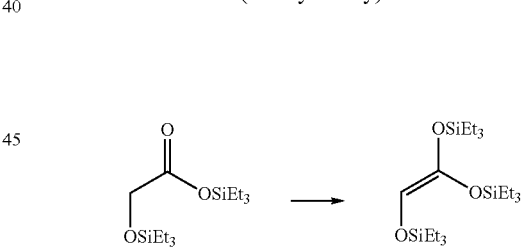

The ester was added to a 0.5 M THF (200 mL, 0.1 mol) solution over 15 minutes and the mixture was stirred at this temperature for an additional 15 minutes to generate the lithium enolate. Triethylsilyl chloride (16.7 mL 0.1 mol) was added over 15 minutes to trap the enolate as the tris(triethylsiloxy)ethene product. The mixture was warmed to ambient temperature and the THF solvent was removed by vacuum rotary evaporation at 40° C. to precipitate out the lithium chloride. The mixture was taken up in 300 mL of hexanes and 5 mL of triethylamine and stirred for 5 minutes while the salt was allowed to settle. The supernatant was twice filtered through a pad of diatomaceous earth to give a clear solution. The solution was concentrated under rotary evaporation to give the lightly yellow colored oil product.

EXAMPLE 13

1,2-bis(triethylsilyloxy)-1-(trimethylsilyloxy)ethene

To a solution of diisopropylamine (15.5 mL, 0.11 mol) in THF (100 mL) at −78° C. was added a 1.6 M hexanes solution of n-butyl lithium (70 mL, 0.11 mol) over 15 minutes. After stirring for an additional 15 minutes at this temperature, triethylsilylchloride (16.7 mL, 0.1 mol) was added over 10 minutes followed by the addition of triethylsilyl-2-(triethylsiloxy)acetate (37.6 g, 0.1 mol) over 30 minutes. The reaction was stirred at −78° C. for 30 minutes and warmed to ambient temperature by removing the cryogenic bath and the THF solvent was removed by vacuum rotary evaporation at 40° C. to precipitate the lithium chloride. The mixture was taken up in 300 mL of hexanes and 5 mL of triethylamine and stirred for 5 minutes and the salt was allowed to settle. The supernatant was twice filtered through a pad of diatomaceous earth to give a clear solution. The solution was concentrated under rotary evaporation to give the lightly yellow colored oil product as a 1:1 mixture of geometrical isomers.

EXAMPLE 14

Cis-3-triethylsiloxy-4-phenyl-azetidin-2-one

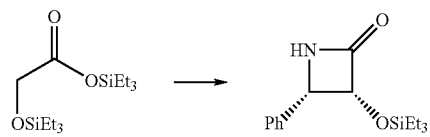

To a magnetically stirring solution of hexamethyldisilazane (39 g, 0.242 mol) in dry 1,2-dimethoxyethane (50 mL) under nitrogen with a circulation chiller at 0° C. was added a 2.5 M solution of n-butyllithium (84.0 mL, 0.21 mol) at a rate so as to control the exothermic reaction temperature to <30° C. (over 15 min) to generate the required LHMDS base in situ. Once the LHMDS solution temperature reached <−30° C., a neat solution of TMSCl (12 g, 0.11 mol) was added and the triethylsilyl-2-(triethylsiloxy)acetate (33.5 g, 0.11 mol) was added over 15 minutes to give the 1,2-bis(triethylsilyloxy)-1-(trimethylsilyloxy)ethene in situ as a mixture of geometrical 1 isomers (6:1). Then, neat benzaldehyde (10.6 g, 0.10 mol) was added at a rate so as to control the exothermic reaction temperature to <−25° C. to give the N-trimethylsilylbenzaldimine in situ. The hexanes solvent was removed under vacuum and the mixture was allowed to react at ambient temperature (22° C.) until ¹HNMR monitoring indicated that the disappearance of the ketene acetal resonance at 5.43 ppm (CDCl₃) had occurred after 14 h of reaction time. The reaction mixture was quenched with trimethylchlorosilane (TMSCl, 10.8 g, 1.0 mol), triethylamine (2.53 g, 0.025 mol) and acetic acid (0.60 g, 0.01 mol) while keeping the exothermic reaction temperature to <22° C. The mixture was diluted with hexanes (50 mL) and resulting lithium chloride salt was filtered off through a pad of celite (20 g) followed by washing the filter cake with hexanes (25 mL). The filtrate was concentrated under rotary vacuum evaporation to a residue. The residue was taken up in hexanes (50 mL), triethylamine (5 mL) and methanol at ambient temperature and stirred for 15 minutes. TLC analysis of the mixture eluting with ethyl acetate:hexanes (2:1) indicated complete conversion to the desired product ($R_f$=0.45) after 10 minutes of reaction time. The mixture was then diluted with ethyl acetate (100 mL), filtered through a pad of silica gel (25 g) and concentrated until crystals formed. The crystals were collected via vacuum filtration, washed with hexanes and dried to a constant weight of 7.68 g as a white free flowing powder. Upon standing for 2 h at ambient temperature, the filtrate gave 2.8 g of a second crop after harvest. The combined yield was 38%. Mp: 98 to 100° C. ¹H NMR (400 MHz, CDCl₃) δ (ppm): 0.44 (m, 6H), 0.78 (t, J=8.0 Hz, 9H), 4.80 (d, J=4.80, 1H), 5.08 (dd, 4.80, 2.80, 2H), 6.18 (bs, 1H), 7.28 to 7.38 (m, 5H).

EXAMPLE 15

Cis-N-t-butoxycarbonyl-3-(2-methoxy-2-propoxy)-4-phenyl-azetidin-2-one

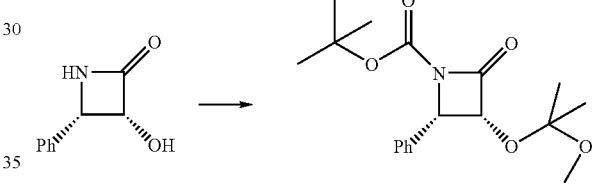

Racemic cis-3-hydroxy-4-phenyl-azetidin-2-one (100 g, 0.61 mol) was dissolved in THF (2.7 L) at ambient temperature at approximately 25 mL/g then cooled to −10 to −15° C. TsOH monohydrate catalyst (3.5 g, 0.018 mol, 3 mol %) was added and then 2-methoxy-2-propene (65 mL, 1.1 to 1.2 eq) was added drop-wise to control the exothermic reaction. The reaction was monitored by TLC and the 2-methoxy-2-propene (2.9 mL) was charged as needed until the disappearance of the starting material was achieved. Triethylamine (85 mL, 0.612 mol) was added to quench the TsOH catalyst. Di-tert-butyldicarbonate (160.5 g, 0.735 mol, 1.2 eq) was added along with DMAP (2.25 g, 0.018 mol, 3 mol %) and the reaction was allowed to proceed at ambient temperature until complete. The mixture was diluted with heptane (1.97 L) approximately equal in volume to the THF used and filtered through a bed of silica gel (100 g) to remove the polar catalysts. The filter cake was washed with 1 L of a 1:1 mixture of ethyl acetate:heptane to ensure complete product recovery. The filtrate was concentrated until crystal formation occurred. Crystals were collected and washed with ice-cold heptane containing 2% triethylamine. The powder was dried to constant weight of 161.0 g (0.48 mol, 78%) under vacuum (0.1 mmHg) at ambient (22° C.) temperature. Mp: 90 to 92° C., ¹H NMR (400 MHz, CDCl₃) δ (ppm): 0.92 (s, 3H), 1.21 (s, 3H), 1.37 (s, 9H), 1.58 (s, 3H), 3.12 (s, 3H), 5.03 (d, J=5.69 Hz, 1H), 5.17 (d, J=5.69 Hz, 1H), 7.33 (m, 5H).

EXAMPLE 16

Racemic cis-3-trimethylsilyloxy-4-phenyl-azetidin-2-one

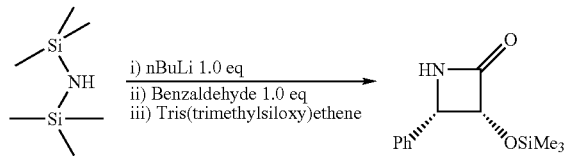

To a solution of hexamethyldisilazane (HMDS, 460 mL, 2.2 mol) in anhydrous dimethoxyethane (200 mL) at 0° C. was added a 2.5 M solution of n-butyllithium (nBuLi, 800 mL, 2.0 mol) over 45 min to maintain the reaction temperature at less than 40° C. After the addition, benzaldehyde was added to the reaction mixture over 1 h to maintain the reaction temperature at less than 40° C. After the addition was complete the mixture was cooled to 0° C. and tris(trimethylsiloxy) ethane (643 g, 2.2 mol) was added and the mixture was stirred until reaction was complete (12 h); reaction completion was determined by the disappearance of the starting ethene material. The reaction mixture was quenched with trimethylsilylchloride (TMSCl, 217.28 g, 1.0 eq), triethylamine (50 mL) and acetic acid (20 mL) and diluted with ethyl acetate (1.0 L). The lithium salt was filtered off via a sintered funnel. The filtrate was concentrated to dryness. The solid was taken up in heptane (1.0 L) and treated with methanol (96 g, 1.5 eq) at 20 to 40° C. to give crystals of the product. The solid product was collected via vacuum filtration through a Buchner funnel and washed with cold 15% ethyl acetate in heptane. The solid was taken up in ethyl acetate (1.5 L) and washed with brine, dried over sodium sulfate (200 g) and concentrated to give a white powder. Mp: 118 to 120° C., $^1$H NMR (400 MHz, CDCl$_3$) δ (ppm): −0.08 (s, 9H), 4.79 (d, J=4.4 Hz, 1H), 5.09 (dd, J=4.4, 2.7 Hz, 1H), 6.16 (bm, 1H), 7.3 to 7.4 (m, 5H).

EXAMPLE 17

Racemic cis-N-t-butoxycarbonyl-3-trimethylsilyloxy-4-phenyl-azetidin-2-one

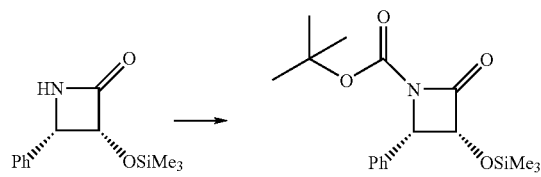

Racemic cis-3-trimethylsilyloxy-4-phenyl-azetidin-2-one (11.5 g, 48.9 mmol) was dissolved in tetrahydrofuran (THF, 250 mL) at ambient temperature under nitrogen and di-tert-butyldicarbonate was added along with N,N-4-dimethylaminopyridine (DMAP, 0.185 g, 1.5 mmol) and the mixture was magnetically stirred until the evolution of gas ceased. The mixture was filtered through a bed of silica gel (10 g) and concentrated on the rotary evaporator to give a white solid product. The product was washed with cold heptane (50 mL) and collected by vacuum filtration and dried to a constant weight of 12.3 g (75% yield) at ambient temperature and vacuum (0.2 mmHg). Mp: 75 to 77° C., $^1$H NMR (400 MHz, CDCl$_3$) δ (ppm): −0.07 (s, 9H), 1.38 (s, 9H), 5.01 (d, J=5.6 Hz, 1H), 5.06 (d, J=5.6 Hz, 1H), 7.26 to 7.38 (m, 5H).

EXAMPLE 18

Racemic (±)-Cis-N-t-butoxycarbonyl-3-diphenylmethylsilyloxy-4-phenyl-azetidin-2-one

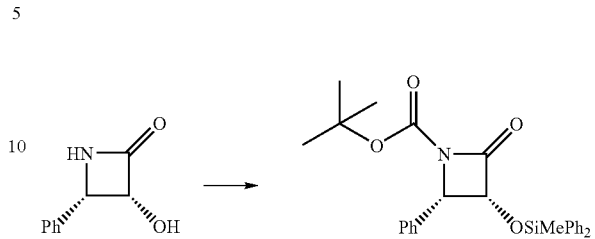

To a solution of racemic (±)-cis-3-hydroxy-4-phenyl-azetidin-2-one (4.5 g, 27.8 mmol) in THF (70 mL) under nitrogen was added triethylamine (8.4 g, 83.4 mmol), DMAP (100 mg, 0.83 mmol) and cooled to 0° C. Diphenylmethylsilyl chloride (7.1 g, 30.6 mmol) was added dropwise and the mixture was stirred at 0° C. for 30 min until complete disappearance of the starting material as shown by TLC eluting with 3:1 mixture of ethyl acetate and heptane. Di-tert-butyl-dicarbonate (Boc$_2$O, 6.68 g, 30.6 mmol) was added and the mixture was stirred at ambient temperature for 3 h for complete conversion to the desired product as shown by TLC (3:1 ethyl acetate:heptane). The mixture was diluted with heptane (150 mL) and filtered through silica gel (20 g) and the filtrate was concentrated to a solid. The solid was recrystallized from heptane (150 mL) to give a white powder (9.5 g, 74%). Mp 98° C., $^1$H NMR (400 MHz, CDCl$_3$) δ (ppm): 0.46 (s, 3H), 1.39 (s, 9H), 4.94 (d, J=5.5 Hz, 1H), 5.04 (d, J=5.5 Hz, 1H), 7.2 to 7.4 (m, 15 H).

EXAMPLE 19

Resolution of (±)-Cis-3-hydroxy-4-(2-furyl)-azetidin-2-one (±)-Cis-3-hydroxy-4-(2-furyl)-azetidin-2-one (500 g, 3.265 mol) was treated with N-t-Boc-L-proline (378.83 g, 1.76 mol) in the presence of 0.5 equivalents of p-toluenesulfonyl chloride (335.53 g, 1.76 mol) and 1-methyl-imidazole (303.45 g, 3.7 mol) at −78° C. for 12 hours. The mixture was filtered through 5 kg of silica gel. The undesired (−)-β-lactam enantiomer of t-Boc-L-proline ester was removed by trituration with water. The desired enantiomer was recovered by azeotropic removal of the water with 2-methyl-1-propanol and recrystallized from ethyl acetate to give the desired (+)-cis-3-hydroxy-4-(2-furyl)-azetidin-2-one. The optical purity after recrystallizing from ethyl acetate was greater than 98%. mp: 133 to 135° C.; $[\alpha]^{20}$D=+109.5 (MeOH, c=1.0), $^1$H NMR (400 MHz, CDCl$_3$) (ppm): 2.69 (bs, 1H), 4.91 (d, J=4.96 Hz, 1H), 5.12 (bs, 1H), 6.10 (bs, 1H), 6.34 (dd, J=3.32, 3.32 Hz, 1H), 6.47 (d, J=3.32 Hz, 1H), 7.49 (m, 1H).

EXAMPLE 20

Resolution of (±)-Cis-3-hydroxy-4-phenyl-azetidin-2-one (±)-Cis-3-hydroxy-4-phenyl-azetidin-2-one (60 g, 0.368 mol) was treated with N-cBz-L-proline (45 g, 0.184 mol) in the presence of 0.5 equivalents of p-toluenesulfonyl chloride (35 g, 0.184 mol) and 1-methylimidazole (45 mL, 0.56 mol) at −78° C. for 12 hours. After concentration of the reaction mixture and filtration through silica gel to remove the 1-methylimidazolium tosylate salt, the desired diastereomer was crystallized from ethyl acetate to give 14.5 g (48%) of a white solid. This protocol resulted in kinetic resolution of the enantiomeric mixture to give the desired (+)-cis-3-hydroxy-4-phenyl-azetidin-2-one. The optical purity after recrystallizing from ethyl acetate was greater than 98%. mp: 175 to 180° C.; $[\alpha]_{578}^{20}$=+202 (MeOH, c=1.0), $^1$H NMR (400 MHz, CDCl$_3$) (ppm): 2.26 (d, J=9.4 Hz, 1H), 4.96 (d, J=4.96 Hz, 1H), 5.12 (m, 1H), 4.15 (bm, 1H), 7.41 (m, 5H).

EXAMPLE 21

Kinetic Resolution of (±)-Cis-3-hydroxy-4-phenyl-azetidin-2-one

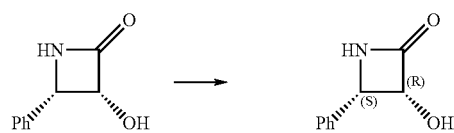

To a dry 250-mL round bottom flask under nitrogen was added acetonitrile (50 mL) and 1-methyl-imidazole (28 g, 0.2 mol) and the mixture was cooled to 0 to 5° C. Methanesulfonyl chloride (MsCl, 17.44 g, 0.1 mol) was added slowly to the mixture to control the exothermic reaction. After the reaction temperature was cooled to 0-5° C., N-cBz-L-proline (25 g, 0.1 mol) was added and the mixture was stirred at this temperature for 30 min. In a separate 3-L flask under nitrogen, racemic (±)-cis-3-hydroxy-4-phenyl-azetidin-2-one (16.3 g, 0.1 mol) was dissolved in acetone (1 L) and cooled to −65 to −78° C. and stirred mechanically. Once the temperature reached below −65° C., the content of the flask containing the proline reagent was added to the acetone solution of the racemic starting material. The mixture was kept at this temperature for a minimum of 6 h and a white precipitate was observed. The precipitate was allowed to settle and supernatant was transferred to the rotary evaporator as a cold solution (circa −45° C.) via vacuum suction through an immersion filter. The acetone was removed and exchanged with ethyl acetate (500 mL) and triethylamine (50 g, 5 eq) base. The resulting salt was filtered off and the filtrate was concentrated to approximately 100 mL and crystal formation was allowed to occur. The crystals were collected via vacuum filtration through a Buchner funnel, washed with cold ethyl acetate, and dried under vacuum (0.1 mmHg) at ambient temperature to a constant weight of 7.5 g (46% yield).

The efficiency of the kinetic resolution was determined by the ratio of the diastereomeric ester (SSS:RRS) of the beta-lactam with the Boc-L-proline via $^1$HNMR according to Scheme 7. In Table 3, TsCl is tosyl chloride, Boc$_2$O is di-tert-butyldicarbonate, MsCl is mesyl chloride and MstCl is mesityl chloride.

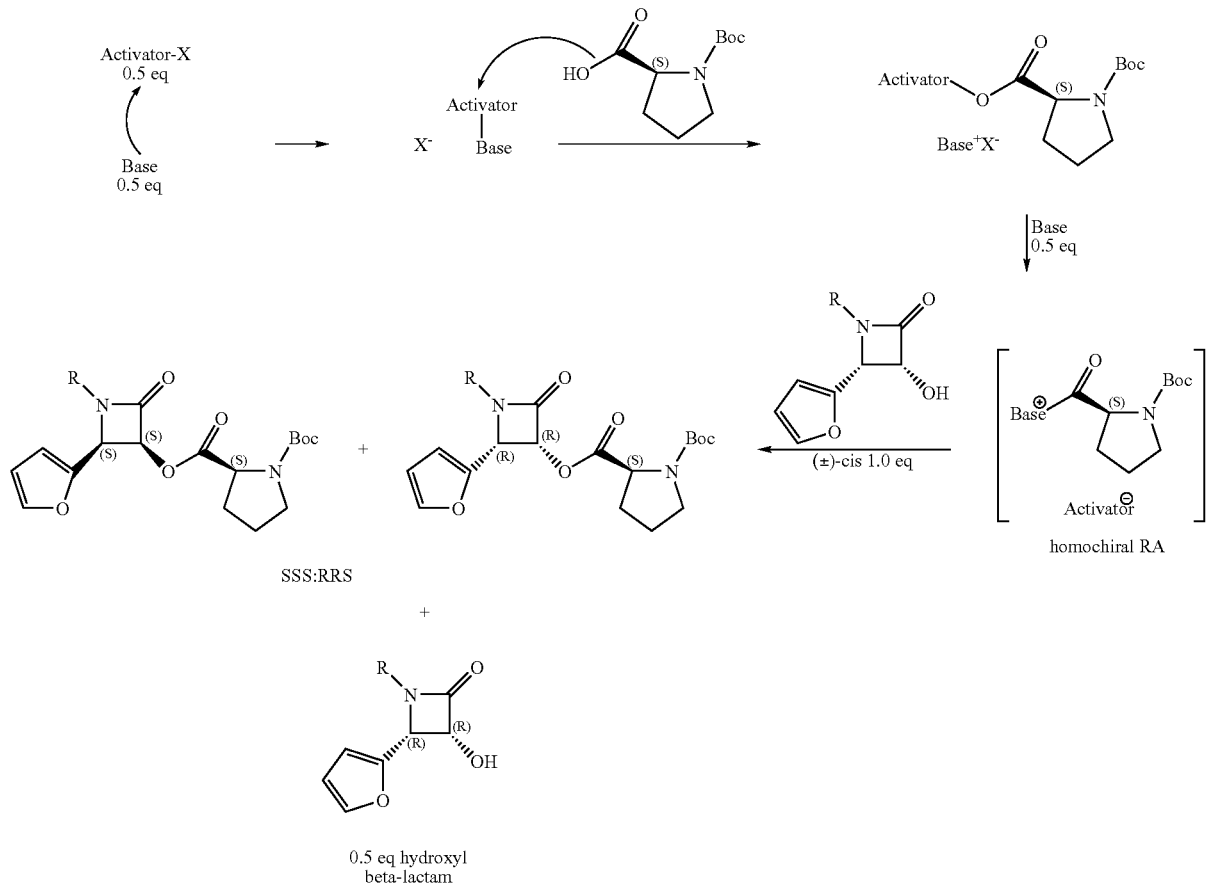

TABLE 3

| Entry | R | Activator | Base | Temp (°C.) | Solvent | Time h/% Conv. | Dr SSS:RRS |
|---|---|---|---|---|---|---|---|
| 1 | PMP | TsCl | 1-methyl-imidazole | −78 | DME/ACN | 3/50 | 10:1 |
| 2 | H | TsCl | 1-methyl-imidazole | −78 | DME/ACN | 3/50 | 8.5:1 |
| 3 | H | TsCl | 1-methyl-imidazole | 0 | ACN | 3/50 | 2.6:1 |
| 4 | H | TsCl | triethylamine | 0 | ACN | 3/15 | 1:2.9 |
| 5 | H | TsCl | 1-methylbenzimidazole | −78 to 22 | DME/ACN | 12/50 | 8:1 |
| 6 | H | TsCl | 1,2-dimethylimidazole | −78 | DME/ACN | 3/50 | 4.5:1 |
| 7 | H | TsCl | Pyridine | −40 | Pyridine | 6/20 | 6.8:1 |
| 8 | H | TsCl | Pyridine | 0 | Pyridine | 3/50 | 3.8:1 |
| 9 | H | TsCl | DMAP | 0 | ACN | 3/50 | 1:1 |
| 10 | H | Boc$_2$O | 1-methyl-imidazole | 0 | ACN | 1/30 | 2:1 |
| 11 | H | MsCl | 1-methyl-imidazole | −40 | DME/ACN | 4/50 | 4.3:1 |
| 12 | H | MsCl | Pyridine | −40 | Pyridine | 6/10 | 5:1 |
| 13 | H | MstCl | 1-methyl-imidazole | −40 | DME/ACN | 12/50 | 4.3:1 |

EXAMPLE 22

Classical Resolution of (±)-Cis-3-hydroxy-4-phenyl-azetidin-2-one

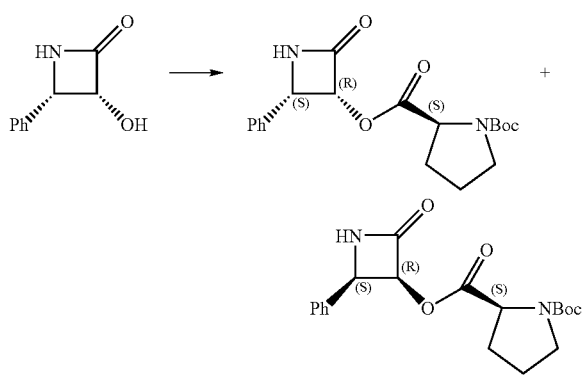

As an alternative to the above kinetic resolution, the diastereomeric mixture of the proline esters was separated via recrystallization from ethyl acetate. Subsequent hydrolysis of the proline esters separately would yield both enantiomers of the beta-lactam and recover the chiral amino acid. Thus, to a solution of N-methyl-imidazole (12 g, 150 mmol) in acetonitrile (80 mL) at 0° C. was added methanesulfonyl chloride (MsCl, 5.7 g, 50 mmol) and stirred for 15 minutes until the exothermic reaction temperature was stable at 0° C. To this solution was added N-Boc-L-Proline (11 g, 50 mmol) portion-wise and stirred at 0° C. for 30 minutes. Racemic (±)-cis-3-hydroxy-4-phenyl-azetidin-2-one (8.2 g, 50 mmol) was added portion-wise and the mixture was stirred at this temperature until TLC monitoring (3:1/ethyl acetate:hexanes) indicated complete conversion to the ester products after 1 h. The acetonitrile solvent was removed under rotary evaporation at 40° C. and the residue was taken up in ethyl acetate (500 mL), washed with water (100 mL), saturated aqueous sodium bicarbonate, brine, and dried over sodium sulfate. The drying agent was removed by vacuum filtration and the filtrate was concentrated to give 18 g of solid. A portion (7 g) of the mixture was taken up in 40° C. ethyl acetate (60 mL) and crystals (1.5 g) were formed at 40° C.; the crystals were collected and shown to be the desired 3R,4S-diastereomer of the (2S)-tert-butyl (3R,4S)-2-oxo-4-phenylazetidin-3-yl pyrrolidine-1,2-dicarboxylate. $^1$H NMR (400 MHz, CDCl$_3$) δ (ppm): This diastereomer exists as a 1.7:1 (δ (ppm)5.84:5.87) pair of diastereomers on the NMR timescale as typified by the characteristic chemical shift change of the starting material C3-carbinol proton from a multiplet at 5.12 ppm downfield to 5.8 ppm as a pair of doublet of doublets (J=4.68, 2.57 Hz) in the esterified product.

The filtrate was allowed to stand at ambient temperature for 5 h to give a second form of crystals (2.4 g) shown to be the 3S,4R-diastereomer of (2S)-tert-butyl (3S,4R)-2-oxo-4-phenylazetidin-3-yl pyrrolidine-1,2-dicarboxylate. $^1$H NMR (400 MHz, CDCl$_3$) δ (ppm): This diastereomer exists as a 1:1.9 (δ (ppm)5.90:5.94) pair of diastereomers on the NMR timescale as typified by the characteristic chemical shift change of the starting material C(3)-carbinol proton from a multiplet at 5.12 ppm downfield to 5.9 ppm as a pair of doublet of doublets (J=4.68, 2.57 Hz) in the esterified product.

Differences between the classical thermodynamic controlled resolution and the kinetic resolution are that a stoichiometric amount of reagents are used and careful low temperature control is not critical. However, classical resolution requires one additional step of de-esterification of the diastereomeric ester to recover the desired C3-hydroxy substituted β-lactam.

EXAMPLE 23

Optically Active (+)-cis-3-trimethylsilyloxy-4-phenyl-azetidin-2-one

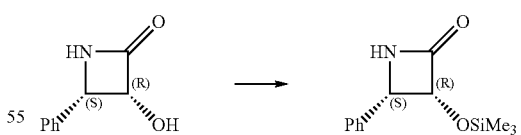

Optically active (+)-cis-3-hydroxy-4-phenyl-azetidin-2-one (3.4 g, 20.8 mmol) was dissolved in THF (30 mL) along with triethylamine (5.8 g, 57.4 mmol) and DMAP (76 mg, 0.62 mmol) at 0° C. Trimethylsilyl chloride (2.4 g, 22 mmol) was added dropwise and the mixture stirred for 30 min. TLC (3:1 ethyl acetate:heptane) showed complete conversion to the less polar product. The mixture was diluted with ethyl acetate (30 mL), washed with saturated aqueous sodium bicarbonate (15 ml), brine (15 ml), and dried over sodium sulfate (5 g). The sodium sulfate was filtered and the filtrate was concentrated and solvent exchanged with heptane (50 mL) to give a white powder. The powder was collected via vacuum filtration through a Buchner funnel and dried under vacuum (<1 mmHg) at ambient temperature to a constant weight of 3.45 g (72% yield). mp: 120 to 122° C., $[\alpha]^{22}_{578}$=+ 81.9 (MeOH, 1.0), $^1$H NMR (400 MHz, CDCl$_3$) δ (ppm): −0.08 (s, 9H), 4.79 (d, J=4.4 Hz, 1H), 5.09 (dd, J=4.4, 2.7 Hz, 1H), 6.16 (bm, 1H), 7.3 to 7.4 (m, 5H).

EXAMPLE 24

Optically Active (+)-Cis-N-t-butoxycarbonyl-3-trimethylsilyloxy-4-phenyl-azetidin-2-one

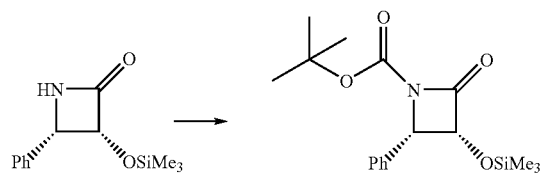

To a solution of hexamethyldisilazane (HMDS, 460 mL, 2.2 mol) in anhydrous dimethoxyethane (200 mL) at 0° C. was added a 2.5 M solution of n-butyllithium (nBuLi, 800 mL, 2.0 mol) over 45 min to maintain the reaction temperature at less than 40° C. After the addition, benzaldehyde was added to the reaction mixture over 1 h to maintain the reaction temperature at less than 40° C. After the addition was complete the mixture was cooled to 0° C. and tris(trimethylsiloxy)ethene (643 g, 2.2 mol) was added and the mixture was stirred until reaction was complete (12 h); reaction completion was determined by the disappearance of the starting ethene material. The reaction mixture was quenched with trimethylsilylchloride (TMSCl, 217.28 g, 1.0 eq), triethylamine (50 mL) and acetic acid (20 mL) and diluted with ethyl acetate (1.0 L). The lithium salt was filtered off via a sintered funnel. The filtrate was concentrated to dryness. The solid was taken up in heptane (1.0 L) and treated with methanol (96 g, 1.5 eq) at 20 to 40° C. to give crystals of the product. The solid product was collected via vacuum filtration through a Buchner funnel and washed with cold 15% ethyl acetate in heptane. The solid was taken up in ethyl acetate (1.5 L) and washed with brine, dried over sodium sulfate (200 g) and concentrated to give a white powder. Mp: 118 to 120° C., $^1$H NMR (400 MHz, CDCl$_3$) δ (ppm): −0.08 (s,9H), 4.79 (d, J=4.4 Hz, 1 H), 5.09 (dd, J=4.4, 2.7 Hz, 1 H), 6.16 (bm, 1H), 7.3 to 7.4 (m, 5H).

EXAMPLE 25

(+)-Cis-N-benzoyl-3-(2-methoxy-2-propoxy)-4-phenyl-azetidin-2-one from (+)-Cis-3-hydroxy-4-phenyl-azetidin-2-one

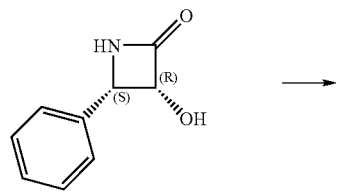

-continued

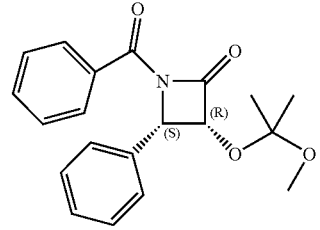

(+)-Cis-3-hydroxy-4-phenyl-azetidin-2-one (13.67 g, 83.8 mmol) was dissolved in anhydrous THF (275 mL) under nitrogen at a concentration of 20 mL/g, cooled to −15 to −10° C., and TsOH monohydrate (0.340 g, 1.8 mmol) was added. To the reaction at this temperature was added drop-wise 2-methoxy-2-propene (6.49 g, 90 mmol). A sample of the reaction mixture was quenched with 5% TEA in ethyl acetate and the conversion to the intermediate was monitored by TLC (3:1 ethyl acetate:Heptane). Once the reaction was complete, triethylamine (25.5 g, 251 mmol) and DMAP (0.220 g, 1.8 mmol) were added. Benzoyl chloride (12.95 g, 92.18 mmol) was added to the reaction mixture before warming to ambient temperature and stirred until the conversion to (+)-cis-N-benzoyl-3-(2-methoxy-2-propoxy)-4-phenyl-azetidin-2-one was complete (3 to 5 h). The mixture was diluted with heptane equal in volume to the THF. The solid salt was filtered off and the mixture was washed with water, saturated aqueous sodium bicarbonate and brine. The organic phase was filtered through silica gel and the filtrate was concentrated until crystals formed. The solid was collected by vacuum filtration and washed with heptane:triethylamine (95:5) as a white solid (21.0 g, 61.9 mmol, 74% yield). Mp:98 to 100° C. $^1$H NMR (400 MHz, CDCl$_3$) δ (ppm): 0.99 (s, 3H), 1.54 (s, 3H), 3.15 (s, 3H), 5.27 (d, J=6.3 Hz, 1H), 5.41 (d, J=6.3 Hz, 1H), 7.30 to 7.43 (m, 5H), 7.47 (t, J=7.54 Hz, 2H), 7.59 (m, J=7.54 Hz, 1H)), 8.02 (m, J=7.54 Hz, 2H).

EXAMPLE 26

7,10—O—(1,1,3,3-tetramethyl-1,3-disiloxanediyl)-10-DAB

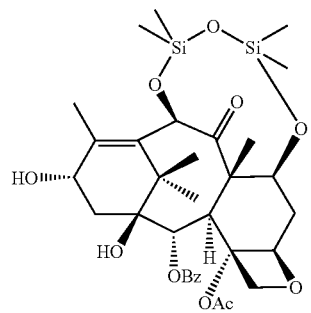

Typically, 10-DAB (108.96 g, 0.20 mol) was dissolved in THF at approximately 20 to 25 mL/g (2.2 L) along with 2.5 eq of DMAP (61.08 g, 0.5 mol). To this solution was added 1,3-dichloro-1,1,3,3-tetramethyldisiloxane (42.67 g, 0.21 mol) at ambient temperature until the conversion the product was complete by TLC (3:1 ethyl acetate/heptane). The reaction mixture then was diluted with heptane (2 L) to precipitate out the DMAP-HCl salt and filtered through silica gel (104.5 g). The filter cake was washed with a 1:1 mixture of ethyl acetate and heptane (800 mL) to ensure complete product recovery. The filtrate was stabilized with triethylamine (14 mL) and concentrated until crystals formed. The mixture was chilled to 0° C. for 30 min and the white solid was collected via a Buchner funnel and washed with ice-cold 20% ethyl acetate in heptane (500 mL). The filter cake was dried under vacuum (0.1 mmHg) at 50° C. to constant weight of 109 g. The filtrate was filtered thru silica gel and concentrated to give 13.2 g of a second crop of crystals. The total yield was 122.2 g (0.18 mol, 90%), at 99.2% HPLC purity. mp: 220 to 223° C. $^1$H NMR (400 MHz, CDCl$_3$) δ (ppm): 0.07 (s, 3H), 0.11 9 (s, 3H), 0.14 (s, 3H), 0.41 (s, 3H), 1.09 (s, 6H), 1.51 (s, 1H), 1.89 (ddd, J=13.9, 12.4, 2.2 Hz, 1H), 1.99 (d, J=4.6 Hz), 1.56 (s, 3H), 2.04 (bs, 3H), 2.27 (m, 1H), 2.29 (s, 3H), 2.33 (m, 1H), 3.92 (d, 7.5 Hz, 1H), 4.19 (d, J=8.5 Hz, 1H), 4.3 (d, J=8.5 Hz, 1H), 4.51 (dd, J=10.6, 6.7 Hz, 1H), 4.87 (bm, 1H), 4.95 (dd, J=9.4, 1.7 Hz, 1H), 5.60 (d, J=7.5, 1H), 5.61 (s, 1H), 7.48 (dd, J=7.8, 7.7 Hz, 2H), 7.6 (dd, J=7.8, 7.7 Hz, 1H)8.1 (d, J=7.8, 2H).

EXAMPLE 27

7,10—O—(1,1,3,3-tetramethyl-1,3-ethanediyl)-10-DAB

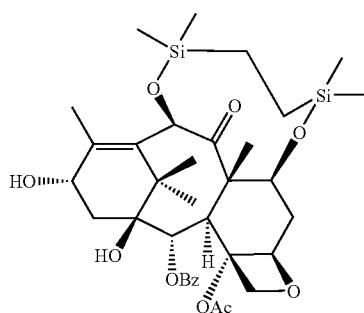

10-DAB (0.544 g, 1 mmol) was dissolved in THF at approximately 20 to 25 mL/g (10 mL) along with 2.5 eq of DMAP (0.3 g, 2.5 mmol). To this solution was added 1,2-bis (chlorodimethylsilyl)ethane (0.215 g, 1 mol) at ambient temperature until the conversion of the product was complete by TLC (3:1 ethyl acetate/heptane). The reaction mixture then was diluted with heptane (20 mL) to precipitate out the DMAP-HCl salt and filtered through silica gel (10 g). The filter cake was washed with a 1:1 mixture of ethyl acetate and heptane (20 mL) to ensure complete product recovery. The filtrate was stabilized with triethylamine (0.5 mL) and concentrated until crystals formed. The mixture was chilled to 0° C. for 30 min and the white solid was collected via a Buchner funnel and washed with ice-cold 20% ethyl acetate in heptane (10 mL). The filter cake was dried under vacuum (0.1 mmHg) at 50° C. to constant weight of 0.58 g (85% yield). Mp: 191 to 193° C., $^1$H NMR (400 MHz, CDCl$_3$) δ (ppm): 0.05 (s, 3H), 0.9 (s, 3H), 0.17 (s, 3H), 0.33 (s, 3H), 0.43 (m, 1H), 0.57 (dd, J=11.8, 5.6 Hz, 2H), 0.78 (m, 1H), 1.05 (s, 3H), 1.10 (s, 3H), 1.54 (s, 1H), 1.69 (s, 3H), 1.87 (m, J=14.1, 12.6, 4.2, 1.9 Hz, 1H), 2.06 (d, J=1.2 Hx, 3H), 2.11 (d, J=5.0 Hz, 1H), 2.26 (m, 1H), 2.27, (s, 3H), 2.32 (m, 1H), 3.92 (d, J=6.8 Hz, 1H), 4.15 (d, J=8.5), 4.28 (d, J=8.5 Hz, 1H), 4.31 (dd, J=10.1, 6.5 Hz, 1H), 4.84 (m, 15.2, 5.4, 7.7 Hz), 4.92 (dd, J=9.7, 2.0 Hz, 1H), 5.46 (s, 1H), 5.57 (d, J=7.3, 1H), 7.48 (dd, J=7.8, 7.7 Hz, 2H), 7.6 (dd, J=7.8, 7.7 Hz, 1H)8.1 (d, J=7.8, 2H).

EXAMPLE 28

7,10—O—(1,1,3,3,5,5-hexamethyl-1,3,5-trisiloxanediyl)-10-DAB

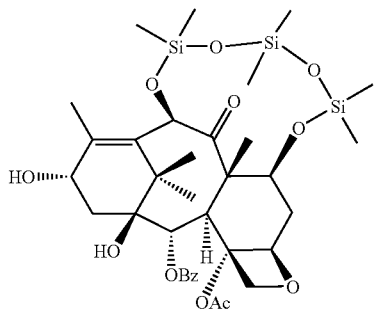

10-DAB (0.544 g, 1 mmol) was dissolved in THF at approximately 20 to 25 mL/g (10 mL) along with 2.5 eq of DMAP (0.3 g, 2.5 mmol). To this solution was added 1,5-dichlorohexamethyltrisiloxane (0.277 g, 1 mol) at ambient temperature until the conversion the product was complete by TLC (3:1 ethyl acetate/heptane). The reaction mixture then was diluted with heptane (20 mL) to precipitate out the DMAP-HCl salt and filtered through silica gel (10 g). The filter cake was washed with a 1:1 mixture of ethyl acetate and heptane (20 mL) to ensure complete product recovery. The filtrate was stabilized with triethylamine (0.5 mL) and concentrated until crystals formed. The mixture was chilled to 0° C. for 30 min and the white solid was collected via a Buchner funnel and washed with ice-cold 20% ethyl acetate in heptane (10 mL). The filter cake was dried under vacuum (0.1 mmHg) at 50° C. to constant weight of 0.65 g (87% yield). Mp: 240 to 242° C., $^1$H NMR (400 MHz, CDCl$_3$) δ (ppm): 0.06 (s, 6H), 0.09 (1, 3H), 0.15 (s, 3H), 0.16 (s, 3H), 0.29 (s, 3H), 1.05 (s, 3H), 1.19 (s, 3H), 1.56 (s, 1H), 1.70 (s, 3H), 1.89 (m, 1H), 1.96 (d, J=5.3 Hz, 1H), 2.10 (d, J=1.0 Hz, 3H), 2.27 (m, 1H), 2.29 (s, 3H), 2.42 (m, 1H), 3.96 (d, J=7.1 Hz, 1H), 4.17 (d, J=8.1 Hz, 1H), 4.29 (d, J=8.1 Hz, 1H), 4.49 (dd, J=10.0, 6.9 Hz, 1H), 4.85 (m, 1H), 4.94 (dd, J=9.6, 1.9 Hz, 1H), 5.63 (s, 1H), 5.64 (d, 6.75 Hz, 1H), 7.47 (dd, J=7.8, 7.7 Hz, 2H), 7.59 (dd, J=7.8, 7.7 Hz, 1H)8.11 (d, J=7.8, 2H).

EXAMPLE 29

Docetaxel

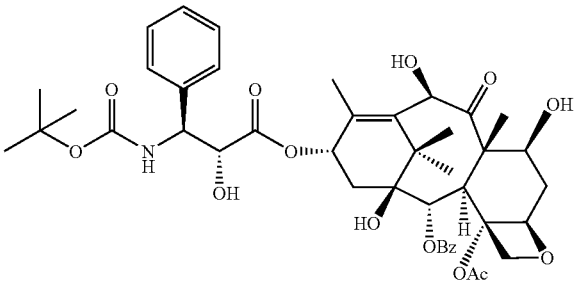

Starting with 10-DAB, the C(7) and C(10) hydroxy groups were protected using 1,3-dichlorotetramethyldisiloxane (i.e., the bridging silicon-based protecting group of Formula (4)

wherein $G_1$, $G_2$, $G_3$, and $G_4$ are methyl, $L_1$ and $L_2$ are chloro, Z is —O—); cyclic intermediate (29) wherein $G_1$, $G_2$, $G_3$, and $G_4$ are methyl, Z is —O—) resulted in 95% yield after recrystallization from ethyl acetate and heptane. The coupling of intermediate (29) and β-lactam side chain precursor (36) wherein $P_2$ is MOP was carried out under kinetic resolution using LHMDS and 3 equivalents of the racemic (36); intermediate (410) wherein $G_1$, $G_2$, $G_3$, and $G_4$ are methyl, $P_2$ is MOP, Z is —O—) resulted in 90% yield after recrystallization from dichloromethane and heptane. Simple dilute hydrochloric acid deprotection gave docetaxel in 75% yield after recrystallization from isopropanol and heptane.

EXAMPLE 30

2'-(2-methoxy-2-propoxy)-7,10—O—(1,1,3,3-tetramethyl-1,3-disiloxanediyl)-docetaxel

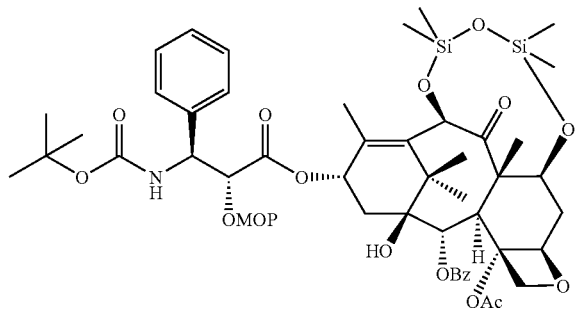

7,10—O—(1,1,3,3-tetramethyl-1,3-disiloxanediyl)-10-DAB (0.67 g, 0.99 mmol) and cis-N-t-butoxy-3-(2-methoxy-2-propoxy)-4-phenyl-azetidin-2-one (1.0 g, 3 eq) was dissolved in anhydrous THF (5 mL) under nitrogen then cooled to −45° C. LHMDS (1.2 mL, 1.1 eq) 1.0 M in THF was added drop-wise to control the exotherm. The reaction was allowed to proceed at ≦−35° C. for 2 to 5 h. The reaction was quenched with a solution of acetic acid (1.2 eq) in ethyl acetate (25 mL), washed with sodium bicarbonate (5 mL) and brine (5 mL), dried over sodium sulfate (7 g), filtered through silica (7 g), and concentrated. The residue was taken up in a minimal amount of dichloromethane (1 mL) containing 1% triethylamine and added to heptane (15 mL) to triturate out the excess β-lactam. The product (0.88 g, 88%) as a single diastereomer was collected by Buchner funnel and washed with heptane. Mp: 235 to 238° C., $^1$H NMR (MHz, $CDCl_3$) δ (ppm): 0.07 (s, 3H), 0.08 (s, 3H), 0.12 (s, 3H), 0.41 (s, 3H), 1.08 (s, 3H), 1.12 (s, 3H), 1.25 (s, 3H), 1.30 (s, 3H), 1.32 (s, 9H), 1.53 (s, 1H), 1.67 (s, 3H), 1.90 (bs, 3H), 1.92 (m, 1H), 2.07 (m, 1H), 2.30 (m, 2H), 2.50 (s, 3H), 2.66 (bs, 3H), 3.84 (d, J=6.9 Hz, 1H), 4.22 (d, J=8.7 Hz, 1H), 4.32 (d, J=8.7 Hz, 1H), 4.48 (dd, J=9.9, 6.4 Hz, 1H), 4.50 (d, J=3.3 Hz, 1H), 4.95 (m, J=8.6, 1H), 5.22 (bm, 1H), 5.49 (bm, 1H), 5.57 (s, 1H), 5.65 (d, J=6.9 Hz, 1H), 6.24 (bm, 1H), 7.24 (m, 1H), 7.30 (d, J=7.2, 2H), 7.37 (dd, J=7.2, 7.2, 2H), 7.51 (dd, J=8.0, 7.5 Hz, 2H), 7.60 (dd, J=8.0, 7.2 Hz, 1H), 8.11 (d, J=7.5 Hz, 2H). The flexible side chain proton chemical shifts exhibit drifting dependent on level of water in the $CDCl_3$ solvent.

EXAMPLE 31

Docetaxel

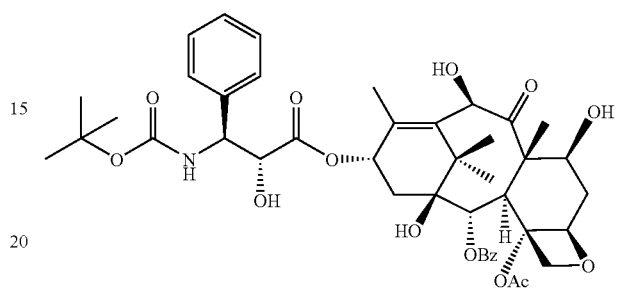

2'-(2-methoxy-2-propoxy)-7,10—O—(1,1,3,3-tetramethyl-1,3-disiloxanediyl)-docetaxel (38.38 g, 38.2 mmol) in acetonitrile (580 mL) then 0.2 M HCl (115 mL) was added and the mixture was stirred at ambient temperature (22° C. to 25° C.) for 2 to 3 h until complete conversion to the product ($R_f$=0.15) was observed via TLC (3:1 ethyl acetate:heptane). The product mixture then was diluted with ethyl acetate (580 mL) and washed with water (290 mL), brine (150 mL), saturated aqueous sodium bicarbonate (290 mL), brine (200 mL) and dried over sodium sulfate (60 g). The mixture was filtered through silica gel (30 g) and the filter cake was rinsed with ethyl acetate (350 mL). The combined filtrate was concentrated to approximately 192 mL followed by addition of heptane (550 mL) to induce crystallization. The mixture was further concentrated to remove approximately 200 mL of solvent. The mixture was cooled to ambient temperature, the crystals were collected via vacuum filtration through a Buchner funnel, and the crystals were dried to a constant weight of 30.57 g (99.3% yield) at 98.3% HPLC purity. mp: 186 to 188° C., EA: % C: theory 63.93, found 63.38, % H: theory 6.61, found 6.59. $^1$H NMR (400 MHz, $CDCl_3$) δ (ppm): 1.13 (s, 3H, H-17), 1.24 (s, 3H, H-16), 1.34 (s, 9H, H-t-Boc), 1.64 (s, 1H, HO-1), 1.76 (s, 3H, H-19), 1.85 (s, 3H, H-18), 1.79 to 1.88 (m, 1H, H-6), 2.27 (m, J=8.8 Hz, 2H, H-14), 2.38 (s, 3H, Ac-4), 2.60(m, 1H, H-6), 3.32 (bd, J=4.8 Hz, 1H, HO-2'), 3.92 (d, J=6.9 Hz, 1H, H-3), 4.18 (d, J=8.5 Hz, 1H, H-20), 4.19 (bs, 1H, HO-10), 4.23 (m, 1H, H-7), 4.32 (d, J=8.5 Hz, 1H, H-20), 4.62 (bm, 1H, H-2'), 4.94 (m, 1H, H-5), 5.20 (bd, J=1.7 Hz, H-10), 5.26 (bm, 1H, H-3'), 5.40 (bd, J=9.6 Hz, H-N), 5.68 (d, J=6.9 Hz, 1H, H-2), 6.22 (bm, 1H, H-13), 7.29 to 7.4 (m, 5H, H-Ph), 7.50 (dd, J=7.9, 7.6 Hz, 2H, H-mBz), 7.62 (dd, J=7.25, 7.6 Hz, 1H-pBz), 8.10 (d, J=7.9 Hz, 2H, H-oBz). Conformed to Literature References: (a) Journal of Labelled Compounds and Radiopharmaceuticals, 2004; 47:763-777; and (b) Tetrahedron, 1989, 45:13, pp 4177-4190.

EXAMPLE 32

2'-(trimethylsilyloxy)-7,10—O—(1,1,3,3-tetramethyl-1,3-disiloxanediyl)-docetaxel

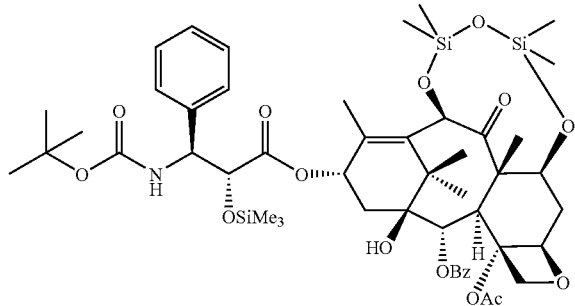

7,10—O—(1,1,3,3-tetramethyl-1,3-disiloxanediyl)-10-DAB (4.29 g, 6.4 mmol) and N-t-butoxycarbonyl-3-trimethylsilyloxy-4-phenyl azetidin-2-one (6.4 g, 19.1 mmol) were dissolved in anhydrous THF (43 mL) under nitrogen and then cooled to −45° C. LHMDS (1.2 mL, 1.1 eq, 1.0 M in THF) was added drop-wise to control the exotherm. The reaction was allowed to proceed at ≦−45° C. for 5 h. The reaction was quenched with a solution of acetic acid (1.2 eq) in ethyl acetate (50 mL), washed with sodium bicarbonate (10 mL) and brine (10 mL), dried over sodium sulfate (10 g), filtered through silica (10 g), and concentrated to give a solid. The solid was recrystallized from methanol to give 3.6 g (55%) of white powder as a single diastereomer after drying under vacuum (<1 mmHg) and ambient temperature. mp: 248 to 250° C., $^1$H NMR (400 MHz, CDCl$_3$) δ: −0.12 (s, 9H), 0.08 (s, 3H), 0.09 (s, 3H), 0.12 (s, 3H), 0.42 (s, 3H), 1.12 (s, 3H), 1.27 (s, 3H), 1.31 (s, 9H), 1.54 (s, 1H), 1.68 (s, 3H), 1.88 (s, 3H), 1.86 to 1.96 (m, 1H), 2.08 to 2.18 (m, 1H), 2.26 to 2.43 (m, 2H), 2.54 (s, 3H), 3.85 (d, J=7.2 Hz, 1H), 4.24 (d, J=8.5 Hz, 1H), 4.32 (d, J=8.5 Hz, 1H), 4.45 (bs, 1H), 4.50 (dd, J=6.8, 10.3 Hz, 1H), 4.96 (m, J=8.5 Hz, 1H), 5.29 (m, J=8.5 Hz, 1H), 5.52 (bm, J=8.5 Hz, 1H), 5.57 (s, 1H), 5.66 (d, J=7.5 Hz, 1H), 6.31 (bt, J=8.6 Hz, 1H), 7.3 to 7.41 (m, 5H), 7.48 (dd, J=6.9, 8.4 Hz, 2H,), 7.59 (dd, J=6.9, 7.5, 1H), 8.12 (d, J=7.5 Hz, 2H).

EXAMPLE 33

2'-(trimethylsilyloxy)-7,10—O—(1,1,3,3-tetramethyl-1,3-disiloxanediyl)-docetaxel To a solution of 7,10—O—(1,1,3,3-tetramethyl-1,3-disiloxanediyl)-10-DAB (0.84 g, 1.24 mmol) in THF (10 mL) at −45° C. under nitrogen was added 1.0 M butyllithium (0.93 mL) in hexanes. After 30 min at this temperature, a solution of (+)-N-t-butoxycarbonyl-3-trimethylsilyloxy-4-phenyl azetidin-2-one (0.5 g, 1.5 mmol) in THF (2 mL) was added and the mixture was stirred and warmed to 0° C. over 4 h. The reaction was quenched with triethylamine (1 eq) and acetic acid (1 eq), diluted with 25 mL of heptane, and filtered through silica gel (30 g). The filtrate was concentrated by rotary evaporation to give white crystals (0.69 g, 55%) $^1$HNMR of the crude product conformed to the structure of 2'-(trimethylsilyloxy)-7,10—O—(1,1,3,3-tetramethyl-1,3-disiloxanediyl)-docetaxel.

EXAMPLE 34

Deprotection of 2'-(trimethylsilyloxy)-7,10—O—(1,1,3,3-tetramethyl-1,3-disiloxanediyl)-docetaxel To a solution of 2'-(trimethylsilyloxy)-7,10—O—(1,1,3,3-tetramethyl-1,3-disiloxanediyl)-docetaxel (0.5 g, 0.495 mmol) in acetonitrile (2.5 mL) at ambient temperature was added a solution of 0.2 M HCl and the mixture was stirred at ambient temperature (22° C. to 25° C.) for 2 to 3 h until complete conversion to the product ($R_f$=0.15) was observed via TLC (3:1 ethyl acetate:heptane). The mixture then was diluted with ethyl acetate (5 mL) and washed with water (2 mL), brine (2 mL), saturated aqueous sodium bicarbonate (2 mL), brine (2 mL) and dried over sodium sulfate (6 g). The mixture was filtered through silica gel (5 g) and the filter cake was rinsed with ethyl acetate (5 mL). The combined filtrate was concentrated to approximately 1 mL and heptane (5 mL) was added to induce crystallization. The mixture then was concentrated to remove approximately 1-2 mL of solvent. The mixture was cooled to ambient temperature before the crystals were collected via vacuum filteration through a Buchner funnel and dried to a constant weight of 0.399 g (93% yield) of a crystalline product with HNMR spectra that conformed to Docetaxel.

In order of maximize the recovery of Docetaxel it was discovered that purification of the intermediate 2'-(trimethylsilyloxy)-7,10—(1,1,3,3-tetramethyl-1,3-disiloxanediyl)-docetaxel was unnecessary when optically pure (+)-N-t-butoxycarbonyl-3-trimethylsilyloxy-4-phenyl azetidin-2-one was used.

EXAMPLE 35

Docetaxel

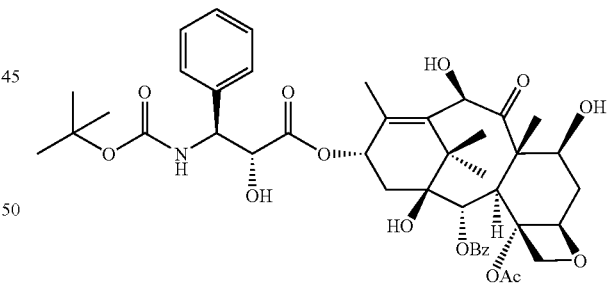

To an oven dried 25 mL round bottom flask (RBF) under nitrogen equipped with magnetic stirring was added diisopropylamine (0.83 mL, 5.86 mmol) and THF (1.5 mL). The mixture was cooled to −45° C. and a solution of n-hexyl lithium (2.33 mL, 2.30 M, 5.37 mmol) was added drop-wise to control the exotherm and maintain the reactor temperature at <−40° C. After the addition was completed, the cooling bath temperature was raised to 0-5° C. before use.

Coupling Reaction: To an oven dried 250 mL RBF under nitrogen equipped with magnetic stirring was added 7,10—O—(1,1,3,3-tetramethyl-1,3-disiloxanediyl)-10-DAB (3.29 g, 4.88 mmol), and THF (30 mL). The mixture was cooled to −45° C. The already prepared LDA was added to the reaction mixture via syringe in a period of 5 minutes and stirred at that temperature for 45 minutes. To this mixture was then added (+)-N-t-butoxycarbonyl-3-trimethylsilyloxy-4-phenyl azetidin-2-one (1.80 g (5.37 mmol) in THF (8 mL)). The reaction mixture was warmed up to −15° C. and stirred for one hour at −15 to −10° C. TLC monitoring of the reaction after one hour (1:3 ethyl acetate heptane) showed complete conversion to 2'-(trimethylsilyloxy)-7,10—O—(1,1,3,3-tetramethyl-1,3-disiloxanediyl)-docetaxel.

Work-Up: To the reaction flask at reaction temperature was added 1 mL of saturated sodium bicarbonate and stirred for 5 minutes. It was then diluted by ethyl acetate (50 mL) and washed with 50 mL of brine. The organic layer was separated and dried over MgSO$_4$ and concentrated to give 5.10 g of crude 2'-(trimethylsilyloxy)-7,10—(1,1,3,3-tetramethyl-1,3-disiloxanediyl)-docetaxel that was used directly for deprotection. The above crude mixture was dissolved in acetonitrile (50 mL) and 0.2 N HCl (25 mL) was added and stirred at room temperature for four hours. TLC monitoring (3:1/EtOAc:heptane) showed the completion of the reaction. The reaction mixture was diluted by ethyl acetate (100 mL) and washed twice with distilled water (50 mL), saturated sodium bicarbonate (50 mL) and brine (50 mL). The resulting organic layer was dried over MgSO$_4$ and concentrated to give 3.76 g (95.3% yield) of Docetaxel with 96.5% HPLC purity with the major impurity as undesilylated (1.6%) intermediate at the C(7)-hydroxy group.

EXAMPLE 36

Paclitaxel

Starting with 10-DAB, the C(7) and C(10) hydroxy groups were protected using 1,3-dichlorotetramethyldisiloxane (i.e., the bridging silicon-based protecting group of Formula (4), wherein $G_1, G_2, G_3$, and $G_4$ are methyl, $L_1$ and $L_2$ are chloro, Z is —O—); cyclic intermediate (29) wherein $G_1, G_2, G_3$, and $G_4$ are methyl, Z is —O—) resulted in 95% yield after recrystallization from ethyl acetate and heptane. Intermediate (29) was treated with (+)-N-benzoyl-4-phenyl-3-(2-methoxy-2-propoxy)-azetidin-2-one (i.e., β-lactam (16) wherein P$_2$ is MOP) (1.1 equivalents) in the presence of LHMDS (1.1 equivalents) at −45° C. to −10° C. for 3 hours to produce compound (210) wherein $G_1, G_2, G_3$, and $G_4$ are methyl, Z is —O—, and P$_2$ is MOP). Compound (210) was crystallized from ethyl acetate (85% yield, 98% pure). Compound (210) was treated with methanol and a catalytic amount of NaHCO$_3$ at room temperature for 20 hours to yield compound (211) wherein P$_2$ is MOP, which is subsequently crystallized from a mixture of isopropyl alcohol and heptane (75-80% yield, 97% pure). Compound (211) was treated with acetyl chloride (1.05 equivalents) and LHMDS (1.1 equivalents) at −45° C. for 30 minutes to yield a crude mixture that is 96% pure. Upon crystallization from isopropanol, a C(10)-acetylated compound was produced in 85-90% yield and 97% pure. The compound was then treated with 0.2 M HCl in acetonitrile at room temperature for 2 hours to produce paclitaxel that was crystallized from methanol.

EXAMPLE 37

Preparation of Paclitaxel

Starting with 10-DAB (23), the C(7) and C(10) hydroxy groups were protected using 1,3-dichlorotetramethyldisiloxane (i.e., the bridging silicon-based protecting group of Formula (4), wherein $G_1, G_2, G_3$, and $G_4$ are methyl, $L_1$ and $L_2$ are chloro, Z is —O—); cyclic intermediate (29) wherein $G_1, G_2, G_3$, and $G_4$ are methyl, Z is —O—) resulted in 95% yield after recrystallization from ethyl acetate and heptane. Intermediate (29) was treated with methanol and a catalytic amount of Na$_2$CO$_3$ at room temperature for 20 minutes to produce compound (212) wherein $R_{10,4}, G_1, G_2, G_3$ and $G_4$ are methyl, Z is —O—). Compound (212) was crystallized from ethyl acetate (75% yield, 97% pure). Compound (212) was then treated with acetyl chloride (1.02 equivalents) and LHMDS (1.1 equivalents) for 30 minutes. Without isolation of the intermediate, the 10-acetyl derivative (220) wherein $R_{10,4}, G_1, G_2, G_3$ and $G_4$ are methyl, Z is —O—) was treated with (+)-N-benzoyl-4-phenyl-3-(2-methyoxy-2-propoxy)-azetidin-2-one (i.e., β-lactam (16) wherein P$_2$ is MOP) (1.1 equivalents) in the presence of LHMDS (1.1 equivalents) at −45 to −10° C. for 3 hours to produce compound (221) wherein $G_1, G_2, G_3$ and $G_4$ are methyl, Z is —O—, and P$_2$ is MOP) in 85% yield and 94% purity. Compound (221) was then treated with 0.2 M HCl in acetonitrile at room temperature for 2 hours to produce paclitaxel that was crystallized from ethyl acetate and heptane.

EXAMPLE 38

2'-(2-methoxy-2-propoxy)-7,10—O—(1,1,3,3-tetramethyl-1,3-disiloxanediyl)-paclitaxel

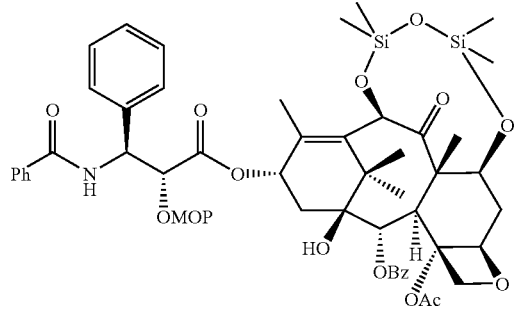

To a THF (200 mL) solution of 7,10—O—(1,1,3,3-tetramethyl-1,3-disiloxanediyl)-10-DAB (12.1 g, 17.93 mmol) and (+)-cis-N-benzoyl-3-(2-methoxy-2-propoxy)-4-phenyl-azetidin-2-one (6.69 g, 19.7 mmol) under nitrogen and magnetic stirring at −45° C. was added a 1.0 M THF solution of LHMDS (19.7 mL, 19.7 mmol) over 15 minutes. The temperature of the reaction was warmed to −10° C. and stirred at this temperature until TLC analysis (1:1 ethyl acetate:hexane) showed complete disappearance of 7,10—O—(1,1,3,3-tetramethyl-1,3-disiloxanediyl)-10-DAB. The reaction mixture was quenched with acetic acid (1.182 g, 19.7 mmol), diluted with ethyl acetate (200 mL), and warmed to ambient temperature. The mixture was washed with brine and dried over sodium sulfate. The drying agent was removed by vacuum filtration and the filtrate was concentrated to give a solid. The solid was dissolved in hot ethyl acetate (450 mL) and reduced to half volume under rotary evaporation at 25 to 30° C. to induce crystal formation then cooled in a 0° C. bath for 1 h. The white crystals were collected by vacuum filtration, washed with cold 1:1 ethyl acetate:hexanes solution, and dried to a constant weight of 15.2 g (84% yield). $^1$H NMR (400 MHz, CDCl$_3$) δ (ppm): 0.07 (s, 3H), 0.08 (s, 3H), 0.12 9 (s, 3H), 0.42 (s, 3H), 1.11(s, 3H), 1.13 (s, 3H), 1.23 (s, 3H), 1.34 (s, 3H), 1.61 (s, 1H), 1.68 (s, 3H), 1.91 (d, J=1.10 Hz), 1.92 (m, 1H), 2.07 (dd, 15.1, 8.92 Hz. 1H), 2.24 to 2.36 (m, 2H), 2.53 (s, 3H), 2.78 (s, 3H), 3.84 9d, J=7.0 Hz), 4.25 (d, J=8.75 Hz, 1H), 4.23 (d, J=8.75 Hz), 4.49 (dd, J=10.48, 6.72 Hz, 1H), 4.65 (d, J=3.23 Hz), 1H), 4.95 (dd, J=9.56, 2.47 Hz, 1H), 5.56 (s, 1H), 5.62 (dd, J=8.01, 3.08 Hz, 1H), 5.66 (d, J=7.23 Hz, 1H), 6.24 (t, J=8.60, 1H), 7.18 (d, J=8.03 Hz), 7.24 to 7.54 (m, 10H), 7.60 (m, 1H), 7.78 (d, J=7.88 Hz, 2H), 8.12 m, 2H).

EXAMPLE 39

2'-(2-methoxy-2-propoxy)-7—O—(1-methoxy-1,1,3,3-tetramethyl-1,3-disiloxanyl)-10-hydroxy paclitaxel

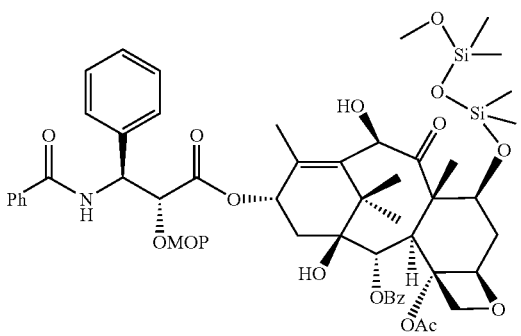

Sodium Bicarbonate Methanolysis: To a solution of 2'-(2-methoxy-2-propoxy)-7,10—O—(1,1,3,3-tetramethyl-1,3-disiloxanediyl)-paclitaxel (5.0 g, 4.93 mmol) in anhydrous methanol (250 mL) was added sodium bicarbonate (0.5 g, 5.95 mmol) and the mixture was stirred at ambient temperature (22 to 25° C.) under nitrogen for 2 days; TLC analysis (30:70 ethyl acetate:hexanes) indicated that conversion to a more polar product was complete. Triethylamine (2 g, 19.7 mmol) and acetic acid (0.4 g, 6.7 mmol) was added and the methanol was removed under reduced pressure rotary evaporation to give a solid residue. The solid was taken up in isopropanol (75 mL) followed by heptane (75 mL) addition. The mixture then was concentrated to approximately half volume under reduced pressure rotary evaporation to induce crystal formation at 40° C. The mixture was cooled to ambient temperature (20 to 22° C.) and the crystals (3.6 g, 70% yield) were harvested.

Triethylamine-Methanolysis: To a solution of 2'-(2-methoxy-2-propoxy)-7,10—O—(1,1,3,3-tetramethyl-1,3-disiloxanediyl)-paclitaxel (100 mg, 0.1 mmol) in anhydrous methanol (5 mL) under nitrogen was added triethylamine (0.014 mL) and the mixture stirred for 12 h at ambient temperature (22 to 25° C.) until TLC (30:70 ethyl acetate:hexane) analysis showed complete conversion to the lower $R_f$ product. Heptane (5 mL) was added and the mixture was concentrated under reduced pressure evaporation at 40° C. to approximately half-volume to induce crystal formation. Cooling the mixture to ambient temperature (22 to 25° C.) and 90 mg (88% yield) of the crystals were harvested. $^1$H NMR (400 MHz, CDCl$_3$) δ (ppm): 0.083 (s, 3H), 0.088 (s, 3H), 0.11 (s, 3H), 0.12 (s, 3H), 1.11 (s, 3H), 1.12 (s, 3H), 1.22 (s, 3H), 1.34 (s, 3H), 1.70 (s, 1H), 1.76 (s, 3H), 1.96 (d, J=1.10 Hz), 1.98 (m, 1H), 2.07 (dd, J=14.68, 8.66, 1H), 2.29 (dd, J=15.05, 9.41, 1H), 2.49 (m, 1H), 2.52 (s, 3H), 2.79 (m, 3H), 3.47 (s, 3H), 3.91 (d, J=7.52, 1H), 4.23 (d, J=8.97, 1H), 4.27 (d, J=1.95 Hz, 1H), 4.33 (d, J=8.97, 1H), 4.47 (dd, J=10.51, 6.6 Hz, 1H), 4.65 (d, J=3.13 Hz, 1H), 4.95 (dd, J=9.8, 1.75 Hz, 1H), 5.13 (d, J=1.95 Hz, 1H), 5.60 (dd, J=7.99, 3.19 Hz, 1H), 5.68 (d, J=7.19 Hz, 1H), 6.25 (t, J=9.27 Hz, 1H), 7.18 (d, J=8.03 Hz), 7.24 to 7.54 (m, 10H), 7.60 (m, 1H), 7.78 (d, J=7.88 Hz, 2H), 8.12 m, 2H).

EXAMPLE 40

7—O—(1-methoxy-1,1,3,3-tetramethyl-1,3-disiloxanyl)-10-DAB

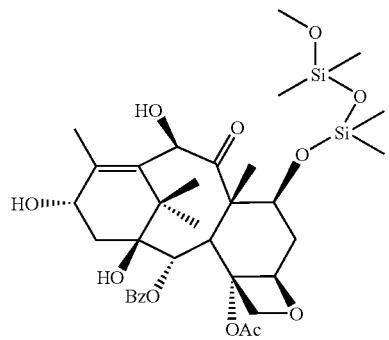

Triethylamine-methanolysis: To 1 g (1.48 mmol) of 7,10—O—(1,1,3,3-tetramethyl-1,3-disiloxanediyl)-10-DAB was added 20 mL of anhydrous methanol. The solution was allowed to stir until homogeneous (about 10 minutes). The flask was charged with 1 equivalent of triethylamine (TEA, 1.48 mmol, 206 mL) and allowed to stir for approximately 23 hours. Reaction completion was monitored with TLC (1:1 ethyl acetate:hexanes). Upon completion, the solution was diluted with about 15 mL heptane and evaporated until all the methanol was removed. Crystals formed on evaporation and were allowed to stir for 2 hours. Crystals were filtered and washed with heptane to yield 948 mg (90.6% yield) of a white solid. $^1$H NMR (400 MHz, CDCl$_3$) δ (ppm): 0.085 (s, 3H), 0.099 (s, 3H), 0.120 (s, 3H), 0.0123 (s, 3H), 1.09 (overlap, 2-s (6H), 1.75 (s, 3H), 1.93 (m, 1H), 1.97 (d, J=5.07 Hz, 1H), 2.09 (d, J=1.22 Hz, 3H), 2.27 (m, 1H), 2.28 (s, 3H), 2.55 (m, 1H), 3.48 (s, 3H), 3.98 (d, J=6.86 Hz, 1H), 4.18 (d, J=8.14 Hz, 1H), 4.25 (d, J=2.03 Hz, 1H), 4.31 (d, J=8.14 Hz, 1H), 4.49 (dd, J=10.91, 6.71 Hz, 1H), 4.88 (dd, 17.60, 7.48 Hz, 1H), 4.95 (dd, J=9.49, 1.79 Hz, 1H), 5.18 (d, J=2.03, 1H), 5.62 (d, J=6.94 Hz, 1H), 7.48(t, J=7.7-Hz, 2H), 7.60 (m, J=7.7 Hz, 1H), 8.11 (m, 2H).

EXAMPLE 41

2'-(2-methoxy-2-propoxy)-7—O—(1-methoxy-1,1,3,3-tetramethyl-1,3-disiloxanyl)-paclitaxel

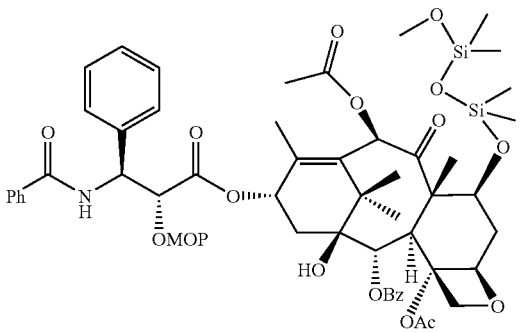

To a solution of 2'-(2-methoxy-2-propoxy)-7—O—(1-methoxy-1,1,3,3-tetramethyl-1,3-disiloxy)-10-hydroxy paclitaxel (2.62 g, 2.5 mmol) in anhydrous THF (22 mL) at −45° C. under magnetic stirring and nitrogen was added a THF 1.0 M solution of LHMDS (2.9 mL, 2.9 mmol) followed by acetyl chloride (0.275 mL, 2.88 mmol). The mixture was stirred at −45° C. for 1 h when TLC analysis (30:70 ethyl acetate:hexanes) indicated conversion to a less polar product ($R_f$=0.5). The reaction was quenched with acetic acid (0.173 g, 2.88 mmol), diluted with ethyl acetate (50 mL), washed with brine, and dried over sodium sulfate. Removal the drying agent and concentration of the filtrate gave 2.6 g of a solid (95% HPLC purity).

One-pot C(10)-Hydroxy Acetylation and C(13) Side Chain Coupling: To a solution of 7—O—(1-methoxy-1,1,3,3-tetramethyl-1,3-disiloxy)-10-DAB (3.24 g, 4.58 mmol) in anhydrous THF (40 mL) at −45° C. under magnetic stirring and nitrogen was added 5 mL of a 1.0 M solution of LHMDS in THF (5 mmol) followed by acetyl chloride (AcCl, 0.335 mL, 4.7 mmol). The reaction progress was monitored via $^1$HNMR analysis for the disappearance of the C(10)-carbinol resonance at 5.18 ppm in CDCl$_3$ after 15 min. Once the acetylation was shown to be complete, a second equivalent of the 1.0 M solution of LHMDS in THF (5 mL, 5 mmol) was added followed by solid (+)-cis-N-benzoyl-3-(2-methoxy-2-propoxy)-4-phenyl-azetidin-2-one. The temperature was raised to −10° C. and the conversion to the less polar product 2'-(2-methoxy-2-propoxy)-7—O—(1-methoxy-1,1,3,3-tetramethyl-1,3-disiloxy)-paclitaxel was monitored via TLC (30:70 ethyl acetate:hexanes). After 3 h, the reaction mixture was quenched with acetic acid (0.3 g, 5 mmol) and diluted with ethyl acetate (200 mL) and warmed to ambient temperature. The mixture was washed with brine and dried over sodium sulfate. The drying agent was removed by vacuum filtration and the filtrate was concentrated to give a solid residue. Trituration of the residue with heptane (100 mL) gave 4.2 g of the product (94% HPLC purity). $^1$H NMR (400 MHz, CDCl$_3$) δ (ppm): 0.059 (s, 3H), 0.092 (s, 6H), 0.20 (s, 3H), 1.13 (s, 3H), 1.20 (s, 3H), 1.22 (s, 3H), 1.33 (s, 3H), 1.71 (s, 3H), 1.96 (m, 1H), 1.98 (d, J=1.0), 2.10 (dd, J=15.74, 9.18 Hz, 1H), 2.17 (s, 3H), 2.31 (dd, J=15.57, 9.36 Hz, 1H), 2.53 (s, 3H), 2.58 (m, 1H), 2.78 (s, 3H), 3.46 (s, 3H), 3.88 (d, J=7.06 Hz, 1H), 4.21 (d, J=8.53, 1H), 4.32 (d, J=8.53, 1H), 4.54 (dd, J=10.23, 6.62 Hz, 1H), 4.66 (d, J=3.19 Hz, 1H), 4.96 (bd, J=9.80 Hz, 1H), 5.31 (bs, 1H), 5.62 (dd, J=8.28, 3.20 Hz, 1H), 5.71 (d, J=6.99 Hz, 1H), 6.20 (bt, J=9.03 Hz, 1H), 6.41 (s, 1H), 7.17 (d, J=8.12 Hz, 1H), 7.24 to 7.54 (m, 10H), 7.60 (m, 1H), 7.78 (d, J=7.88 Hz, 2H), 8.12 m, 2H).

EXAMPLE 42

Paclitaxel

To a solution of 2'-(2-methoxy-2-propoxy)-7—O—(1-methoxy-1,1,3,3-tetramethyl-1,3-disiloxanyl)-paclitaxel (1.6g, 97% purity, 1.47 mmol) in acetonitrile (12 mL) at ambient temperature (22 to 25° C.) under magnetic stirring and nitrogen was added a 0.2 M solution of HCl (3 mL, 0.6 mmol). After 3 h, TLC monitoring (3:1 ethyl acetate:hexanes) indicated complete conversion to desired product Paclitaxel. The mixture was quenched with triethylamine (0.121 g, 1.2 mmol) and the solvent was removed under rotary evaporation. The residue was taken up in ethyl acetate (20 mL), washed with saturated aqueous sodium bicarbonate and brine, and dried over sodium sulfate. The drying agent was filtered off and the filtrate concentrated and solvent exchanged with heptane (20 mL) to give a white powder. The powder was collected via vacuum filtration, washed with heptane, and dried to a constant weight of 1.2 g (1.40 mmol, 95% yield at 97% purity). $^1$H NMR (400 MHz, CDCl$_3$) δ (ppm): 1.14 (s, 3H), 1.24 (s, 3H), 1.68 (s, 3H), 1.79 (d, J=0.9 Hz, 3H), 1.88 (m, 1H), 2.23 (s, 3H), 2.28 (m, 1H), 2.35 (m, 1H), 2.38 (s, 3H), 2.48 (d, J=3.31, 1H), 2.54 (m, 1H), 2.79 (d, J=7.13 Hz, 1H), 4.19 (d, J=8.53, 1H), 4.30 (d, J=8.53 Hz, 1H), 4.40 (m, 1H), 4.78 (dd, J=5.29, 2.65 Hz, 1H), 4.94 (dd, J=9.45, 2.3 Hz, 1H), 5.16 (bs, 1H), 5.67 (d, J=7.02 Hz, 1H), 5.78 (dd, J=8.78, 2.50 Hz, 1H), 6.22 (bt, J=9.0 Hz, 1H), 6.26 (s, 3H), 6.97 (d, J=8.68, 1H), 7.32 to 7.53 (m, 10H), 7.61 (m, 1H), 7.73 (m, 2H), 8.12 (m, 2H).

EXAMPLE 43

2'-(benzoyloxy)-7,10—O—(1,1,3,3-tetramethyl-1,3-disiloxanediyl)-docetaxel

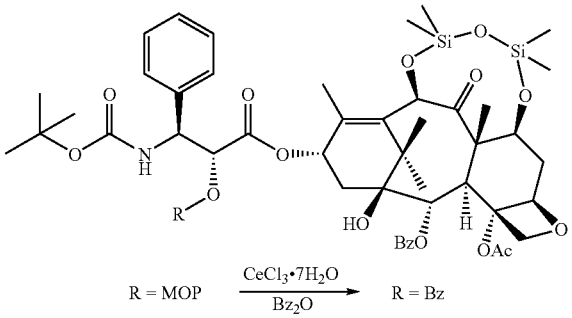

To a solution of 2'-(2-methoxy-2-propoxy)-7,10—O—(1,1,3,3-tetramethyl-1,3-disiloxanediyl)-docetaxel (5.0 g, 4.95 mmol) in anhydrous THF (25 mL) under nitrogen and magnetic stirring was added cerium trichloride heptahydrate (CeCl$_3$.7H$_2$O, 0.274 g, 0.735 mmol). The mixture was stirred at ambient temperature (22 to 25° C.) for 30 min when TLC (40:60 Ethyl acetate:hexanes) analysis showed complete loss of the 2-methoxy-2-propyl (MOP) protecting group to give a more polar intermediate ($R_f$=0.4) relative to the starting material ($R_f$=0.5). To the reaction mixture was added benzoic anhydride (1.6 g, 7.4 mmol); it was allowed to stir at ambient temperature over 12 h when TLC (40:60 Ethyl acetate:hexanes) analysis showed complete conversion to the less polar product ($R_f$=0.6). The mixture was diluted with ethyl acetate (100 mL), washed twice with saturated sodium bicarbonate (2×50 mL), then brine (25 mL), dried over sodium sulfate, filtered, and concentrated by rotary evaporation to give a residue. The residue was further purified by flash silica gel column chromatography (1:2 ethyl acetate:hexanes) to remove the unreacted benzoic anhydride. Pulling and concentration of the clean fractions gave the desired product (4.91 g, 95% yield).

7,10—O—(1,1,3,3-tetramethyl-1,3-disiloxanediyl)-10-DAB (1.66 g, 2.47 mmol) was taken up in 35 mL of anhydrous THF and stirred until homogeneous. The solution was cooled to −45° C. in an acetonitrile/dry ice bath. The solution was then deprotonated with 2.72 mL of LHMDS (1M in THF, 1.1 equivalents) and stirred for approximately 15 minutes. (+)-Cis-N-t-butoxycarbonyl-3-benzoyloxy-4-phenyl-azetidin-2-one (1.0 g, 2.72 mmol) was added as a solid to the mixture and stirred for 5 hours. The temperature was allowed to warm to −30° C. over the course of the 5 hours. After about 3.5 hours, more β-lactam (10%, 100 mg) was added along with more LHMDS (10%, 272 microliters) to push the reaction to completion. The reaction stopped with about 5% unreacted 7,10-protected 10-DAB remaining. The reaction was quenched with 1.2 eq of acetic acid (169 microliters) and 1.5 eq Triethylamine (515 microliters) that was premixed in 10 mL of THF. The organic layer was diluted with about 30 mL of ethyl acetate and washed twice with 15 mL of brine. The solvent was removed on a rotary evaporator and 2.9 g of a crude foam were retrieved. A flash column was employed to clean the product using a solvent system of 1:1 ethyl acetate/hexanes. 2.11 g (82.1% yield) of clean product were recovered. $^1$H NMR (400 MHz, CDCl$_3$) δ (ppm): 0.073 (s, 3H), 0.085 (s, 3H), 0.13 (s, 3H), 0.41 (s, 3H), 1.11 (s, 3H), 1.23 (s, 3H), 1.35 (s, 9H), 1.66 (s, 3H), 1.91 (m, 1H), 1.97 (s, 3H), 2.08 (m, 1H), 2.29 (m, 2H), 2.44 (s, 3H), 3.84 (d, J=6.93, 1H), 4.21 (d, J=8.53, 1H), 4.30 (d, J=8.53), 4.50 (dd, J=10.58, 6.58 Hz, 1H), 4.95 (dd, J=9.78, 2.38 Hz, 1H), 5.43 (bd, J=9.26 Hz, 1H), 5.49 (bd, J=3.09 Hz, 1H), 5.57 (bs, 1H), 5.59 (s, 1H), 5.65 (d, J=7.22 Hz, 1H), 6.27 (bt, J=8.97 Hz, 1H), 7.28 (m, 1H), 7.35 to 7.54 (m, 8H), 7.60 (m, 2H), 7.99 (d, J=7.68 Hz, 2H), 8.10 (d, 7.68, 2H).

(+)-Cis-N-t-butoxycarbonyl-3-benzoyloxy-4-phenyl-azetidin-2-one was obtained by reaction of (+)-cis-3-hydroxy-4-phenyl-azetidin-2-one with benzoic anhydride and t-butoxycarbonyl anhydride and isolated as a crystalline solid. $^1$H NMR (400 MHz, CDCl$_3$) δ (ppm): 1.44 (s, 9H), 5.37 (d, J=5.42 Hz, 1H), 6.18 (s, J=5.42 Hz, 1H), 7.18 to 7.34 (m, 7H), 7.49 (bt, 1H), 7.66 (bd, 2H).

EXAMPLE 44

2'-benzoyloxy docetaxel

It was found that benzoylation of Docetaxel was selective at the C(2') hydroxy position under benzoyl chloride-pyridine conditions. To a solution of Docetaxel (1.62 g, 2 mmol) in pyridine (10 mL) was added benzoyl chloride (0.394 g, 2.8 mmol) and the mixture was stirred and kept at <−25° C. over a 12 h period. TLC analysis (75:25 ethyl acetate:hexanes) showed approximately 80% conversion to a less polar major product (R$_f$=0.5) relative to the starting material (R$_f$=0.3). The mixture was quenched with saturated aqueous sodium bicarbonate, extracted with ethyl acetate (50 mL), washed with brine, dried over sodium sulfate, filtered, and concentrated to give a residue. Purification by silica gel flash column chromatography to remove the starting material eluting with 60:40 ethyl acetate:hexanes and collecting the clean fraction gave 1.28 g (71%) of 2'-benzoyloxy-Docetaxel after concentration and drying.

To a solution of 2'-(benzoyloxy)-7,10—O—(1,1,3,3-tetramethyl-1,3-disiloxanediyl)-docetaxel (1.0 g, 0.95 mmol) in acetonitrile (3 mL) at ambient 22 to 25° C. temperature was added a 0.2 M solution of HCl (2 mL, 0.2 mmol). After stirring for 2 h, TLC analysis (1:1 ethyl acetate:hexanes) indicated that complete conversion to the more polar product (R$_f$=0.15) relative to the starting material (R$_f$=0.45) was achieved. The reaction was quenched with triethylamine (0.5 g, 0.49 mmol) and concentrated to remove the acetonitrile solvent. The residue was taken up in ethyl acetate (20 mL), washed with saturated sodium bicarbonate, brine, dried with sodium sulfate, and filtered; the filtrate was concentrated and solvent exchanged with heptane to give 0.78 g (90% yield) of the product. $^1$H NMR (400 MHz, CDCl$_3$) δ (ppm): 1.12 (s, 3H), 1.22 (s, 3H), 1.35 (s, 9H), 1.75 (s, 3H), 1.85 (m, 1H), 1.98 (bs, 3H), 2.12 (m, 1H), 2.28 (m, 1H), 2.43 (s, 3H), 2.60 (m, 1H), 3.95 (d, J=7.06, 1H), 4.17 (d, J=1.46 Hz, 1H), 4.19 (d, J=8.61 Hz, 1H), 4.26 (m, 1H), 4.32 (d, J=8.61 Hz, 1H), 4.96 (bdd, J=9.68, 2.27 Hz, 1H), 5.21 (bd, J=1.46 Hz, 1H), 5.43 (bd, J=9.45 Hz, 1H), 5.54 (m, 2H), 5.69 (d, J=7.07, 1H), 6.25 (bt, J=8.91, 1H), 7.28 (m, 1H), 7.35 to 7.54 (m, 8H), 7.60 (m, 2H), 7.99 (d, J=7.68 Hz, 2H), 8.10 (d, 7.68, 2H).

EXAMPLE 45

2'-benzoyloxy-10-acetoxy docetaxel

To a solution of 2'benzoyloxy docetaxel (1.28 g, 1.4 mmol) in anhydrous THF (7 mL) under nitrogen was added cerium trichloride heptahydrate (CeCl$_3$.7H$_2$O, 0.128 g, 0.344 mmol), and acetic anhydride (0.285 g, 2.8 mmol) and the mixture was stirred at ambient temperature (22 to 25° C.) for 12 h. TLC analysis (60:40 ethyl acetate:hexanes) indicated the complete conversion to a less polar product (R$_f$=0.25) relative to the starting 2'-benzoyloxy docetaxel (R$_f$=0.15). The mixture was diluted with ethyl acetate (20 mL), washed twice with saturated aqueous sodium bicarbonate, brine, dried with sodium sulfate, filtered, and concentrated to give 1.42 g of a solid residue. Flash silica gel purification eluting with ethyl acetate:hexanes (45:55) gave 1.2 g (90% yield) of the desired 2'-benzoyloxy-10-acetoxy docetaxel. $^1$H NMR (400 MHz, CDCl$_3$) δ (ppm): 1.14 (s, 3H), 1.25 (s, 3H), 1.34 (s, 9H), 1.67 (s, 3H), 1.89 (m, 1H), 1.97 (bs, 3H), 2.12 (m, 1H), 2.24 (s, 3H), 2.28 (m, 1H), 2.44 (s, 3H), 2.51 (d, 4.10 Hz, 1H), 2.57 (m, 1H), 3.82 (d, J=7.12 Hz, 1H), 4.17 (d, J=8.50 Hz, 1H)), 4.31 (d, J=8.50, 1H), 4.46 (m, 1H), 4.98 (dd, J=9.65, 2.16 Hz, 1H), 5.42 (bd, J=9.79, 1H), 5.50 (d, J=3.76 Hz, 1H), 5.57 (bm, 1H), 5.67 (d, J=7.10, 1H), 6.26 (bt, J=8.73 Hz, 1H), 6.30 9s, 1H), 7.28 (m, 1H), 7.35 to 7.54 (m, 8H), 7.60 (m, 2H), 7.99 (d, J=7.68 Hz, 2H), 8.10 (d, 7.68, 2H).

EXAMPLE 46

Paclitaxel

To a solution of 2'-benzoyloxy-10-acetoxy docetaxel (0.50 g, 0.524 mmol) and acetonitrile (1 mL) was added 90% aqueous formic acid (2 mL) and the mixture was stirred at ambient 22 to 25° C. temperature over 16 h when TLC analysis (90:10, ethyl acetate:methanol) showed complete conversion to a more polar intermediate (R$_f$=0.35) relative to the starting material (R$_f$=0.75). The solvent and excess acid was removed by azeotropic evaporation with heptane (15 mL). The oily residue was taken up in dichloromethane (2 ml) and heptane (15 mL) and concentrated to give a white powder. The powder was taken up in dichloromethane (5 mL) and triethylamine (2 mL) to induce the benzoyl migration from the oxygen on C2' to the 3'N to give crude Paclitaxel. Purification by silica gel flash column chromatography (60:40 ethyl acetate:hexanes) and pulling and evaporating the clean fractions gave 0.277 g of Paclitaxel. $^1$HNMR of the purified Paclitaxel was identical to a previously known sample. Furthermore, racemic β-lactam was used instead of the optically active enantiomer thus eliminating costly enzyme reagents.

As illustrated in the above examples, using 10-DAB and a β-lactam side chain precursor, paclitaxel and docetaxel were prepared in high yield. This is highlighted by the novel use of a bridging silicon-based protecting group which was easily removed as compared to other protecting groups. Other analogous bridging silicon-based protecting groups gave similar yields of the 7,10-protected 10-DAB derivatives, including those listed in Table 4.

TABLE 4

| Formula Name | Structure |
|---|---|
| 1,5-dichlorohexamethyl-trisiloxane | 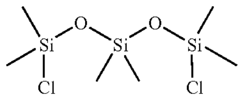 |
| 1,3-dichloro-1,3-diphenyl-1,3-dimethyldisiloxane | 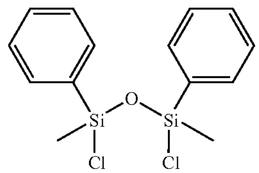 |
| 1,3-dichlorotetraphenyl-disiloxane | 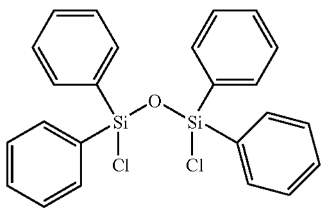 |
| 1,3-divinyl-1,3-dimethyl-1,3-dichlorodisiloxane | 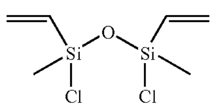 |
| 1,1,3,3-tetraisopropyl-1,3-dichlorodisiloxane | 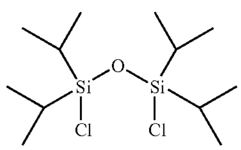 |
| 1,2-bis(chlorodimethylsilyl)ethane | 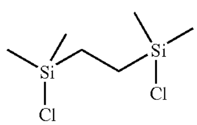 |

What is claimed is:

1. A process for the production of a polycyclic fused ring compound corresponding to Formula (10):

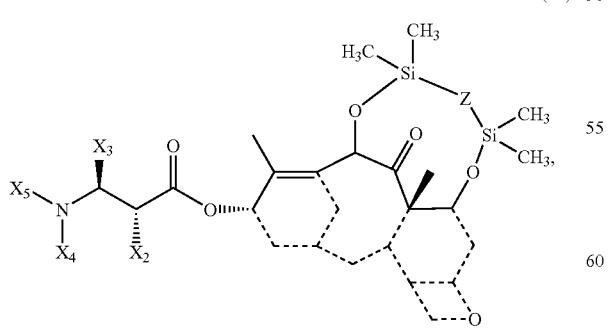

(10)

the process comprising treating a polycyclic fused ring polyol with a bridging silicon-based protecting group and a side chain precursor, wherein
the polycyclic fused ring polyol corresponds to Formula (3):

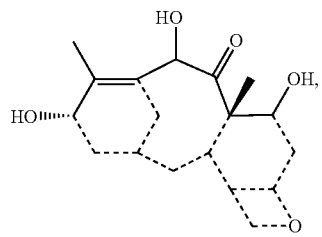

(3)

the bridging silicon-based protecting group corresponds to Formula (4):

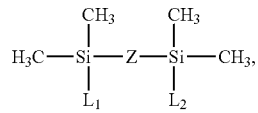

(4)

the side chain precursor corresponds to Formula (6)

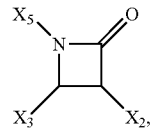

(6)

$X_2$ is alkyl, alkenyl, alkynyl, aryl, heterocyclo, —$OX_6$, —$SX_7$, or —$NX_8X_9$;

$X_3$ is substituted or unsubstituted alkyl, alkenyl, alkynyl, phenyl, or heterocyclo;

$X_5$ is —$COX_{10}$, —$COOX_{10}$, or —$CONHX_{10}$;

$X_6$ is acyl, alkyl, alkenyl, alkynyl, aryl, heteroaryl, hydrogen, or hydroxy protecting group;

$X_7$ is alkyl, alkenyl, alkynyl, aryl, heteroaryl, or sulfhydryl protecting group;

$X_8$ is hydrogen, hydrocarbyl, substituted hydrocarbyl, or heterocyclo;

$X_9$ is an amino protecting group;

$X_{10}$ is hydrocarbyl, substituted hydrocarbyl, or heterocyclo;

$L_1$ and $L_2$ are independently amine, halide, or sulfonate leaving groups;

Z is —$CH_2$—$CH_2$—, —O—$Si(CH_3)(CH_3)$—O—, or —O—; and the dashed lines denote the skeletal structure of the polycyclic fused ring polyol.

2. A process for the production of a polycyclic fused ring compound corresponding to Formula (12):

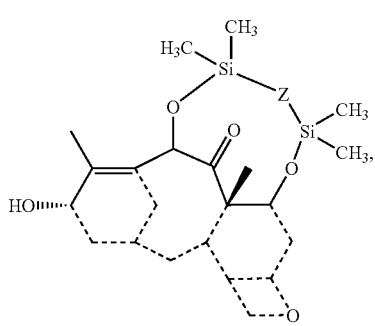

(12)

the process comprising treating a polycyclic fused ring polyol with a bridging silicon-based protecting group, wherein
the polycyclic fused ring polyol corresponds to Formula (3):

(3)

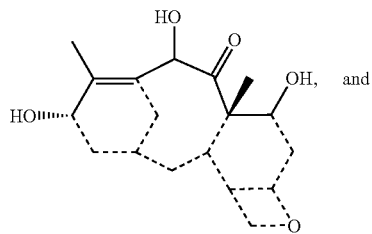

the bridging silicon-based protecting group corresponds to Formula (4):

(4)

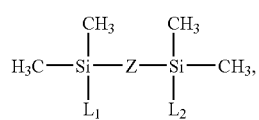

$L_1$ and $L_2$ are independently amine, halide, or sulfonate leaving groups;

Z is —$CH_2$—$CH_2$—, —O—$Si(CH_3)(CH_3)$—O—, or —O—; and the dashed lines denote the skeletal structure of the polycyclic fused ring polyol.

3. A process for the production of a polycyclic fused ring compound corresponding to Formula ($20_R$):

($20_R$)

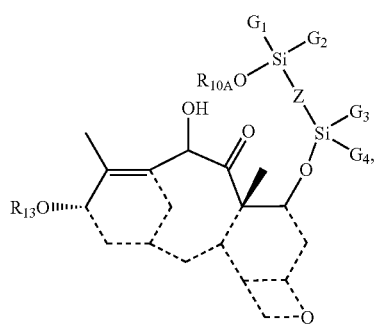

the process comprising treating a polycyclic fused ring compound corresponding to Formula ($9_R$):

($9_R$)

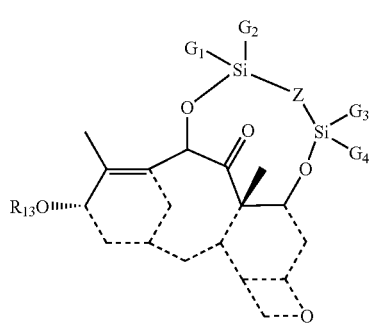

with an alcohol and a base, wherein
the alcohol has the formula $R_{104}OH$;
$G_1$, $G_2$, $G_3$, and $G_4$ are independently hydrocarbyl, substituted hydrocarbyl, alkoxy, or heterocyclo;
$R_{104}$ is hydrocarbyl;
$R_{13}$ is hydrogen or has the structure

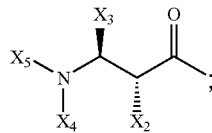

$X_2$ is alkyl, alkenyl, alkynyl, aryl, heterocyclo, —$OX_6$, —$SX_7$, or —$NX_8X_9$;

$X_3$ is substituted or unsubstituted alkyl, alkenyl, alkynyl, phenyl, or heterocyclo;

$X_4$ is hydrogen or an amino protecting group;

$X_5$ is —$COX_{10}$, —$COOX_{10}$, or —$CONHX_{10}$;

$X_6$ is acyl, alkyl, alkenyl, alkynyl, aryl, heteroaryl, hydrogen, or hydroxy protecting group;

$X_7$ is alkyl, alkenyl, alkynyl, aryl, heteroaryl, or sulfhydryl protecting group;

$X_8$ is hydrogen, hydrocarbyl, substituted hydrocarbyl, or heterocyclo;

$X_9$ is an amino protecting group;

$X_{10}$ is hydrocarbyl, substituted hydrocarbyl, or heterocyclo;

Z is hydrocarbyl, substituted hydrocarbyl, heterocyclo, —[O—$Si(Z_{10})(Z_{11})$-]$_n$O—, or —O—;

$Z_{10}$ and $Z_{11}$ are hydrocarbyl;

n is 1 or 2; and the dashed lines denote the skeletal structure of the polycyclic fused ring compound.

4. The process of claim 3 further comprising treating a polycyclic fused ring compound corresponding to Formula ($20_R$) with an acylating agent to produce a compound corresponding to Formula ($20_{R10}$):

($20_{R10}$)

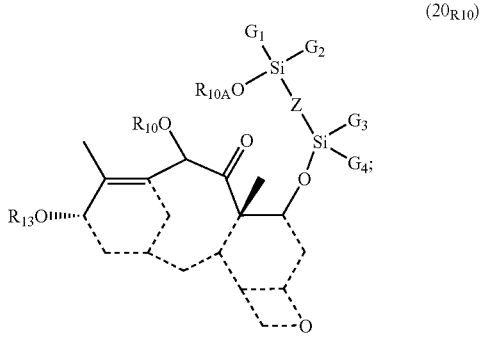

wherein $R_{10}$ is acyl.

5. A polycyclic fused ring compound corresponding to Formula ($9_{R13}$):

($9_{R13}$)

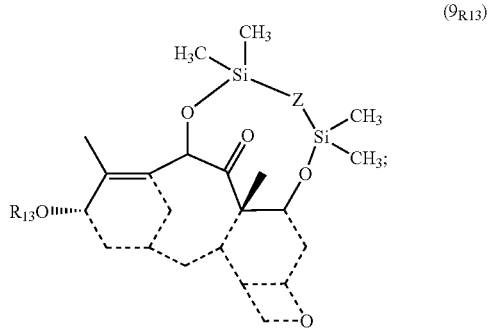

wherein
$R_{13}$ is hydrogen, hydroxy protecting group, a metal, comprises ammonium, or has the structure

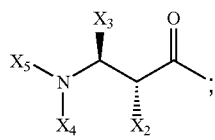

$X_2$ is alkyl, alkenyl, alkynyl, aryl, heterocyclo, —$OX_6$, —$SX_7$, or —$NX_8X_9$;

$X_3$ is substituted or unsubstituted alkyl, alkenyl, alkynyl, phenyl, or heterocyclo;

$X_4$ is hydrogen or an amino protecting group;

$X_5$ is —$COX_{10}$, —$COOX_{10}$, or —$CONHX_{10}$;

$X_6$ is acyl, alkyl, alkenyl, alkynyl, aryl, heteroaryl, hydrogen, or hydroxy protecting group;

$X_7$ is alkyl, alkenyl, alkynyl, aryl, heteroaryl, or sulfhydryl protecting group;

$X_8$ is hydrogen, hydrocarbyl, substituted hydrocarbyl, or heterocyclo;

$X_9$ is an amino protecting group;

$X_{10}$ is hydrocarbyl, substituted hydrocarbyl, or heterocyclo;

Z is —$CH_2$—$CH_2$—, —O—$Si(CH_3)(CH_3)$—O—, or —O—; and the dashed lines denote the skeletal structure of the polycyclic fused ring compound.

6. A polycyclic fused ring compound corresponding to Formula ($20_{R10}$):

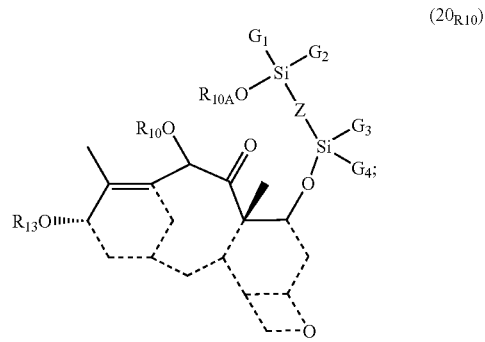

($20_{R10}$)

wherein $G_1$, $G_2$, $G_3$, and $G_4$ are independently hydrocarbyl, substituted hydrocarbyl, alkoxy, or heterocyclo;

$R_{10}$ is hydrogen or acyl;

$R_{10A}$ is hydrocarbyl;

$R_{13}$ is hydrogen or has the structure

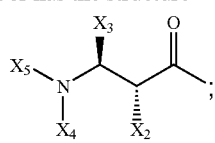

$X_2$ is alkyl, alkenyl, alkynyl, aryl, heterocyclo, —$OX_6$, —$SX_7$, or —$NX_8X_9$;

$X_3$ is substituted or unsubstituted alkyl, alkenyl, alkynyl, phenyl, or heterocyclo;

$X_4$ is hydrogen or an amino protecting group;

$X_5$ is —$COX_{10}$, —$COOX_{10}$, or —$CONHX_{10}$;

$X_6$ is acyl, alkyl, alkenyl, alkynyl, aryl, heteroaryl, hydrogen, or hydroxy protecting group;

$X_7$ is alkyl, alkenyl, alkynyl, aryl, heteroaryl, or sulfhydryl protecting group;

$X_8$ is hydrogen, hydrocarbyl, substituted hydrocarbyl, or heterocyclo;

$X_9$ is an amino protecting group;

$X_{10}$ is hydrocarbyl, substituted hydrocarbyl, or heterocyclo;

Z is hydrocarbyl, substituted hydrocarbyl, heterocyclo, —[O—$Si(Z_{10})(Z_{11})$-]$_n$O—, or —O—;

$Z_{10}$ and $Z_{11}$ are hydrocarbyl;

n is 1 or 2; and the dashed lines denote the skeletal structure of the polycyclic fused ring compound.

7. The process of claim 3 wherein $G_1$, $G_2$, $G_3$, and $G_4$ are independently methyl, ethyl, ethenyl, phenyl, or cyclopentyl.

8. The process of claim 1 wherein $L_1$ and $L_2$ are independently halide leaving groups.

9. The process of claim 3 wherein the bridging silicon-based protecting group is selected from the group consisting of 1,3-dichlorotetramethyldisiloxane; 1,5-dichlorohexamethyltrisiloxane; 1,7-dichlorooctamethyltetrasiloxane; 1,3-dichloro-1,3-diphenyl-1,3-dimethyldisiloxane; 1,3-dichlorotetraphenyldisiloxane; 1,3-divinyl-1,3-dimethyl-1,3-dichlorodisiloxane; 1,1,3,3-tetracyclopenyldichlorodisiloxane; 1,2-bis(chlorodimethylsilyl)ethane; 1,3-bis(chlorodimethylsilyl)propane; 1,6-bis(chlorodimethylsilyl)hexane; and 1,8-bis(chlorodimethylsilyl)octane.

10. The process of claim 1 wherein the polycyclic fused ring polyol treated with the bridging silicon-based protecting group corresponds to Formula (13):

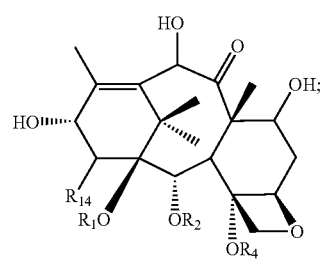

(13)

wherein $R_1$ is hydrogen, acyl, or together with $R_2$ or $R_{14}$ forms carbonate, acetal, or ketal;

$R_2$ is hydrogen, acyl, or together with $R_1$ or $R_4$ forms carbonate, acetal, or ketal;

$R_4$ is hydrogen, acyl, or together with $R_2$ forms carbonate, acetal, or ketal; and $R_{14}$ is hydrogen, hydroxy, acyl, or together with $R_1$ or $R_2$ forms carbonate, acetal, or ketal.

11. The process of claim 1 wherein the polycyclic fused ring polyol treated with the bridging silicon-based protecting group is 10-DAB (23):

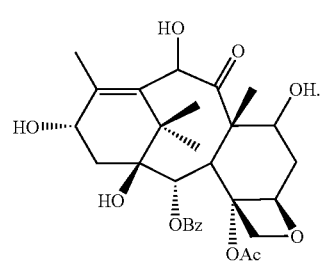

(23)

12. The process of claim 3 wherein the polycyclic fused ring compound treated with the alcohol and the base corresponds to Formula (19):

(19)

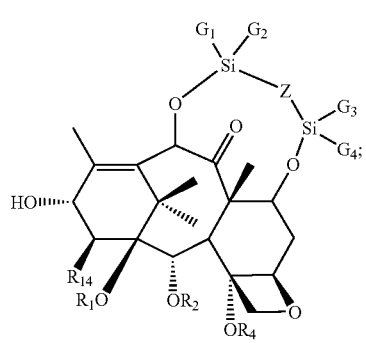

wherein
- $R_1$ is hydrogen, acyl, or together with $R_2$ or $R_{14}$ forms carbonate, acetal, or ketal;
- $R_2$ is hydrogen, acyl, or together with $R_1$ or $R_4$ forms carbonate, acetal, or ketal;
- $R_4$ is hydrogen, acyl, or together with $R_2$ forms carbonate, acetal, or ketal; and
- $R_{14}$ is hydrogen, hydroxy, acyl, or together with $R_1$ or $R_2$ forms carbonate, acetal, or ketal.

13. The process of claim 12 wherein the polycyclic fused ring compound treated with the alcohol and the base corresponds to Formula (29):

(29)

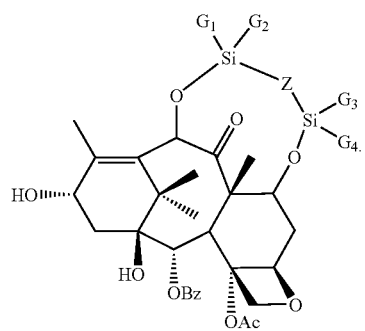

14. The compound of claim 5 wherein the polycyclic fused ring compound corresponds to Formula (19):

(19)

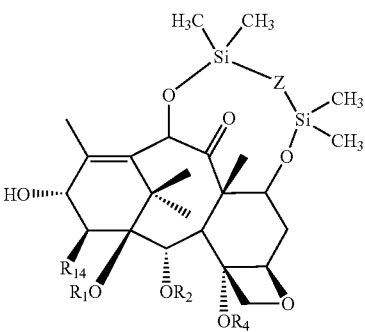

wherein
- $R_1$ is hydrogen, acyl, or together with $R_2$ or $R_{14}$ forms carbonate, acetal, or ketal;
- $R_2$ is hydrogen, acyl, or together with $R_1$ or $R_4$ forms carbonate, acetal, or ketal;
- $R_4$ is hydrogen, acyl, or together with $R_2$ forms carbonate, acetal, or ketal; and
- $R_{14}$ is hydrogen, hydroxy, acyl, or together with $R_1$ or $R_2$ forms carbonate, acetal, or ketal.

15. The compound of claim 14 wherein the polycyclic fused ring compound corresponds to Formula (29):

(29)

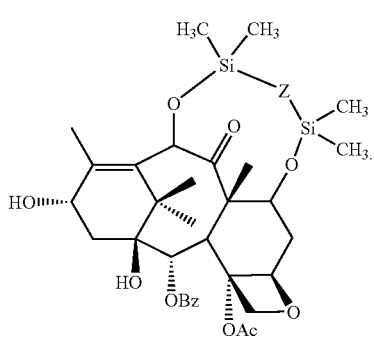

16. The compound of claim 6 wherein the polycyclic fused ring compound corresponds to Formula $(30_R)$:

$(30_R)$

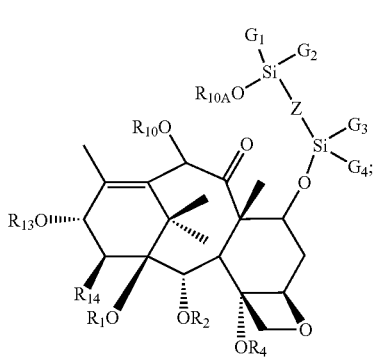

wherein
- $R_1$ is hydrogen, acyl, or together with $R_2$ or $R_{14}$ forms carbonate, acetal, or ketal;
- $R_2$ is hydrogen, acyl, or together with $R_1$ or $R_4$ forms carbonate, acetal, or ketal;
- $R_4$ is hydrogen, acyl, or together with $R_2$ forms carbonate, acetal, or ketal; and
- $R_{14}$ is hydrogen, hydroxy, acyl, or together with $R_1$ or $R_2$ forms carbonate, acetal, or ketal.

17. The compound of claim 16 wherein the polycyclic fused ring compound corresponds to Formula $(40_R)$:

$(40_R)$

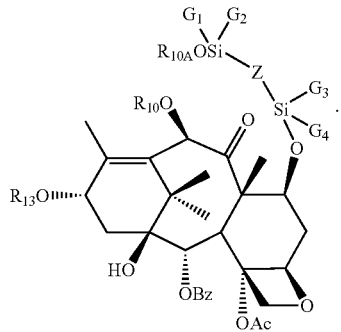

18. The process of claim 1 wherein
- $X_2$ is —$OX_6$;
- $X_3$ is phenyl;
- $X_5$ is —$COOX_{10}$ or —$COX_{10}$;
- $X_6$ is hydrogen or hydroxy protecting group; and
- $X_{10}$ is tert-butyl or phenyl.

19. The process of claim 1 wherein the polycyclic fused ring polyol is treated with the bridging silicon-based protecting group in the presence of an amine base.

20. The process of claim 19 wherein the amine base is dimethylaminopyridine (DMAP).

21. The process of claim 3 wherein the alcohol is methanol.

22. The process of claim 3 wherein the base is triethyl amine or sodium bicarbonate.

23. The process of claim 1 wherein Z is —$CH_2$—$CH_2$—.

24. The process of claim 1 wherein Z is —O—Si($CH_3$)($CH_3$)—O—.

25. The process of claim 1 wherein Z is —O—.

26. The process of claim 1 wherein $L_1$ and $L_2$ are chloro leaving groups.

27. The process of claim 1 wherein Z is —$CH_2$—$CH_2$— and $L_1$ and $L_2$ are chloro leaving groups.

28. The process of claim 1 wherein Z is —O—Si($CH_3$)($CH_3$)—O— and $L_1$ and $L_2$ are chloro leaving groups.

29. The process of claim 1 wherein Z is —O— and $L_1$ and $L_2$ are chloro leaving groups.

30. The process of claim 2 wherein Z is —$CH_2$—$CH_2$—.

31. The process of claim 2 wherein Z is —O—Si($CH_3$)($CH_3$)—O—.

32. The process of claim 2 wherein Z is —O—.

33. The process of claim 2 wherein $L_1$ and $L_2$ are chloro leaving groups.

34. The process of claim 2 wherein Z is —$CH_2$—$CH_2$— and $L_1$ and $L_2$ are chloro leaving groups.

35. The process of claim 2 wherein Z is —O—Si($CH_3$)($CH_3$)—O— and $L_1$ and $L_2$ are chloro leaving groups.

36. The process of claim 2 wherein Z is —O— and $L_1$ and $L_2$ are chloro leaving groups.

37. The process of claim 3 wherein Z is —O— and G1, G2, G3, and G4 are methyl, ethenyl, isopropyl, cyclopentyl, or phenyl.

38. The process of claim 3 wherein $R_{104}$ is alkyl.

39. The process of claim 3 wherein Z is —O— and G1, G2, G3, and G4 are methyl.

40. The process of claim 39 wherein $R_{104}$ is methyl.

41. The process of claim 5 wherein Z is —$CH_2$—$CH_2$—.

42. The process of claim 5 wherein Z is —O—Si($CH_3$)($CH_3$)—O—.

43. The process of claim 5 wherein Z is —O—.

44. The process of claim 5 wherein $X_3$ is phenyl, furyl, or thienyl.

45. The process of claim 6 wherein Z is —O— and G1, G2, G3, and G4 are methyl, ethenyl, isopropyl, cyclopentyl, or phenyl.

46. The process of claim 6 wherein $R_{104}$ is alkyl.

47. The process of claim 6 wherein Z is —O— and G1, G2, G3, and G4 are methyl.

48. The process of claim 47 wherein $R_{104}$ is methyl.

49. The process of any one of claims 1, 3, 5, or 6 wherein
$X_2$ is $OX_6$;
$X_3$ is phenyl, furyl, or thienyl;
$X_5$ is —$COX_{10}$ or —$COOX_{10}$;
$X_6$ is hydrogen or hydroxy protecting group; and
$X_{10}$ is alkyl or phenyl.

50. The process of claim 49 wherein $X_3$ is furyl or thienyl.

* * * * *

UNITED STATES PATENT AND TRADEMARK OFFICE
CERTIFICATE OF CORRECTION

PATENT NO. : 7,667,055 B2  Page 1 of 1
APPLICATION NO. : 11/449535
DATED : February 23, 2010
INVENTOR(S) : Vu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 675 days.

Signed and Sealed this

Seventh Day of December, 2010

David J. Kappos
*Director of the United States Patent and Trademark Office*